US011583536B2

(12) United States Patent
Anton et al.

(10) Patent No.: US 11,583,536 B2
(45) Date of Patent: Feb. 21, 2023

(54) SUBSTITUTED 4-AMINOISOINDOLINE-1,3-DIONE COMPOUNDS AND SECOND ACTIVE AGENTS FOR COMBINED USE

(71) Applicant: Celgene Corporation, Summit, NJ (US)

(72) Inventors: Maria Soraya Carrancio Anton, San Diego, CA (US); Tonia J. Buchholz, Moss Beach, CA (US); Henry Chang, San Francisco, CA (US); Ellen Filvaroff, San Francisco, CA (US); Shailaja Kasibhatla, San Diego, CA (US); Antonia Lopez-Girona, San Diego, CA (US); Adithi Mohan, San Mateo, CA (US); Rama Krishna Narla, San Diego, CA (US); Michael Pourdehnad, San Francisco, CA (US); William Edward Pierceall, Madison, NJ (US); Anjan Guha Thakurta, Basking Ridge, NJ (US)

(73) Assignee: Celgene Corporation, Summit, NJ (US)

( * ) Notice: Subject to any disclaimer, the term of this patent is extended or adjusted under 35 U.S.C. 154(b) by 31 days.

(21) Appl. No.: 17/075,496

(22) Filed: Oct. 20, 2020

(65) Prior Publication Data
US 2021/0113576 A1   Apr. 22, 2021

Related U.S. Application Data

(60) Provisional application No. 62/923,945, filed on Oct. 21, 2019.

(51) Int. Cl.
*A61K 31/5377* (2006.01)
*A61P 35/04* (2006.01)
*A61K 45/06* (2006.01)

(52) U.S. Cl.
CPC .......... *A61K 31/5377* (2013.01); *A61K 45/06* (2013.01); *A61P 35/04* (2018.01)

(58) Field of Classification Search
CPC ............ A61K 31/5377; A61K 31/4045; A61K 31/4184; A61K 31/436; A61K 31/4468; A61K 31/47; A61K 31/506; A61K 31/519; A61K 31/52; A61K 31/55; A61K 31/551; A61K 31/635; A61K 31/675; A61K 31/706; A61K 31/7076; A61K 45/06; A61P 35/00; A61P 35/04
See application file for complete search history.

(56) References Cited

FOREIGN PATENT DOCUMENTS

| WO | WO-2019068904 A1 * | 4/2019 | ......... A61K 31/4184 |
|---|---|---|---|
| WO | WO 2019/209692 A1 | 10/2019 | |
| WO | WO 2020/210418 A1 | 10/2020 | |

OTHER PUBLICATIONS

Castelli et al., Medical Oncology, publ. 2018, vol. 35, pp. 1-7 (Year: 2018).*

* cited by examiner

*Primary Examiner* — Sarah Pihonak
(74) *Attorney, Agent, or Firm* — Jones Day

(57) ABSTRACT

Provided herein are methods of using (S)-2-(2,6-dioxopiperidin-3-yl)-4-((2-fluoro-4-((3-morpholinoazetidin-1-yl) methyl)benzyl)amino)isoindoline-1,3-dione, or an enantiomer, mixture of enantiomers, tautomer, isotopolog, or pharmaceutically acceptable salt thereof, in combination with a second active agent for treating, preventing or managing hematological malignancies. The second active agent is one or more of an HDAC inhibitor, a BCL2 inhibitor, a BTK inhibitor, an mTOR inhibitor, a PI3K inhibitor, a PKCβ inhibitor, a SYK inhibitor, a JAK2 inhibitor, an Aurora kinase inhibitor, an EZH2 inhibitor, a BET inhibitor, a hypomethylating agent, a DOT1L inhibitor, a HAT inhibitor, a WDR5 inhibitor, a DNMT1 inhibitor, an LSD-1 inhibitor, a G9A inhibitor, a PRMT5 inhibitor, a BRD inhibitor, a SUV420H1/H2 inhibitor, a CARM1 inhibitor, a PLK1 inhibitor, an NEK2 inhibitor, an MEK inhibitor, a PHF19 inhibitor, a PIM inhibitor, an IGF-1R inhibitor, an XPO1 inhibitor, a BIRC5 inhibitor, or a chemotherapy.

41 Claims, 10 Drawing Sheets

Sensitivity to Compound 1 single agent in DLBCL cell lines sensitive to resistant

| TMD-8 | SU-DHL-2 | SU-DHL-10 | Pfeiffer | WSU-DLCL2 | OCI-Ly10 | Riva | U2932 | SU-DHL-4 | DB |
|---|---|---|---|---|---|---|---|---|---|
| 58.67 | 108.4 | 123.7 | 288.2 | 362 | 403.5 | 496.3 | 577 | 585.3 | 670.8 |

FIG. 1

SUBSTITUTED 4-AMINOISOINDOLINE-1,3-DIONE COMPOUNDS AND SECOND ACTIVE AGENTS FOR COMBINED USE

This application claims priority to U.S. Provisional Application No. 62/923,945, filed on Oct. 21, 2019, the entirety of which is incorporated herein by reference.

1. FIELD

Provided herein are methods of using (S)-2-(2,6-dioxopiperidin-3-yl)-4-((2-fluoro-4-((3-morpholinoazetidin-1-yl)methyl)benzyl)amino)isoindoline-1,3-dione, or an enantiomer, mixture of enantiomers, tautomer, isotopolog, or pharmaceutically acceptable salt thereof, in combination with a second active agent for treating, preventing or managing hematological malignancies.

2. BACKGROUND

Cancer is characterized primarily by an increase in the number of abnormal cells derived from a given normal tissue, invasion of adjacent tissues by these abnormal cells, or lymphatic or blood-borne spread of malignant cells to regional lymph nodes and metastasis. Clinical data and molecular biologic studies indicate that cancer is a multistep process that begins with minor preneoplastic changes, which may under certain conditions progress to neoplasia. The neoplastic lesion may evolve clonally and develop an increasing capacity for invasion, growth, metastasis, and heterogeneity, especially under conditions in which the neoplastic cells escape the host's immune surveillance. Current cancer therapy may involve surgery, chemotherapy, hormonal therapy and/or radiation treatment to eradicate neoplastic cells in a patient. Recent advances in cancer therapeutics are discussed by Rajkumar et al. in *Nature Reviews Clinical Oncology* 11, 628-630 (2014).

All of the current cancer therapy approaches pose significant drawbacks for the patient. Surgery, for example, may be contraindicated due to the health of a patient or may be unacceptable to the patient. Additionally, surgery may not completely remove neoplastic tissue. Radiation therapy is only effective when the neoplastic tissue exhibits a higher sensitivity to radiation than normal tissue. Radiation therapy can also often elicit serious side effects. Hormonal therapy is rarely given as a single agent. Although hormonal therapy can be effective, it is often used to prevent or delay recurrence of cancer after other treatments have removed the majority of cancer cells.

Despite availability of a variety of chemotherapeutic agents, chemotherapy has many drawbacks. Almost all chemotherapeutic agents are toxic, and chemotherapy causes significant, and often dangerous side effects including severe nausea, bone marrow depression, and immunosuppression. Additionally, even with administration of combinations of chemotherapeutic agents, many tumor cells are resistant or develop resistance to the chemotherapeutic agents. In fact, those cells resistant to the particular chemotherapeutic agents used in the treatment protocol often prove to be resistant to other drugs, even if those agents act by different mechanism from those of the drugs used in the specific treatment. This phenomenon is referred to as pleiotropic drug or multidrug resistance. Because of the drug resistance, many cancers prove or become refractory to standard chemotherapeutic treatment protocols.

Hematological malignancies are cancers that begin in blood-forming tissue, such as the bone marrow, or in the cells of the immune system. Examples of hematological malignancies are leukemia, lymphoma, and myeloma. More specific examples of hematological malignancies include but are not limited to acute myeloid leukemia (AML), acute lymphocytic leukemia (ALL), multiple myeloma (MM), non-Hodgkin's lymphoma (NHL), diffuse large B-cell lymphoma (DLBCL), Hodgkin's lymphoma (HL), T-cell lymphoma (TCL), Burkitt lymphoma (BL), chronic lymphocytic leukemia/small lymphocytic lymphoma (CLL/SLL), marginal zone lymphoma (MZL), and myelodysplastic syndromes (MDS).

3. SUMMARY

Provided herein are methods of using (S)-2-(2,6-dioxopiperidin-3-yl)-4-((2-fluoro-4-((3-morpholinoazetidin-1-yl)methyl)benzyl)amino)isoindoline-1,3-dione (Compound 1), or an enantiomer, mixture of enantiomers, tautomer, isotopolog, or pharmaceutically acceptable salt thereof, in combination with a second active agent for treating, preventing or managing hematological malignancies, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). Compound 1, or an enantiomer, mixture of enantiomers, tautomer, isotopolog, or pharmaceutically acceptable salt thereof, is also collectively referred to as "Compound A".

Also provided for use in the methods provided herein are pharmaceutical compositions formulated for administration by an appropriate route and means containing effective concentrations of a compound provided herein, for example, Compound A, and optionally comprising at least one pharmaceutical carrier. In one embodiment, the compound provided herein is Compound 1.

In one embodiment, the pharmaceutical compositions deliver amounts of Compound A effective for the treatment of a hematological malignancy provided herein in combination with the second active agent provided herein. In one embodiment, the pharmaceutical compositions deliver amounts of Compound A effective for the prevention of a hematological malignancy provided herein in combination with the second active agent provided herein. In one embodiment, the pharmaceutical compositions deliver amounts of Compound A effective for the amelioration of a hematological malignancy provided herein in combination with the second active agent provided herein.

In one embodiment, the pharmaceutical compositions deliver amounts of Compound 1 effective for the treatment of a hematological malignancy provided herein in combination with the second active agent provided herein. In one embodiment, the pharmaceutical compositions deliver amounts of Compound 1 effective for the prevention of a hematological malignancy provided herein in combination with the second active agent provided herein. In one embodiment, the pharmaceutical compositions deliver amounts of Compound 1 effective for the amelioration of a hematological malignancy provided herein in combination with the second active agent provided herein.

In one embodiment, the hematological malignancy is acute myeloid leukemia (AML), acute lymphocytic leukemia (ALL), multiple myeloma (MM), non-Hodgkin's lymphoma (NHL), diffuse large B-cell lymphoma (DLBCL), Hodgkin's lymphoma (HL), T-cell lymphoma (TCL), Burkitt lymphoma (BL), chronic lymphocytic leukemia/small lymphocytic lymphoma (CLL/SLL), marginal zone lymphoma (MZL), or myelodysplastic syndromes (MDS).

In one embodiment, the pharmaceutical compositions deliver amounts of Compound A effective for the treatment of AML in combination with the second active agent provided herein. In one embodiment, the pharmaceutical compositions deliver amounts of Compound A effective for the prevention of AML in combination with the second active agent provided herein. In one embodiment, the pharmaceutical compositions deliver amounts of Compound A effective for the amelioration of AML in combination with the second active agent provided herein.

In one embodiment, the pharmaceutical compositions deliver amounts of Compound 1 effective for the treatment of AML in combination with the second active agent provided herein. In one embodiment, the pharmaceutical compositions deliver amounts of Compound 1 effective for the prevention of AML in combination with the second active agent provided herein. In one embodiment, the pharmaceutical compositions deliver amounts of Compound 1 effective for the amelioration of AML in combination with the second active agent provided herein.

In one embodiment, the pharmaceutical compositions deliver amounts of Compound A effective for the treatment of ALL in combination with the second active agent provided herein. In one embodiment, the pharmaceutical compositions deliver amounts of Compound A effective for the prevention of ALL in combination with the second active agent provided herein. In one embodiment, the pharmaceutical compositions deliver amounts of Compound A effective for the amelioration of ALL in combination with the second active agent provided herein.

In one embodiment, the pharmaceutical compositions deliver amounts of Compound 1 effective for the treatment of ALL in combination with the second active agent provided herein. In one embodiment, the pharmaceutical compositions deliver amounts of Compound 1 effective for the prevention of ALL in combination with the second active agent provided herein. In one embodiment, the pharmaceutical compositions deliver amounts of Compound 1 effective for the amelioration of ALL in combination with the second active agent provided herein.

In one embodiment, the pharmaceutical compositions deliver amounts of Compound A effective for the treatment of MM in combination with the second active agent provided herein. In one embodiment, the pharmaceutical compositions deliver amounts of Compound A effective for the prevention of MM in combination with the second active agent provided herein. In one embodiment, the pharmaceutical compositions deliver amounts of Compound A effective for the amelioration of MM in combination with the second active agent provided herein.

In one embodiment, the pharmaceutical compositions deliver amounts of Compound 1 effective for the treatment of MM in combination with the second active agent provided herein. In one embodiment, the pharmaceutical compositions deliver amounts of Compound 1 effective for the prevention of MM in combination with the second active agent provided herein. In one embodiment, the pharmaceutical compositions deliver amounts of Compound 1 effective for the amelioration of MM in combination with the second active agent provided herein.

In one embodiment, the pharmaceutical compositions deliver amounts of Compound A effective for the treatment of NHL in combination with the second active agent provided herein. In one embodiment, the pharmaceutical compositions deliver amounts of Compound A effective for the prevention of NHL in combination with the second active agent provided herein. In one embodiment, the pharmaceutical compositions deliver amounts of Compound A effective for the amelioration of NHL in combination with the second active agent provided herein.

In one embodiment, the pharmaceutical compositions deliver amounts of Compound 1 effective for the treatment of NHL in combination with the second active agent provided herein. In one embodiment, the pharmaceutical compositions deliver amounts of Compound 1 effective for the prevention of NHL in combination with the second active agent provided herein. In one embodiment, the pharmaceutical compositions deliver amounts of Compound 1 effective for the amelioration of NHL in combination with the second active agent provided herein.

In one embodiment, the pharmaceutical compositions deliver amounts of Compound A effective for the treatment of DLBCL in combination with the second active agent provided herein. In one embodiment, the pharmaceutical compositions deliver amounts of Compound A effective for the prevention of DLBCL in combination with the second active agent provided herein. In one embodiment, the pharmaceutical compositions deliver amounts of Compound A effective for the amelioration of DLBCL in combination with the second active agent provided herein.

In one embodiment, the pharmaceutical compositions deliver amounts of Compound 1 effective for the treatment of DLBCL in combination with the second active agent provided herein. In one embodiment, the pharmaceutical compositions deliver amounts of Compound 1 effective for the prevention of DLBCL in combination with the second active agent provided herein. In one embodiment, the pharmaceutical compositions deliver amounts of Compound 1 effective for the amelioration of DLBCL in combination with the second active agent provided herein.

In one embodiment, the pharmaceutical compositions deliver amounts of Compound A effective for the treatment of HL in combination with the second active agent provided herein. In one embodiment, the pharmaceutical compositions deliver amounts of Compound A effective for the prevention of HL in combination with the second active agent provided herein. In one embodiment, the pharmaceutical compositions deliver amounts of Compound A effective for the amelioration of HL in combination with the second active agent provided herein.

In one embodiment, the pharmaceutical compositions deliver amounts of Compound 1 effective for the treatment of HL in combination with the second active agent provided herein. In one embodiment, the pharmaceutical compositions deliver amounts of Compound 1 effective for the prevention of HL in combination with the second active agent provided herein. In one embodiment, the pharmaceutical compositions deliver amounts of Compound 1 effective for the amelioration of HL in combination with the second active agent provided herein.

In one embodiment, the pharmaceutical compositions deliver amounts of Compound A effective for the treatment of TCL in combination with the second active agent provided herein. In one embodiment, the pharmaceutical compositions deliver amounts of Compound A effective for the prevention of TCL in combination with the second active agent provided herein. In one embodiment, the pharmaceutical compositions deliver amounts of Compound A effective for the amelioration of TCL in combination with the second active agent provided herein.

In one embodiment, the pharmaceutical compositions deliver amounts of Compound 1 effective for the treatment of TCL in combination with the second active agent provided herein. In one embodiment, the pharmaceutical compositions deliver amounts of Compound 1 effective for the prevention of TCL in combination with the second active agent provided herein. In one embodiment, the pharmaceutical compositions deliver amounts of Compound 1 effective for the amelioration of TCL in combination with the second active agent provided herein.

In one embodiment, the pharmaceutical compositions deliver amounts of Compound A effective for the treatment of BL in combination with the second active agent provided herein. In one embodiment, the pharmaceutical compositions deliver amounts of Compound A effective for the prevention of BL in combination with the second active agent provided herein. In one embodiment, the pharmaceutical compositions deliver amounts of Compound A effective for the amelioration of BL in combination with the second active agent provided herein.

In one embodiment, the pharmaceutical compositions deliver amounts of Compound 1 effective for the treatment of BL in combination with the second active agent provided herein. In one embodiment, the pharmaceutical compositions deliver amounts of Compound 1 effective for the prevention of BL in combination with the second active agent provided herein. In one embodiment, the pharmaceutical compositions deliver amounts of Compound 1 effective for the amelioration of BL in combination with the second active agent provided herein.

In one embodiment, the pharmaceutical compositions deliver amounts of Compound A effective for the treatment of CLL/SLL in combination with the second active agent provided herein. In one embodiment, the pharmaceutical compositions deliver amounts of Compound A effective for the prevention of CLL/SLL in combination with the second active agent provided herein. In one embodiment, the pharmaceutical compositions deliver amounts of Compound A effective for the amelioration of CLL/SLL in combination with the second active agent provided herein.

In one embodiment, the pharmaceutical compositions deliver amounts of Compound 1 effective for the treatment of CLL/SLL in combination with the second active agent provided herein. In one embodiment, the pharmaceutical compositions deliver amounts of Compound 1 effective for the prevention of CLL/SLL in combination with the second active agent provided herein. In one embodiment, the pharmaceutical compositions deliver amounts of Compound 1 effective for the amelioration of CLL/SLL in combination with the second active agent provided herein.

In one embodiment, the pharmaceutical compositions deliver amounts of Compound A effective for the treatment of MZL in combination with the second active agent provided herein. In one embodiment, the pharmaceutical compositions deliver amounts of Compound A effective for the prevention of MZL in combination with the second active agent provided herein. In one embodiment, the pharmaceutical compositions deliver amounts of Compound A effective for the amelioration of MZL in combination with the second active agent provided herein.

In one embodiment, the pharmaceutical compositions deliver amounts of Compound 1 effective for the treatment of MZL in combination with the second active agent provided herein. In one embodiment, the pharmaceutical compositions deliver amounts of Compound 1 effective for the prevention of MZL in combination with the second active agent provided herein. In one embodiment, the pharmaceutical compositions deliver amounts of Compound 1 effective for the amelioration of MZL in combination with the second active agent provided herein.

In one embodiment, the pharmaceutical compositions deliver amounts of Compound A effective for the treatment of MDS in combination with the second active agent provided herein. In one embodiment, the pharmaceutical compositions deliver amounts of Compound A effective for the prevention of MDS in combination with the second active agent provided herein. In one embodiment, the pharmaceutical compositions deliver amounts of Compound A effective for the amelioration of MDS in combination with the second active agent provided herein.

In one embodiment, the pharmaceutical compositions deliver amounts of Compound 1 effective for the treatment of MDS in combination with the second active agent provided herein. In one embodiment, the pharmaceutical compositions deliver amounts of Compound 1 effective for the prevention of MDS in combination with the second active agent provided herein. In one embodiment, the pharmaceutical compositions deliver amounts of Compound 1 effective for the amelioration of MDS in combination with the second active agent provided herein.

The compounds or compositions provided herein, or pharmaceutically acceptable derivatives thereof, may be administered simultaneously with, prior to, or after administration of each other and one or more of the above therapies.

These and other aspects of the subject matter described herein will become evident upon reference to the following detailed description.

4. BRIEF DESCRIPTION OF THE DRAWINGS

FIG. 1 shows sensitivity of DLBCL cell line proliferation to Compound 1 treatment, as measured by a Cell Titer Glo assay. Results shown as area under the curve in readouts from Cell Titer Glo assay after exposure to Compound 1. The numbers are Area Under the Curve for each cell line after exposure to Compound 1 at concentrations from 0 to 1000 nM during 5 days.

Figure 5A:
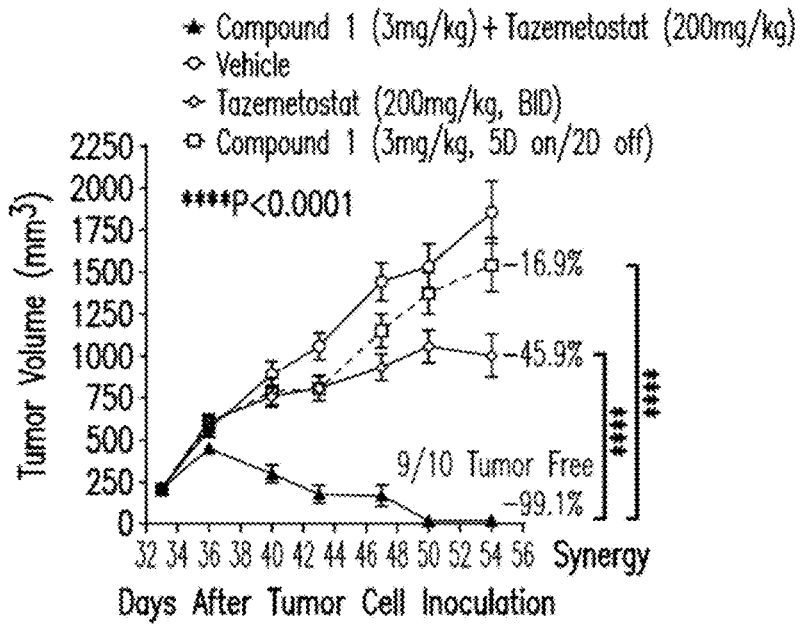
Figure 5B:
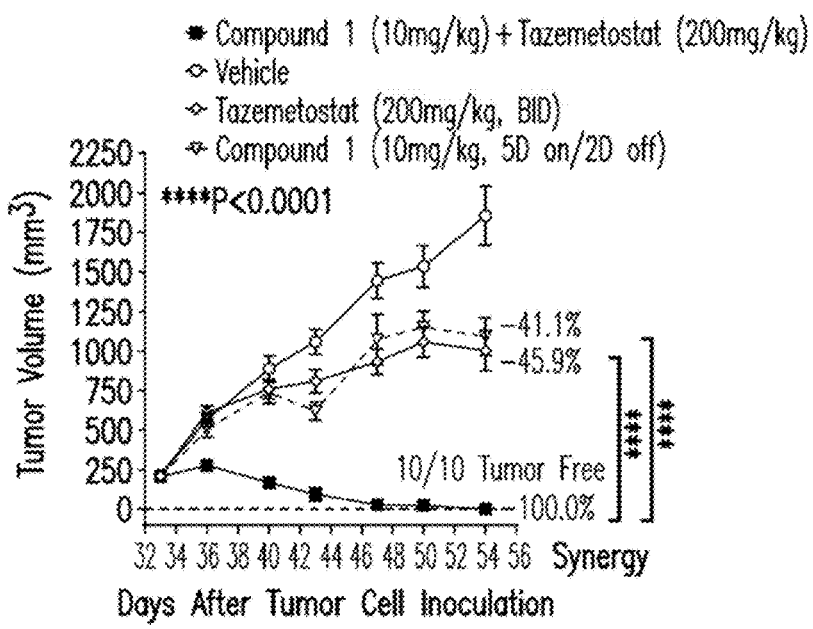
Figure 5C:
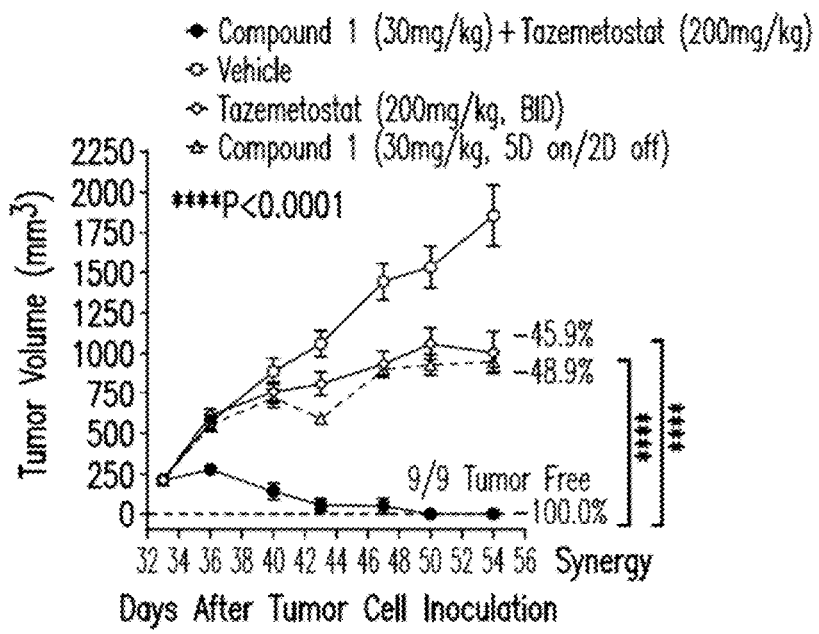

FIG. 5A, FIG. 5B, and FIG. 5C show anti-tumor activity of Compound 1 (at 3, 10, and 30 mg/kg respectively) alone and in combination with tazemetostat in DB (DLBCL) xenograft model.

Figure 6:
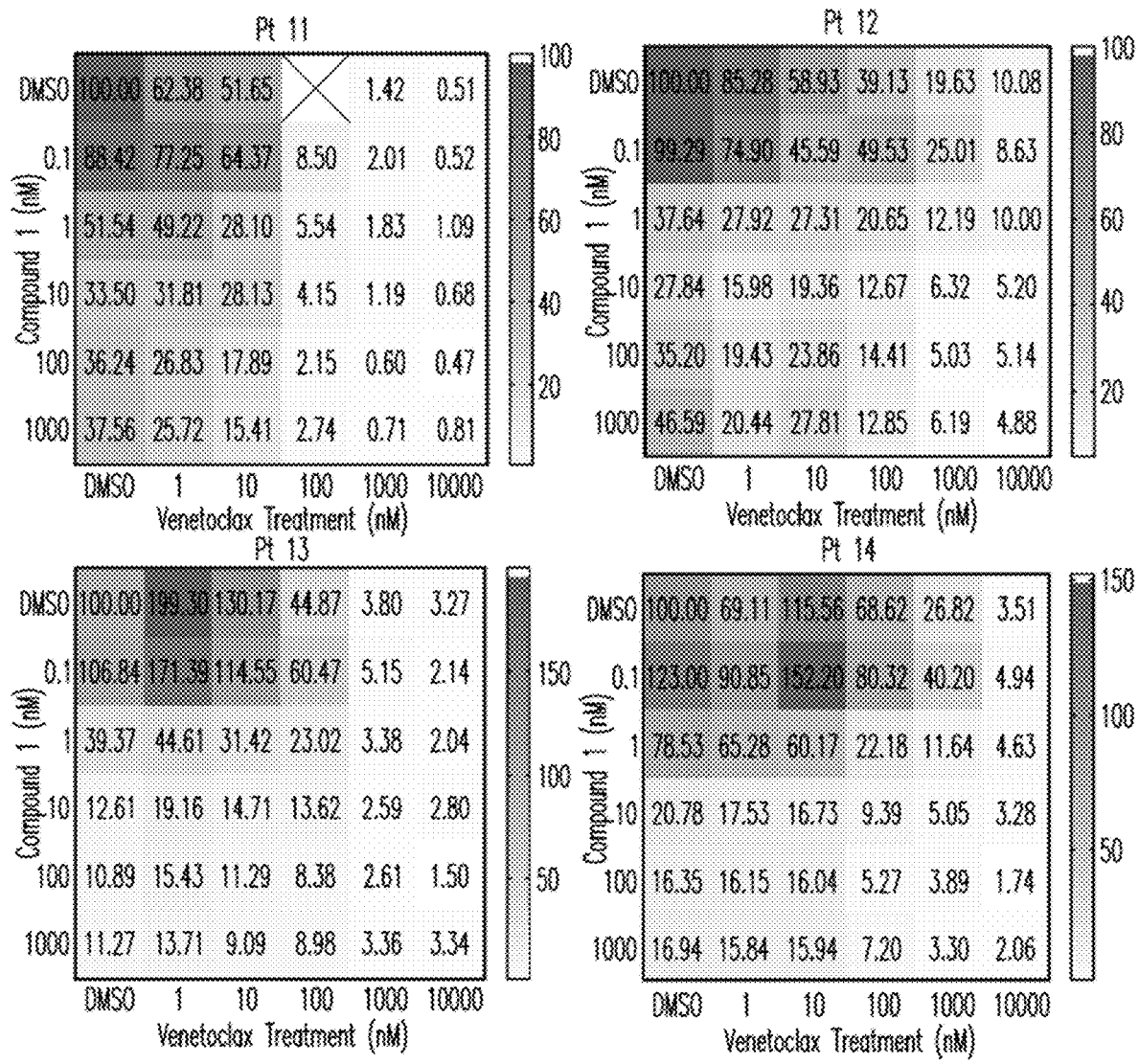

FIG. 6 shows heat map of normalized percentage of tumor cells treated with Compound 1 in combination with venetoclax.

Figure 7:
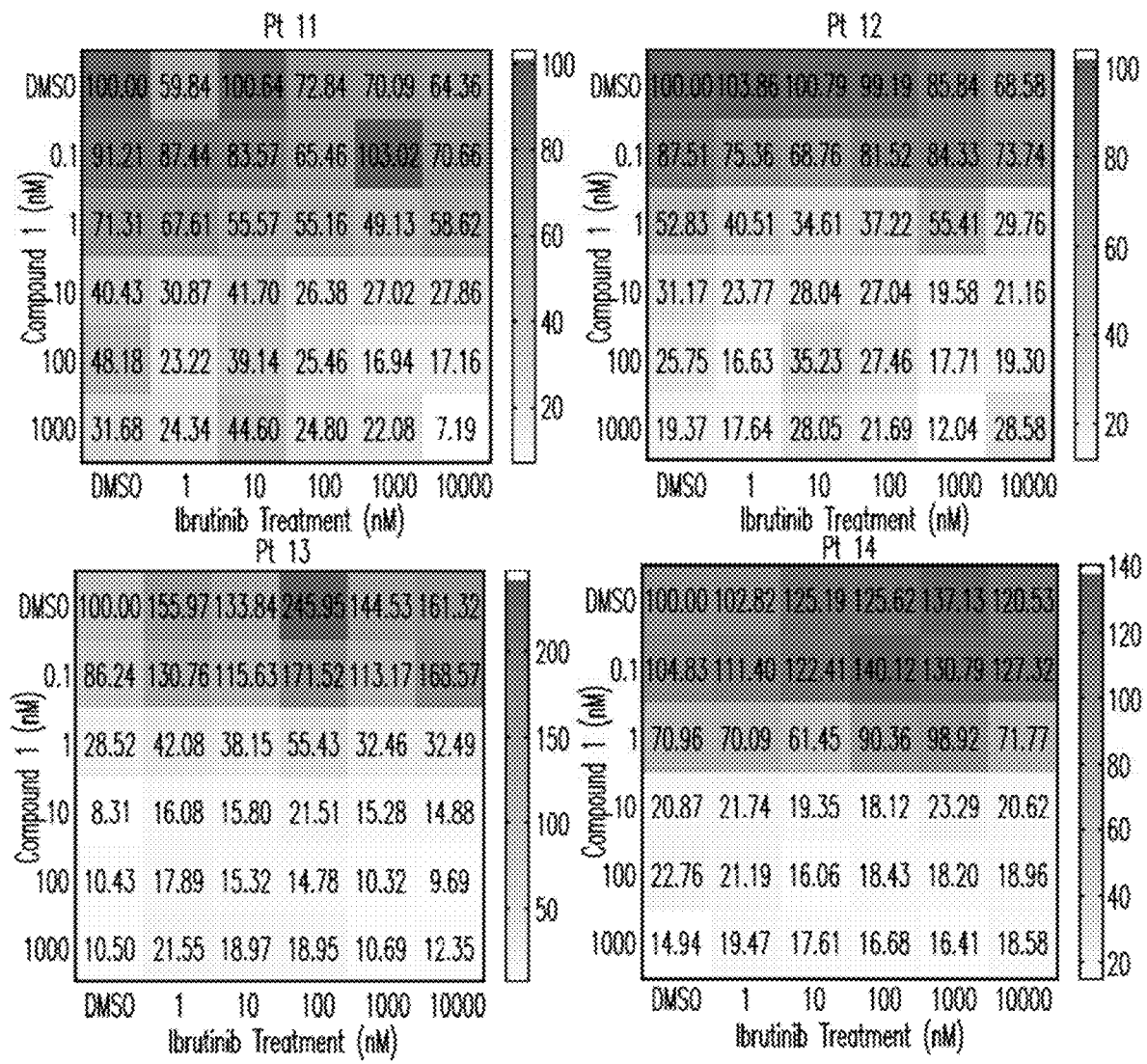

FIG. 7 shows heat map of normalized percentage of tumor cells treated with Compound 1 in combination with ibrutinib.

Figure 8:
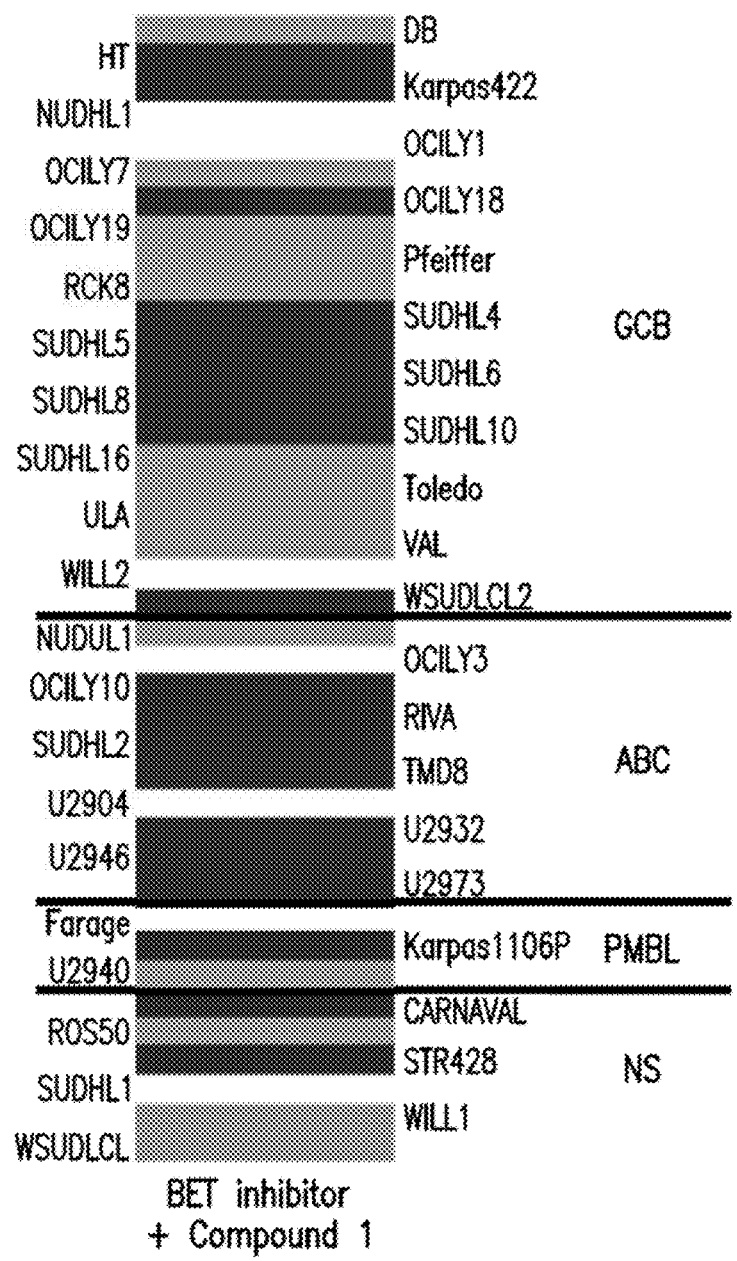

FIG. 8 shows heat map of additive and synergy scoring of combination treatments of DLBCL cell lines with Compound 1 and Compound B.

5. DETAILED DESCRIPTION OF THE INVENTION

5.1 Definitions

Unless defined otherwise, all technical and scientific terms used herein have the same meaning as is commonly understood by one of ordinary skill in the art. All patents, applications, published applications and other publications are incorporated by reference in their entirety. In the event that there is a plurality of definitions for a term herein, those in this section prevail unless stated otherwise.

As used herein, and in the specification and the accompanying claims, the indefinite articles "a" and "an" and the definite article "the" include plural as well as single referents, unless the context clearly indicates otherwise.

As used herein, the terms "comprising" and "including" can be used interchangeably. The terms "comprising" and "including" are to be interpreted as specifying the presence of the stated features or components as referred to, but does not preclude the presence or addition of one or more features, or components, or groups thereof. Additionally, the terms "comprising" and "including" are intended to include examples encompassed by the term "consisting of". Consequently, the term "consisting of" can be used in place of the terms "comprising" and "including" to provide for more specific embodiments of the invention.

The term "consisting of" means that a subject-matter has at least 90%, 95%, 97%, 98% or 99% of the stated features or components of which it consists. In another embodiment the term "consisting of" excludes from the scope of any succeeding recitation any other features or components, excepting those that are not essential to the technical effect to be achieved.

As used herein, the term "or" is to be interpreted as an inclusive "or" meaning any one or any combination. Therefore, "A, B or C" means any of the following: "A; B; C; A and B; A and C; B and C; A, B and C". An exception to this definition will occur only when a combination of elements, functions, steps or acts are in some way inherently mutually exclusive.

As used herein, and unless otherwise specified, the terms "about" and "approximately," when used in connection with doses, amounts, or weight percents of ingredients of a composition or a dosage form, mean a dose, amount, or weight percent that is recognized by one of ordinary skill in the art to provide a pharmacological effect equivalent to that obtained from the specified dose, amount, or weight percent. In certain embodiments, the terms "about" and "approximately," when used in this context, contemplate a dose, amount, or weight percent within 30%, within 20%, within 15%, within 10%, or within 5%, of the specified dose, amount, or weight percent.

As used herein, and unless otherwise specified, the term "pharmaceutically acceptable salts" refers to salts prepared from pharmaceutically acceptable, relatively non-toxic acids, including inorganic acids and organic acids. In certain embodiments, suitable acids include, but are not limited to, acetic, adipic, 4-aminosalicylic, ascorbic, aspartic, benzenesulfonic, benzoic, camphoric, camphorsulfonic, capric, caproic, caprylic, cinnamic, carbonic, citric, cyclamic, dihydrogenphosphoric, 2,5-dihydroxybenzoic (gentisic), 1,2-ethanedisulfonic, ethanesulfonic, fumaric, galactunoric, gluconic, glucuronic, glutamic, glutaric, glycolic, hippuric, hydrobromic, hydrochloric, hydriodic, isobutyric, isethionic, lactic, maleic, malic, malonic, mandelic, methanesulfonic, monohydrogencarbonic, monohydrogen-phosphoric, monohydrogensulfuric, mucic, 1,5-naphthalenedisulfonic, nicotinic, nitric, oxalic, pamoic, pantothenic, phosphoric, phthalic, propionic, pyroglutamic, salicylic, suberic, succinic, sulfuric, tartaric, toluenesulfonic acid, and the like (see, e.g., S. M. Berge et al., *J. Pharm. Sci.,* 66:1-19 (1977); and *Handbook of Pharmaceutical Salts: Properties, Selection and Use*, P. H. Stahl and C. G. Wermuth, Eds., (2002), Wiley, Weinheim). In certain embodiments, suitable acids are strong acids (e.g., with pKa less than about 1), including, but not limited to, hydrochloric, hydrobromic, sulfuric, nitric, methanesulfonic, benzene sulfonic, toluene sulfonic, naphthalene sulfonic, naphthalene disulfonic, pyridinesulfonic, or other substituted sulfonic acids. Also included are salts of other relatively non-toxic compounds that possess acidic character, including amino acids, such as aspartic acid and the like, and other compounds, such as aspirin, ibuprofen, saccharin, and the like. Acid addition salts can be obtained by contacting the neutral form of a compound with a sufficient amount of the desired acid, either neat or in a suitable solvent.

As used herein, and unless otherwise specified, the term "prodrug" of an active compound refers to compounds that are transformed in vivo to yield the active compound or a pharmaceutically acceptable form of the active compound. A prodrug can be inactive when administered to a subject, but is converted in vivo to an active compound, for example, by hydrolysis (e.g., hydrolysis in blood). Prodrugs include compounds wherein a hydroxy, amino or mercapto group is bonded to any group that, when the prodrug of the active compound is administered to a subject, cleaves to form a free hydroxy, free amino or free mercapto group, respectively.

As used herein, and unless otherwise specified, the term "isomer" refers to different compounds that have the same molecular formula. "Stereoisomers" are isomers that differ only in the way the atoms are arranged in space. "Atropisomers" are stereoisomers from hindered rotation about single bonds. "Enantiomers" are a pair of stereoisomers that are non-superimposable mirror images of each other. A mixture of a pair of enantiomers in any proportion can be known as a "racemic" mixture. "Diastereoisomers" are stereoisomers that have at least two asymmetric atoms, but which are not mirror-images of each other. The absolute stereochemistry can be specified according to the Cahn-Ingold-Prelog R—S system. When a compound is an enantiomer, the stereochemistry at each chiral carbon can be specified by either R or S. Resolved compounds whose absolute configuration is unknown can be designated (+) or (−) depending on the direction (dextro- or levorotatory) which they rotate plane polarized light at the wavelength of the sodium D line. However, the sign of optical rotation, (+) and (−), is not related to the absolute configuration of the molecule, R and S. Certain of the compounds described herein contain one or more asymmetric centers and can thus give rise to enantiomers, diastereomers, and other stereoisomeric forms that can be defined, in terms of absolute stereochemistry at each asymmetric atom, as (R)- or (S)-. The present chemical entities, pharmaceutical compositions and methods are meant to include all such possible isomers, including racemic mixtures, optically substantially pure forms and intermediate mixtures. Optically active (R)- and (S)-isomers can be prepared, for example, using chiral synthons or chiral reagents, or resolved using conventional techniques.

"Stereoisomers" can also include E and Z isomers, or a mixture thereof, and cis and trans isomers or a mixture thereof. In certain embodiments, a compound described herein is isolated as either the E or Z isomer. In other embodiments, a compound described herein is a mixture of the E and Z isomers.

"Tautomers" refers to isomeric forms of a compound that are in equilibrium with each other. The concentrations of the isomeric forms will depend on the environment the compound is found in and may be different depending upon, for example, whether the compound is a solid or is in an organic or aqueous solution. For example, in aqueous solution, pyrazoles may exhibit the following isomeric forms, which are referred to as tautomers of each other:

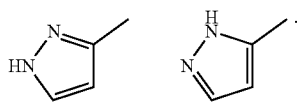

It should also be noted a compound described herein can contain unnatural proportions of atomic isotopes at one or more of the atoms. For example, the compounds may be radiolabeled with radioactive isotopes, such as for example tritium (H), iodine-125 ($^{125}$I) sulfur-35 ($^{35}$S), or carbon-14 ($^{14}$C), or may be isotopically enriched, such as with deuterium ($^{2}$H), carbon-13 ($^{13}$C), or nitrogen-15 ($^{15}$N). As used herein, an "isotopolog" is an isotopically enriched compound. The term "isotopically enriched" refers to an atom having an isotopic composition other than the natural isotopic composition of that atom. "Isotopically enriched" may also refer to a compound containing at least one atom having an isotopic composition other than the natural isotopic composition of that atom. The term "isotopic composition" refers to the amount of each isotope present for a given atom. Radiolabeled and isotopically enriched compounds are useful as therapeutic agents, e.g., cancer therapeutic agents, research reagents, e.g., binding assay reagents, and diagnostic agents, e.g., in vivo imaging agents. All isotopic variations of a compound described herein, whether radioactive or not, are intended to be encompassed within the scope of the embodiments provided herein. In some embodiments, there are provided isotopologs of a compound described herein, for example, the isotopologs are deuterium, carbon-13, and/or nitrogen-15 enriched. As used herein, "deuterated", means a compound wherein at least one hydrogen (H) has been replaced by deuterium (indicated by D or $^{2}$H), that is, the compound is enriched in deuterium in at least one position.

It should be noted that if there is a discrepancy between a depicted structure and a name for that structure, the depicted structure is to be accorded more weight.

As used herein and unless otherwise indicated, the term "treating" means an alleviation, in whole or in part, of a disorder, disease or condition, or one or more of the symptoms associated with a disorder, disease, or condition, or slowing or halting of further progression or worsening of those symptoms, or alleviating or eradicating the cause(s) of the disorder, disease, or condition itself.

As used herein and unless otherwise indicated, the term "preventing" means a method of delaying and/or precluding the onset, recurrence or spread, in whole or in part, of a disorder, disease or condition; barring a subject from acquiring a disorder, disease, or condition; or reducing a subject's risk of acquiring a disorder, disease, or condition.

As used herein and unless otherwise indicated, the term "managing" encompasses preventing the recurrence of the particular disease or disorder in a patient who had suffered from it, lengthening the time a patient who had suffered from the disease or disorder remains in remission, reducing mortality rates of the patients, and/or maintaining a reduction in severity or avoidance of a symptom associated with the disease or condition being managed.

As used herein and unless otherwise indicated, the term "effective amount" in connection with a compound means an amount capable of treating, preventing, or managing a disorder, disease or condition, or symptoms thereof.

As used herein and unless otherwise indicated, the term "subject" or "patient" includes an animal, including, but not limited to, an animal such a cow, monkey, horse, sheep, pig, chicken, turkey, quail, cat, dog, mouse, rat, rabbit or guinea pig, in one embodiment a mammal, in another embodiment a human.

As used herein and unless otherwise indicated, the term "relapsed" refers to a disorder, disease, or condition that responded to treatment (e.g., achieved a complete response) then had progression. The treatment can include one or more lines of therapy. In one embodiment, the disorder, disease or condition has been previously treated with one or more lines of therapy. In another embodiment, the disorder, disease or condition has been previously treated with one, two, three or four lines of therapy. In some embodiments, the disorder, disease or condition is a hematological malignancy.

In one embodiment, "relapsed" DLBCL may refer to DLBCL that has been previously treated with one or more lines of therapy. In one embodiment, the relapsed DLBCL is DLBCL that has been previously treated with one, two, three or four lines of therapy. In one embodiment, the relapsed DLBCL is DLBCL that has been previously treated with two or more lines of treatment.

As used herein and unless otherwise indicated, the term "refractory" refers to a disorder, disease, or condition that has not responded to prior treatment that can include one or more lines of therapy. In one embodiment, the disorder, disease, or condition has been previously treated one, two, three or four lines of therapy. In one embodiment, the disorder, disease, or condition has been previously treated with two or more lines of treatment, and has less than a complete response (CR) to most recent systemic therapy containing regimen. In some embodiments, the disorder, disease or condition is a hematological malignancy.

In one embodiment, "relapsed or refractory" CLL/SLL may refer to CLL/SLL that has been previously treated with one or more lines of therapy. In one embodiment, the relapsed or refractory CLL/SLL is CLL/SLL that has been previously treated with one, two, three or four lines of therapy. In one embodiment, the relapsed or refractory CLL/SLL is CLL/SLL that has been previously treated with two or more lines of therapy. In one embodiment, the relapsed or refractory CLL/SLL is CLL/SLL that has been previously treated with a Bruton's tyrosine kinase (BTK) inhibitor. In one embodiment, the relapsed or refractory CLL/SLL is relapsed or refractory to a BTK inhibitor. In one embodiment, the BTK inhibitor is ibrutinib. In one embodiment, the BTK inhibitor is acalabrutinib. In one embodiment, the BTK inhibitor is zanubrutinib. In one embodiment, the BTK inhibitor is tirabrutinib.

In the context of a cancer, for example, a hematological malignancy, inhibition may be assessed by inhibition of disease progression, inhibition of tumor growth, reduction of primary tumor, relief of tumor-related symptoms, inhibition of tumor secreted factors, delayed appearance of primary or secondary tumors, slowed development of primary or secondary tumors, decreased occurrence of primary or secondary tumors, slowed or decreased severity of secondary effects of disease, arrested tumor growth and regression of tumors, increased Time To Progression (TTP), increased Progression Free Survival (PFS), increased Overall Survival (OS), among others. OS as used herein means the time from treatment onset until death from any cause. TTP as used herein means the time from treatment onset until tumor progression; TTP does not include deaths. In one embodiment, PFS means the time from treatment onset until tumor progression or death. In one embodiment, PFS means the time from the first dose of compound to the first occurrence of disease progression or death from any cause. In one embodiment, PFS rates are computed using the Kaplan-Meier estimates. Event-free survival (EFS) means the time from treatment onset until any treatment failure, including disease progression, treatment discontinuation for any reason, or death. In one embodiment, overall response rate (ORR) means the percentage of patients who achieve a response. In one embodiment, ORR means the sum of the percentage of patients who achieve complete and partial responses. In one embodiment, ORR means the percentage of patients whose best response ≥partial response (PR). In one embodiment, duration of response (DoR) is the time from achieving a response until relapse or disease progression. In one embodiment, DoR is the time from achieving a response ≥partial response (PR) until relapse or disease progression. In one embodiment, DoR is the time from the first documentation of a response until to the first documentation of progressive disease or death. In one embodiment, DoR is the time from the first documentation of a response ≥partial response (PR) until to the first documentation of progressive disease or death. In one embodiment, time to response (TTR) means the time from the first dose of compound to the first documentation of a response. In one embodiment, TTR means the time from the first dose of compound to the first documentation of a response ≥partial response (PR). In the extreme, complete inhibition, is referred to herein as prevention or chemoprevention. In this context, the term "prevention" includes either preventing the onset of clinically evident cancer altogether or preventing the onset of a preclinically evident stage of a cancer. Also intended to be encompassed by this definition is the prevention of transformation into malignant cells or to arrest or reverse the progression of premalignant cells to malignant cells. This includes prophylactic treatment of those at risk of developing a cancer.

In certain embodiments, the treatment of NL may be assessed by the International Workshop Criteria for Malignant Lymphoma (see Cheson et al., *J Cin. Oncol.* 2014, 32(27):3059-3068) and the Deauville Criteria for fluorodeoxyglucose-positron emission tomography (FDG-PET) scan interpretation (Itti et al., *Eur. J. Nuc. Med. Mol. Imaging*, 2013, 40(9):1312-20; Meignan et al., *Leuk Lymphoma*, 2014, 55(1):31-37) ("Lugano criteria"), using the response and end point definition shown in Tables 1-3.

TABLE 1

Criteria for Involvement of Site.

| Tissue Site | Clinical | FDG Avidity | Test | Positive Finding |
| --- | --- | --- | --- | --- |
| Lymph nodes | Palpable | FDG-avid histologies | PET/CT | Increase FDG uptake |
| | | Nonavid disease | CT | Unexplained node enlargement |
| Spleen | Palpable | FDG-avid histologies | PET/CT | Diffuse uptake, solitary mass, miliary lesions, nodules |
| | | Nonavid disease | CT | >13 cm in vertical length, mass, nodules |
| Liver | Palpable | FDG-avid histologies | PET/CT | Diffuse uptake, mass |
| | | Nonavid disease | CT | Nodules |
| CNS | Signs, symptoms | N/A | CT | Mass lesion(s) |
| | | | MRI | Leptomeningeal infiltration, mass lesions |
| | | | CSF assessment | Cytology, flow cytometry |
| Other (eg, skin, lung, GI tract, bone, bone marrow) | Site dependent | N/A | PET/CT[a], biopsy | Lymphoma involvement |

CNS = central nervous system; CSF = cerebrospinal fluid; CT = computed tomography; FDG = fluorodeoxyglucose; GI = gastrointestinal; MRI = magnetic resonance imaging; PET = positron emission tomography; N/A = not applicable.
[a]PET/CT is adequate for determination of bone marrow involvement and can considered highly suggestive for involvement of other extralymphatic sites. Biopsy confirmation of those sites can be considered if necessary.

TABLE 2

Lugano Response Criteria for Non-Hodgkin Lymphoma.

| Response | Site | PET/CT (metabolic response) | CT (Radiologic response) |
|---|---|---|---|
| Complete response | Lymph nodes and extralymphatic sites | Score 1, 2, 3 with or without residual mass on 5-PS (Table 3) | All of the following: Target nodes/nodal masses must regress to ≤1.5 cm in LDi No extralymphatic sites of disease |
| | Non-measured lesion | N/A | Absent |
| | Organ enlargement | N/A | Regress to normal |
| | New Lesions | None | None |
| | Bone Marrow | No evidence of FDG-avid disease in marrow | Normal by morphology; if indeterminate, IHC negative[a] |
| Partial Response | Lymph nodes and extralymphatic sites | Score 4 or 5 on 5-PS with reduced uptake compared with baseline and residual mass(es) of any size At interim these findings suggest responding disease At end of treatment these findings may indicate residual disease | All of the following: ≥50% decrease in SPD of up to 6 target measureable nodes and extranodal sites When a lesion is too small to measure on CT, assign 5 mm × 5 mm as the default value When no longer visible, 0 mm × 0 mm For a node > 5 mm × 5 mm, but smaller than normal, use actual measurement for calculation |
| | Non-measured lesion | N/A | Absent/normal, regressed, but no increase |
| | Organ enlargement | N/A | Spleen must have regressed by >50% in length beyond normal |
| | New Lesions | None | None |
| | Bone Marrow | Residual uptake higher than uptake in normal marrow but reduced compared with baseline. If persistent focal changes in the marrow in the context of nodal response, consider MRI or biopsy or interval scan | N/A |
| Stable Disease | Target nodes/nodal masses, extranodal lesions | Score 4 or 5 on 5-PS with no significant change in FDG uptake from baseline | <50% decrease from baseline of up to 6 dominant, measureable nodes and extranodal sites No criteria for progressive disease are met |
| | Non-measured lesion | N/A | No increase consistent with progression |
| | Organ enlargement | N/A | No increase consistent with progression |
| | New Lesions | None | None |
| | Bone Marrow | No change from baseline | N/A |
| Progressive Disease | Lymph nodes and extralymphatic sites | Score 4 or 5 on 5-PS with an increase in intensity of uptake compared with baseline and/or New FDG-avid foci consistent with lymphoma | At least one of the following: PPD progression: An individual node/lesion must be abnormal with: LDi > 1.5 cm and Increase by ≥50% from PPD nadir and An increase in LDi or SDi from nadir 0.5 cm for lesions ≤ 2 cm 1.0 cm for lesions > 2 cm In the setting of splenomegaly, splenic length must increase by >50% of the extent of its prior increase above baseline (eg, a 15 cm spleen must increase to >16 cm). If no splenomegaly, must increase by at least 2 cm from baseline must increase by at least 2 cm from baseline New or recurrent splenomegaly |
| | Non-measured lesion | None | New or clear progression of preexisting nonmeasured lesions |
| | New Lesions | New FDG-avid foci consistent with lymphoma rather than another etiology (eg, infection, inflammation). If uncertain | Regrowth of previously resolved lesions A new node > 1.5 cm in any axis A new extranodal site |

TABLE 2-continued

Lugano Response Criteria for Non-Hodgkin Lymphoma.

| Response | Site | PET/CT (metabolic response) | CT (Radiologic response) |
|---|---|---|---|
| | | etiology, consider biopsy or interval scan | axis; if <1.0 cm in any axis, its presence must be unequivocal and must be attributable to lymphoma Assessable disease of any size unequivocally attributable to lymphoma |
| | Bone Marrow | New of recurrent FDG-avid foci | New or recurrent involvement |

CMR = complete metabolic response; LDi = longest transverse diameter of a lesion; PPD = cross product of the LDi and perpendicular diameter; SDi = shortest axis perpendicular to the LDi; SPD = sum of the product of the perpendicular diameters for multiple lesions; N/A = not applicable.
<sup>a</sup>Required for CR if bone marrow involvement at baseline
<sup>b</sup> In Waldeyer's ring or extranodal sites with high physiologic uptake or with activation within spleen or marrow; (eg with chemotherapy or myeloid colony stimulating factors), uptake may be greater than normal mediastinum and/or liver. In this circumstance, CMR may be inferred if uptake at sites of initial involvement is no greater than surrounding normal tissue.
<sup>c</sup> FDG-avid lymphomas should have response assessed by PET-CT. Some diseases can typically be followed with CT alone (i.e., marginal zone lymphoma).
<sup>d</sup> PET should be done with contrast-enhanced diagnostic CT and can be done simultaneously or at separate procedures.

TABLE 3

PET Five Point Scale (5-PS).

| | |
|---|---|
| 1 | No uptake above background |
| 2 | Uptake ≤ mediastinum |
| 3 | Uptake > mediastinum but ≤ liver |
| 4 | Uptake moderately > liver |
| 5 | Uptake markedly higher than liver and/or new lesions |
| X | New areas of uptake unlikely to be related to lymphoma |

<sup>a</sup> The Deauville five-point scale (5PS) is an internationally recommended scale for clinical routine and clinical trials using FDG-PET/CT in the initial staging and assessment of treatment response in Hodgkin lymphoma (HL) and certain types of non-Hodgkin lymphomas (NHL).

In one embodiment, the treatment response of CLL/SLL may be assessed by the International Workshop on Chronic Lymphocytic Leukemia criteria (see Hallek, M, et al. iwCLL guidelines for diagnosis, indications for treatment, response assessment, and supportive management of CLL. *Blood*, 131(25), 2745-2760 (2018)) (Table 4).

TABLE 4

Response Definition after Treatment for Chronic Lymphocytic Leukemia Patients.

| Group | Parameter | CR | PR | PD | SD |
|---|---|---|---|---|---|
| A | Lymph nodes | None > 1.5 cm | Decrease ≥ 50% (from the baseline)<sup>a</sup> | Increase ≥ 50% from baseline or from response | Change of −49% to +49% |
| | Liver and/or spleen size<sup>b</sup> | Spleen size, 13 cm; liver size normal | Decrease ≥ 50% (from the baseline) | Increase ≥ 50% from baseline or from response | Change of −49% to +49% |
| | Constitutional symptoms | None | Any | Any | Any |
| | Circulating lymphocyte count | Normal | Decrease ≥50% from baseline | Increase ≥50% over baseline | Change of −49% to +49% |
| B | Platelet count | ≥100 × 10<sup>9</sup>/L | ≥100 × 10<sup>9</sup>/L or increase ≥ 50% over baseline | Decrease of ≥50% from baseline secondary to CLL | Change of −49% to +49% |
| | Hemoglobin | ≥11.0 g/dL (untransfused and without erythropoietin) | ≥11.0 g/dL or increase ≥ 50% over baseline | Decrease of ≥2 g/dL from baseline secondary to CLL | Increase, 11.0 g/dL or <50% over baseline, or decrease < 2 g/dL |

TABLE 4-continued

Response Definition after Treatment for Chronic Lymphocytic Leukemia Patients.

| Group | Parameter | CR | PR | PD | SD |
|---|---|---|---|---|---|
| | Marrow | Normocellular, no CLL cells, no B-lymphoid nodules | Presence of CLL cells, or of B-lymphoid nodules, or not done | Increase of CLL cells by ≥50% on successive biopsies | No change in marrow infiltrate |

CR = complete remission (all of the criteria have to be met); PD = progressive disease (at least 1 of the criteria of group A or group B has to be met); PR = partial remission (for a PR, at least 2 of the parameters of group A and 1 parameter of group B need to improve if previously abnormal; if only 1 parameter of both groups A and B is abnormal before therapy, only 1 needs to improve); SD = stable disease (all of the criteria have to be met; constitutional symptoms alone do not define PD).
[a]Sum of the products of 6 or fewer lymph nodes (as evaluated by CT scans and physical examination in clinical trials or by physical examination in general practice).
[b]Spleen size is considered normal if <13 cm. There is not firmly established international consensus of the size of a normal liver; therefore, liver size should be evaluated by imaging and manual palpation in clinical trials and be recorded according to the definition used in a study protocol.

In one embodiment, the treatment response of CLL/SLL may be assessed by the Eastern Cooperative Oncology Group (ECOG) performance status (Table 5).

TABLE 5

ECOG Performance Status.

| Grade | ECOG |
|---|---|
| 0 | Fully active, able to carry on all pre-disease performance without restriction. |
| 1 | Restricted in physically strenuous activity but ambulatory and able to carry out work of a light or sedentary nature, e.g., light house work, office work. |
| 2 | Ambulatory and capable of all self-care but unable to carry out any work activities. Up and about more than 50% of waking hours. |
| 3 | Capable of only limited self-care, confined to bed or chair more than 50% of waking hours. |
| 4 | Completely disabled. Cannot carry on any self-care. Totally confined to bed or chair. |
| 5 | Dead. |

ECOG = Eastern Cooperative Oncology Group, Robert Comis, MD, Group Chair.
Source: Oken M, et at. Toxicity and response criteria of the Eastern Cooperative Oncology Group. *Am J Clin Oncol*, 5(6): 649-655 (1982).

In certain embodiments, stable disease or lack thereof can be determined by methods known in the art such as evaluation of patient symptoms, physical examination, visualization of the tumor that has been imaged, for example using FDG-PET (fluorodeoxyglucose positron emission tomography), PET/CT (positron emission tomography/computed tomography) scan, MRI (magnetic resonance imaging) of the brain and spine, CSF (cerebrospinal fluid), ophthalmologic exams, vitreal fluid sampling, retinal photograph, bone marrow evaluation and other commonly accepted evaluation modalities.

As used herein and unless otherwise indicated, the terms "co-administration" and "in combination with" include the administration of one or more therapeutic agents (for example, a compound provided herein and another anticancer agent or supportive care agent) either simultaneously, concurrently or sequentially with no specific time limits. In one embodiment, the agents are present in the cell or in the patient's body at the same time or exert their biological or therapeutic effect at the same time. In one embodiment, the therapeutic agents are in the same composition or unit dosage form. In another embodiment, the therapeutic agents are in separate compositions or unit dosage forms.

The term "supportive care agent" refers to any substance that treats, prevents or manages an adverse effect from treatment with another therapeutic agent.

5.2 Compound 1

Provided for use in the methods provided herein is the compound (S)-2-(2,6-dioxopiperidin-3-yl)-4-((2-fluoro-4-((3-morpholinoazetidin-1-yl)methyl)benzyl)amino)isoindoline-1,3-dione, referred to as "Compound 1":

or an enantiomer, mixture of enantiomers, tautomer, isotopolog, or pharmaceutically acceptable salt thereof. Methods of preparing Compound 1 are described in U.S. application Ser. No. 16/390,815, which is incorporated herein by reference in its entirety. Compound 1, or an enantiomer, mixture of enantiomers, tautomer, isotopolog, or pharmaceutically acceptable salt thereof, is also collectively referred to as "Compound A".

In one embodiment, Compound 1 free base is used in the methods provided herein. In one embodiment, a pharmaceutically acceptable salt of Compound 1 is used in the methods provided herein. In one embodiment, a hydrochloride salt of Compound 1 is used in the methods provided herein.

In one embodiment, an enantiomer of Compound 1 (e.g., R-enantiomer of Compound 1) is used in the methods provided herein. In one embodiment, a mixture of enantiomers of Compound 1 (e.g., racemic compound of Compound 1) is used in the methods provided herein.

In one embodiment, a tautomer of Compound 1 is used in the methods provided herein. In one embodiment, an isotopolog of Compound 1 is used in the methods provided herein.

5.3 Second Active Agents

In one embodiment, the second active agent used in the methods provided herein is a histone deacetylase (HDAC) inhibitor. In one embodiment, the HDAC inhibitor is panobinostat, romidepsin, vorinostat, or citarinostat, or a stereoisomer, mixture of stereoisomers, tautomer, isotopolog, or pharmaceutically acceptable salt thereof.

In one embodiment, the HDAC inhibitor is panobinostat, or a tautomer, isotopolog, or pharmaceutically acceptable salt thereof. In one embodiment, the HDAC inhibitor is panobinostat. In one embodiment, the HDAC inhibitor is a pharmaceutically acceptable salt of panobinostat. In one embodiment, the HDAC inhibitor is panobinostat lactate. In one embodiment, the HDAC inhibitor is a mono-lactate salt of panobinostat. Panobinostat has a chemical name of (2E)-N-hydroxy-3-[4-({[2-(2-methyl-1H-indol-3-yl)ethyl]amino}methyl)phenyl]acrylamide, and has the structure:

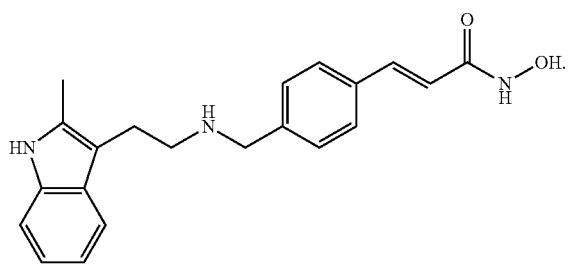 [SMILES: Cc1[nH]c2ccccc2c1CCNCc1ccc(/C=C/C(=O)NO)cc1]

In one embodiment, the HDAC inhibitor is romidepsin, or a stereoisomer, mixture of stereoisomers, tautomer, isotopolog, or pharmaceutically acceptable salt thereof. In one embodiment, the HDAC inhibitor is romidepsin. Romidepsin has a chemical name of (1S,4S,7Z,10S,16E,21R)-7-ethylidene-4,21-bis(1-methylethyl)-2-oxa-12,13-dithia-5,8,20,23-tetraazabicyclo[8.7.6]tricos-16-ene-3,6,9,19,22-pentone, and has the structure:

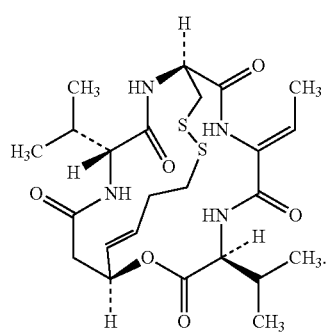 [SMILES: C/C=C1\NC(=O)[C@H]2CSSCC/C=C/[C@H](CC(=O)N[C@H](C(C)C)C(=O)N2)OC(=O)[C@H](C(C)C)NC1=O]

In one embodiment, the HDAC inhibitor is vorinostat, or a tautomer, isotopolog, or pharmaceutically acceptable salt thereof. In one embodiment, the HDAC inhibitor is vorinostat. Vorinostat has a chemical name of N-hydroxy-N'-phenyloctanediamide, and has the structure:

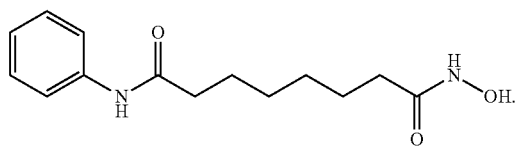 [SMILES: O=C(CCCCCCC(=O)Nc1ccccc1)NO]

In one embodiment, the HDAC inhibitor is a HDAC6 inhibitor. In one embodiment, the HDAC6 inhibitor is citarinostat, or a tautomer, isotopolog, or pharmaceutically acceptable salt thereof. In one embodiment, the HDAC6 inhibitor is citarinostat. Citarinostat (also known as ACY-241) has a chemical name of 2-((2-chlorophenyl)(phenyl)amino)-N-(7-(hydroxyamino)-7-oxoheptyl)pyrimidine-5-carboxamide, and has the structure:

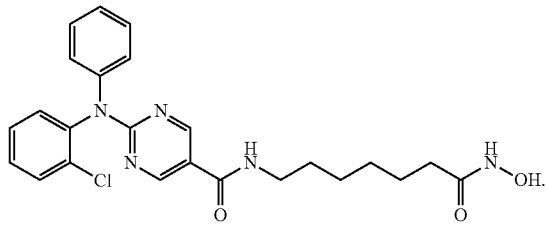 [SMILES: O=C(CCCCCCNC(=O)c1cnc(N(c2ccccc2)c2ccccc2Cl)nc1)NO]

In one embodiment, the second active agent used in the methods provided herein is a B-cell lymphoma 2 (BCL2) inhibitor. In one embodiment, the BCL2 inhibitor is venetoclax, or a tautomer, isotopolog, or pharmaceutically acceptable salt thereof. In one embodiment, the BCL2 inhibitor is venetoclax. Venetoclax has a chemical name of 4-(4-{[2-(4-chlorophenyl)-4,4-dimethylcyclohex-1-en-1-yl]methyl}piperazin-1-yl)-N-({3-nitro-4-[(tetrahydro-2H-pyran-4ylmethyl)amino]phenyl}sulfonyl)-2-(1H-pyrrolo[2,3-b]pyridin-5-yloxy)benzamide, and has the structure:

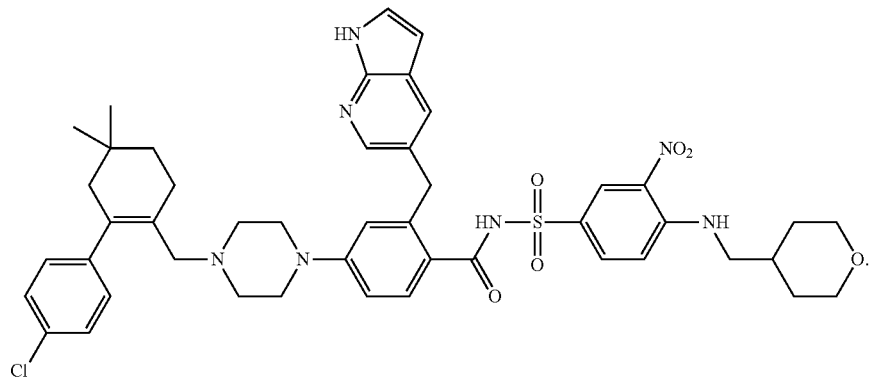 [SMILES: CC1(C)CCC(CN2CCN(c3ccc(C(=O)NS(=O)(=O)c4ccc(NCC5CCOCC5)c([N+](=O)[O-])c4)c(Cc4cnc5[nH]ccc5c4)c3)CC2)=C(c2ccc(Cl)cc2)C1]

In one embodiment, the second active agent used in the methods provided herein is a Bruton's tyrosine kinase (BTK) inhibitor. In one embodiment, the BTK inhibitor is ibrutinib, or acalabrutinib, or a stereoisomer, mixture of stereoisomers, tautomer, isotopolog, or pharmaceutically acceptable salt thereof.

In one embodiment, the BTK inhibitor is ibrutinib, or a stereoisomer, mixture of stereoisomers, tautomer, isotopolog, or pharmaceutically acceptable salt thereof. In one embodiment, the BTK inhibitor is ibrutinib. Ibrutinib has a chemical name of 1-[(3R)-3-[4-amino-3-(4-phenoxyphenyl)-1Hpyrazolo[3,4-d]pyrimidin-1-yl]-1-piperidinyl]-2-propen-1-one, and has the structure:

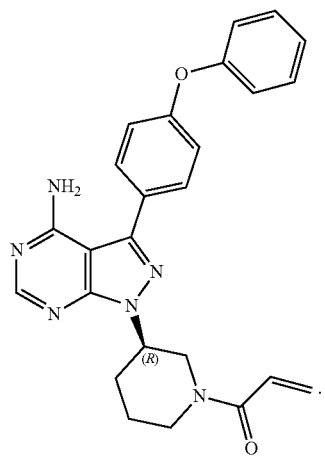

In one embodiment, the BTK inhibitor is acalabrutinib, or a stereoisomer, mixture of stereoisomers, tautomer, isotopolog, or pharmaceutically acceptable salt thereof. In one embodiment, the BTK inhibitor is acalabrutinib. Acalabrutinib has a chemical name of (S)-4-(8-amino-3-(1-(but-2-ynoyl)pyrrolidin-2-yl)imidazo[1,5-a]pyrazin-1-yl)-N-(pyridin-2-yl)benzamide, and has the structure:

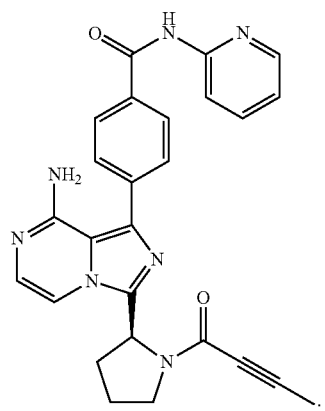 [SMILES: CC#CC(=O)N1CCC[C@H]1c1nc(-c2ccc(C(=O)Nc3ccccn3)cc2)c2c(N)nccn12]

In one embodiment, the second active agent used in the methods provided herein is a mammalian target of rapamycin (mTOR) inhibitor. In one embodiment, the mTOR inhibitor is rapamycin or an analog thereof (also termed rapalog). In one embodiment, the mTOR inhibitor is everolimus, or a stereoisomer, mixture of stereoisomers, tautomer, isotopolog, or pharmaceutically acceptable salt thereof. In one embodiment, the mTOR inhibitor is everolimus. Everolimus has a chemical name of 40-O-(2-hydroxyethyl)-rapamycin, and has the structure:

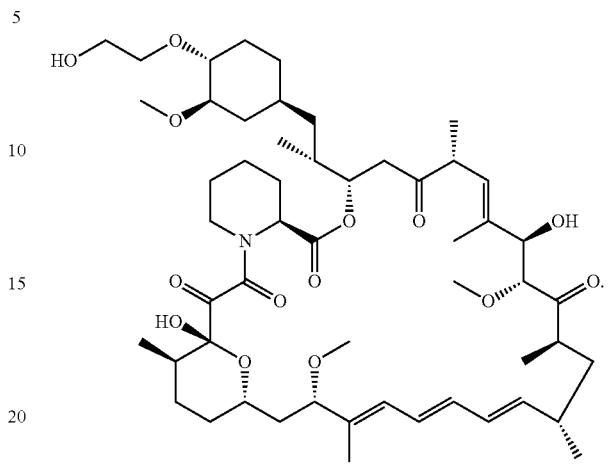

In one embodiment, the second active agent used in the methods provided herein is a phosphoinositide 3-kinase (PI3K) inhibitor. In one embodiment, the PI3K inhibitor is idelalisib, or a stereoisomer, mixture of stereoisomers, tautomer, isotopolog, or pharmaceutically acceptable salt thereof. In one embodiment, the PI3K inhibitor is idelalisib. Idelalisib has a chemical name of 5-fluoro-3-phenyl-2-[(1S)-1-(9H-purin-6ylamino)propyl]quinazolin-4(3H)-one, and has the structure:

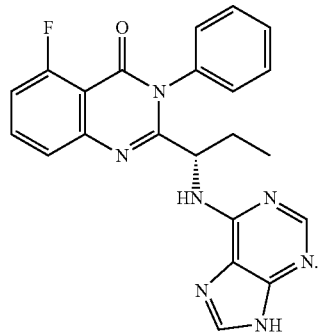 [SMILES: CC[C@H](Nc1ncnc2[nH]cnc12)c1nc2cccc(F)c2c(=O)n1-c1ccccc1]

In one embodiment, the second active agent used in the methods provided herein is a protein kinase C beta (PKCβ or PKC-β) inhibitor. In one embodiment, the PKCβ inhibitor is enzastaurin, or a stereoisomer, mixture of stereoisomers, tautomer, isotopolog, or pharmaceutically acceptable salt thereof. In one embodiment, the PKCβ inhibitor is enzastaurin. In one embodiment, the PKCβ inhibitor is a pharmaceutically acceptable salt of enzastaurin. In one embodiment, the PKCβ inhibitor is a hydrochloride salt of enzastaurin. In one embodiment, the PKCβ inhibitor is a bis-hydrochloride salt of enzastaurin. Enzastaurin has a chemical name of 3-(1-methylindol-3-yl)-4-[1-[1-(pyridin-2-ylmethyl)piperidin-4-yl]indol-3-yl]pyrrole-2,5-dione, and has the structure:

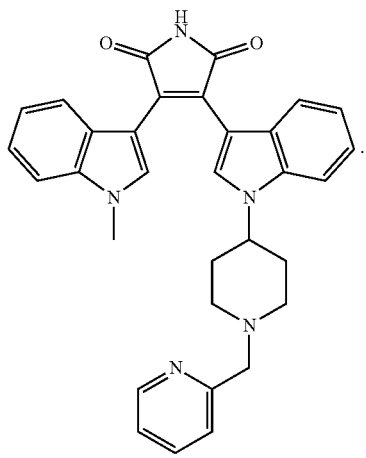 [SMILES: Cn1cc(C2=C(c3cn(C4CCN(Cc5ccccn5)CC4)c4ccccc34)C(=O)NC2=O)c2ccccc21]

In one embodiment, the second active agent used in the methods provided herein is a spleen tyrosine kinase (SYK) inhibitor. In one embodiment, the SYK inhibitor is fostamatinib, or a tautomer, isotopolog, or pharmaceutically acceptable salt thereof. In one embodiment, the SYK inhibitor is fostamatinib. In one embodiment, the SYK inhibitor is a pharmaceutically acceptable salt of fostamatinib. In one embodiment, the SYK inhibitor is fostamatinib disodium hexahydrate. Fostamatinib (also known as R788) has a chemical name of (6-((5-fluoro-2-((3,4,5-trimethoxyphenyl)amino)pyrimidin-4-yl)amino)-2,2-dimethyl-3-oxo-2,3-dihydro-4H-pyrido[3,2-b][1,4]oxazin-4-yl)methyl dihydrogen phosphate, and has the structure:

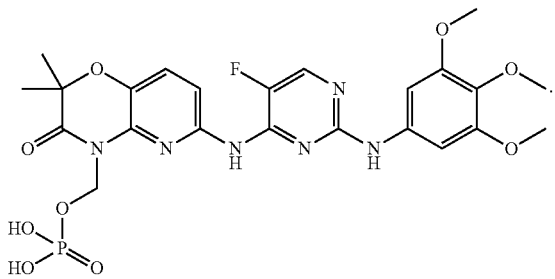

In one embodiment, the second active agent used in the methods provided herein is a Janus kinase 2 (JAK2) inhibitor. In one embodiment, the JAK2 inhibitor is fedratinib, pacritinib, ruxolitinib, baricitinib, gandotinib, lestaurtinib, or momelotinib, or a stereoisomer, mixture of stereoisomers, tautomer, isotopolog, or pharmaceutically acceptable salt thereof.

In one embodiment, the JAK2 inhibitor is fedratinib, or a tautomer, isotopolog, or pharmaceutically acceptable salt thereof. In one embodiment, the JAK2 inhibitor is fedratinib. Fedratinib has a chemical name of N-tert-butyl-3-[(5-methyl-2-{4-[2-(pyrrolidin-1-yl)ethoxy]anilino}pyrimidin-4-yl)amino]benzenesulfonamide, and has the structure:

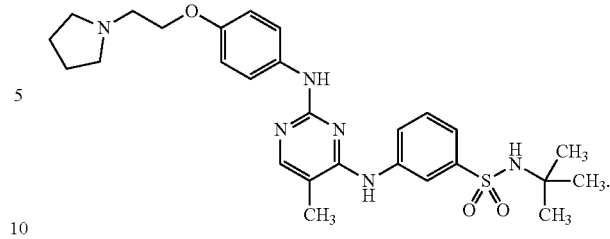

In one embodiment, the JAK2 inhibitor is pacritinib, or a tautomer, isotopolog, or pharmaceutically acceptable salt thereof. In one embodiment, the JAK2 inhibitor is pacritinib. Pacritinib has the structure:

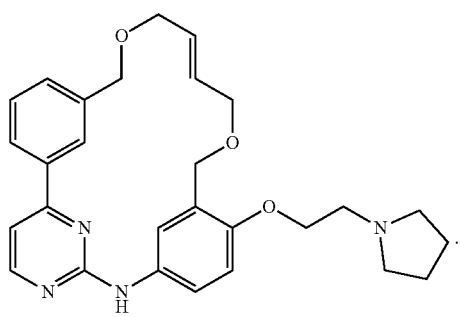 [SMILES: C1=C/COCc2cc(ccc2OCCN2CCCC2)Nc2nccc(n2)-c2cccc(c2)COC/1]

In one embodiment, the JAK2 inhibitor is ruxolitinib, or a stereoisomer, mixture of stereoisomers, tautomer, isotopolog, or pharmaceutically acceptable salt thereof. In one embodiment, the JAK2 inhibitor is ruxolitinib. In one embodiment, the JAK2 inhibitor is a pharmaceutically acceptable salt of ruxolitinib. In one embodiment, the JAK2 inhibitor is ruxolitinib phosphate. Ruxolitinib has a chemical name of (R)-3-(4-(7H-pyrrolo[2,3-d]pyrimidin-4-yl)-1H-pyrazol-1-yl)-3-cyclopentylpropanenitrile, and has the structure.

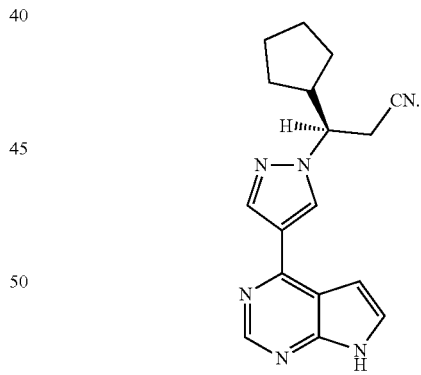

In one embodiment, the second active agent used in the methods provided herein is an Aurora kinase inhibitor. In one embodiment, the Aurora kinase inhibitor is an Aurora kinase A inhibitor. In one embodiment, the Aurora kinase inhibitor is an Aurora kinase B inhibitor. In one embodiment, the Aurora kinase inhibitor is pan-Aurora kinase inhibitor.

In one embodiment, the Aurora kinase inhibitor is alisertib, or a tautomer, isotopolog, or pharmaceutically acceptable salt thereof. In one embodiment, the Aurora kinase inhibitor is alisertib. Alisertib has a chemical name of 4-((9-chloro-7-(2-fluoro-6-methoxyphenyl)-5H-benzo[c]pyrimido[4,5-e]azepin-2-yl)amino)-2-methoxybenzoic acid, and has the structure:

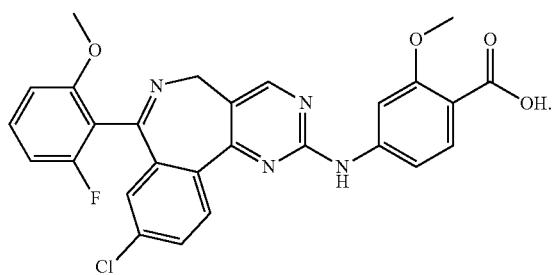 [SMILES: COc1cc(Nc2ncc3c(n2)-c2ccc(Cl)cc2C(c2c(F)cccc2OC)=NC3)ccc1C(=O)O]

In one embodiment, the Aurora kinase inhibitor is barasertib (also known as AZD1152) or AZD1152-HQPA, or a tautomer, isotopolog, or pharmaceutically acceptable salt thereof. In one embodiment, the Aurora kinase inhibitor is barasertib. In one embodiment, the Aurora kinase inhibitor is AZD1152-HQPA. AZD1152-HQPA (also known as AZD2811) has a chemical name of 2-(3-((7-(3-(ethyl(2-hydroxyethyl)amino)propoxy)quinazolin-4-yl)amino)-1H-pyrazol-5-yl)-N-(3-fluorophenyl)acetamide, and has the structure:

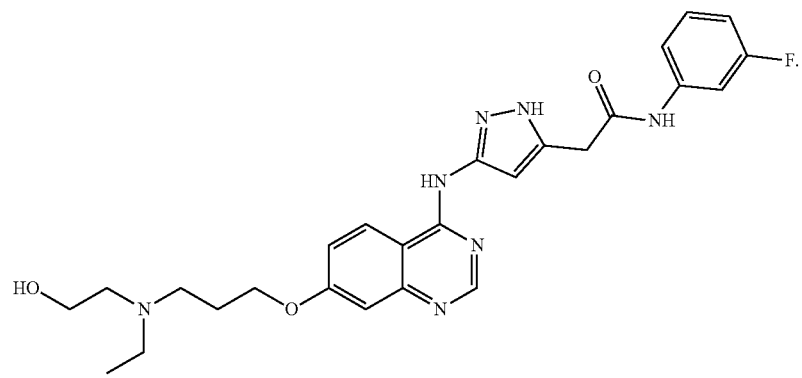 [SMILES: CCN(CCO)CCCOc1ccc2c(Nc3cc(CC(=O)Nc4cccc(F)c4)[nH]n3)ncnc2c1]

Barasertib is a dihydrogen phosphate prodrug of AZD1152-HQPA, and has the structure:

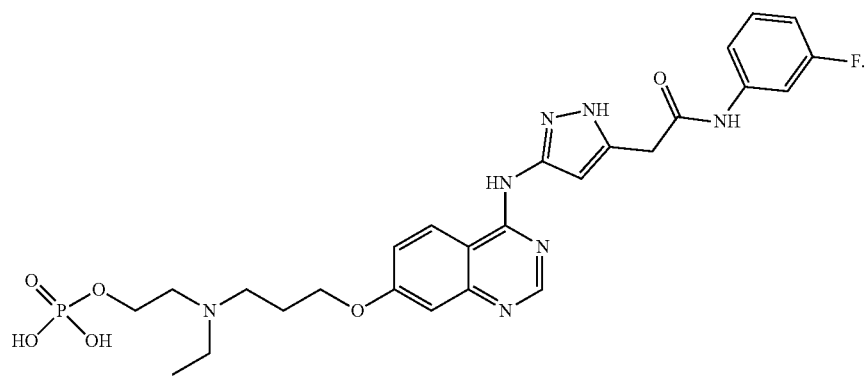 [SMILES: CCN(CCCOc1ccc2c(Nc3cc(CC(=O)Nc4cccc(F)c4)[nH]n3)ncnc2c1)CCOP(=O)(O)O]

In one embodiment, the Aurora kinase inhibitor is danusertib, or a stereoisomer, mixture of stereoisomers, tautomer, isotopolog, or pharmaceutically acceptable salt thereof. In one embodiment, the Aurora kinase inhibitor is danusertib. Danusertib (also known as PHA-739358) has the structure:

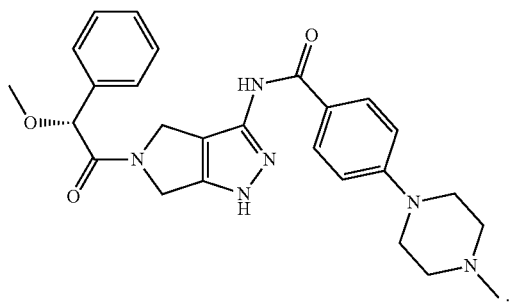

In one embodiment, the Aurora kinase inhibitor is AT9283, or a tautomer, isotopolog, or pharmaceutically acceptable salt thereof. In one embodiment, the Aurora kinase inhibitor is AT9283. AT9283 has the structure:

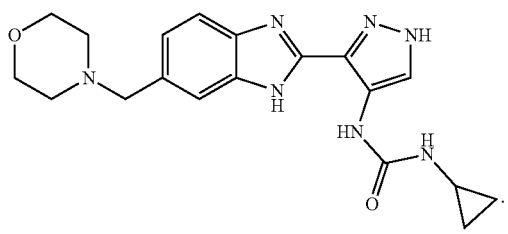 [SMILES: O=C(Nc1c[nH]nc1-c1nc2ccc(CN3CCOCC3)cc2[nH]1)NC1CC1]

In one embodiment, the Aurora kinase inhibitor is PF-03814735, or a stereoisomer, mixture of stereoisomers, tautomer, isotopolog, or pharmaceutically acceptable salt thereof. In one embodiment, the Aurora kinase inhibitor is PF-03814735. PF-03814735 has the structure:

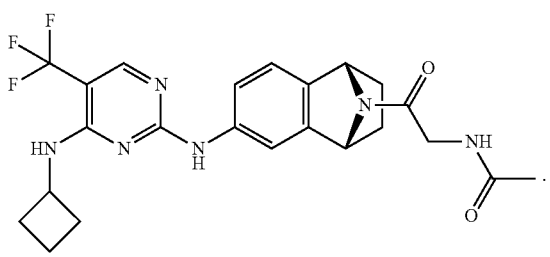 [SMILES: CC(=O)NCC(=O)N1[C@@H]2CC[C@H]1c1ccc(Nc3ncc(C(F)(F)F)c(NC4CCC4)n3)cc12]

In one embodiment, the Aurora kinase inhibitor is AMG900, or a tautomer, isotopolog, or pharmaceutically acceptable salt thereof. In one embodiment, the Aurora kinase inhibitor is AMG900. AMG900 has the structure:

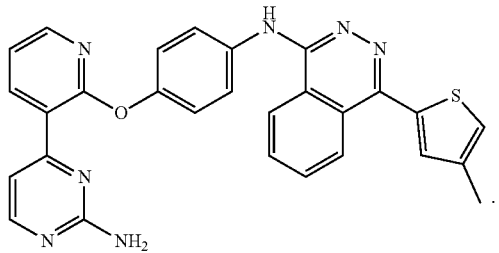 [SMILES: Cc1csc(-c2nnc(Nc3ccc(Oc4ncccc4-c4ccnc(N)n4)cc3)c3ccccc23)c1]

In one embodiment, the Aurora kinase inhibitor is tozasertib, or a tautomer, isotopolog, or pharmaceutically acceptable salt thereof. In one embodiment, the Aurora kinase inhibitor is tozasertib. Tozasertib (also known as VX-680 or MK-0457) has the structure:

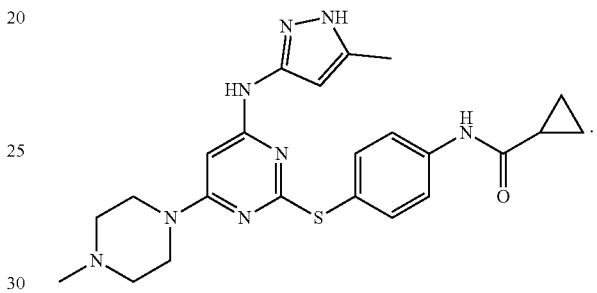

In one embodiment, the Aurora kinase inhibitor is ZM447439, or a tautomer, isotopolog, or pharmaceutically acceptable salt thereof. In one embodiment, the Aurora kinase inhibitor is ZM447439. ZM447439 has the structure:

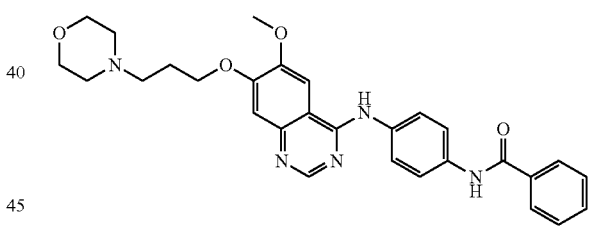

In one embodiment, the Aurora kinase inhibitor is MLN8054, or a tautomer, isotopolog, or pharmaceutically acceptable salt thereof. In one embodiment, the Aurora kinase inhibitor is MLN8054. MLN8054 has the structure:

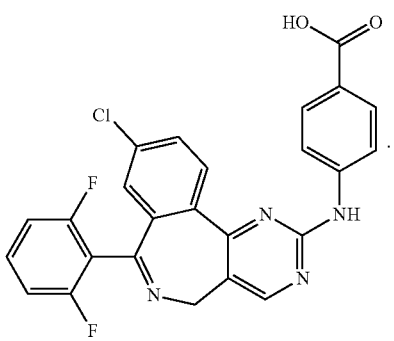 [SMILES: O=C(O)c1ccc(Nc2ncc3c(n2)-c2ccc(Cl)cc2C(c2c(F)cccc2F)=NC3)cc1]

In one embodiment, the Aurora kinase inhibitor is hesperadin, or a tautomer, isotopolog, or pharmaceutically acceptable salt thereof. In one embodiment, the Aurora kinase inhibitor is hesperadin. In one embodiment, the Aurora kinase inhibitor is a hydrochloride salt of hesperadin. Hesperadin has the structure:

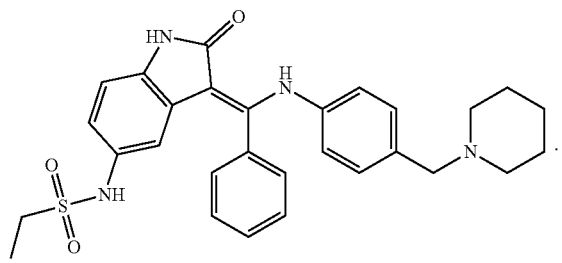 [SMILES: CCS(=O)(=O)Nc1ccc2c(c1)/C(=C(/Nc1ccc(CN3CCCCC3)cc1)c1ccccc1)C(=O)N2]

In one embodiment, the Aurora kinase inhibitor is SNS-314, or a tautomer, isotopolog, or pharmaceutically acceptable salt thereof. In one embodiment, the Aurora kinase inhibitor is SNS-314. In one embodiment, the Aurora kinase inhibitor is a mesylate salt of SNS-314. SNS-314 has the structure:

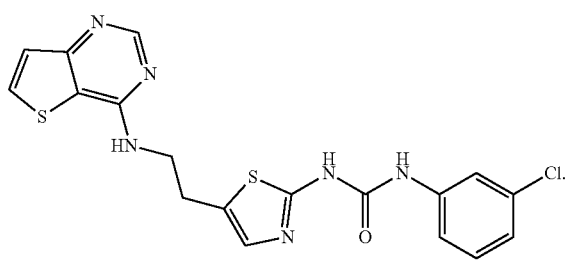 [SMILES: O=C(Nc1cccc(Cl)c1)Nc1ncc(CCNc2ncnc3ccsc23)s1]

In one embodiment, the Aurora kinase inhibitor is PHA-680632, or a tautomer, isotopolog, or pharmaceutically acceptable salt thereof. In one embodiment, the Aurora kinase inhibitor is PHA-680632. PHA-680632 has the structure:

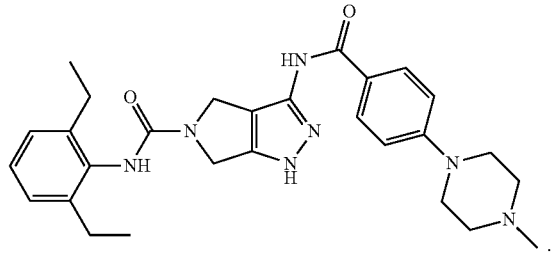 [SMILES: CCc1cccc(CC)c1NC(=O)N1Cc2[nH]nc(NC(=O)c3ccc(N4CCN(C)CC4)cc3)c2C1]

In one embodiment, the Aurora kinase inhibitor is CYC116, or a tautomer, isotopolog, or pharmaceutically acceptable salt thereof. In one embodiment, the Aurora kinase inhibitor is CYC116. CYC116 has the structure:

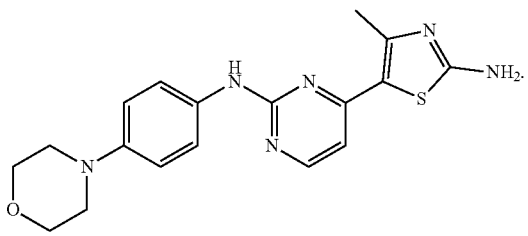 [SMILES: Cc1nc(N)sc1-c1ccnc(Nc2ccc(N3CCOCC3)cc2)n1]

In one embodiment, the Aurora kinase inhibitor is GSK1070916, or a tautomer, isotopolog, or pharmaceutically acceptable salt thereof. In one embodiment, the Aurora kinase inhibitor is GSK1070916. GSK1070916 has the structure:

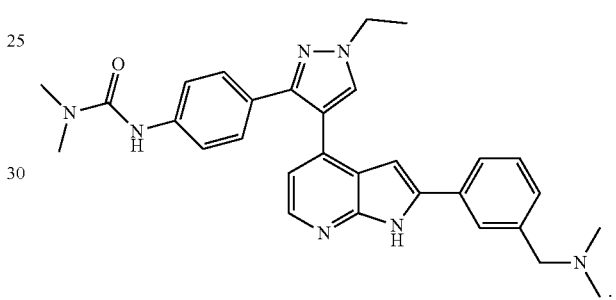

In one embodiment, the Aurora kinase inhibitor is TAK-901, or a tautomer, isotopolog, or pharmaceutically acceptable salt thereof. In one embodiment, the Aurora kinase inhibitor is TAK-901. TAK-901 has the structure:

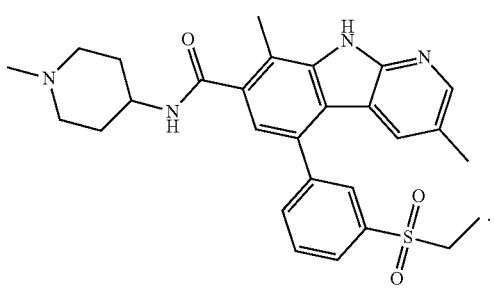 [SMILES: CCS(=O)(=O)c1cccc(-c2cc(C(=O)NC3CCN(C)CC3)c(C)c3[nH]c4ncc(C)cc4c23)c1]

In one embodiment, the Aurora kinase inhibitor is CCT137690, or a tautomer, isotopolog, or pharmaceutically acceptable salt thereof. In one embodiment, the Aurora kinase inhibitor is CCT137690. CCT137690 has the structure:

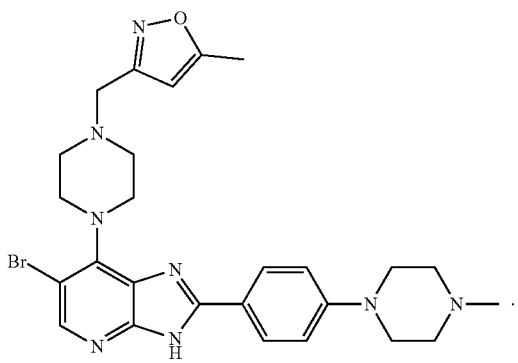 [SMILES: Cc1cc(CN2CCN(c3c(Br)cnc4[nH]c(-c5ccc(N6CCN(C)CC6)cc5)nc34)CC2)no1]

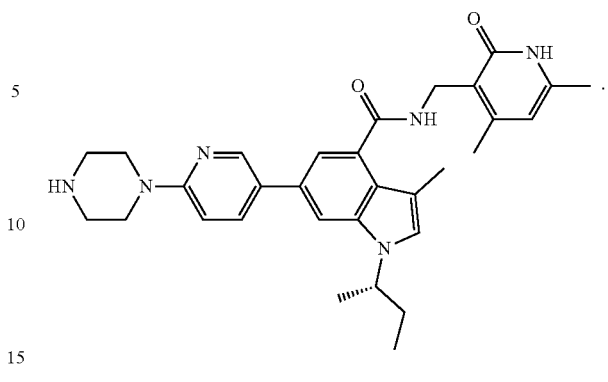

In one embodiment, the second active agent used in the methods provided herein is an enhancer of zeste homolog 2 (EZH2) inhibitor. In one embodiment, the EZH2 inhibitor is tazemetostat, GSK126, CPI-1205, 3-deazaneplanocin A (DZNep), EPZ005687, EI1, UNC1999, or sinefungin, or a stereoisomer, mixture of stereoisomers, tautomer, isotopolog, or pharmaceutically acceptable salt thereof.

In one embodiment, the EZH2 inhibitor is tazemetostat, or a tautomer, isotopolog, or pharmaceutically acceptable salt thereof. In one embodiment, the EZH2 inhibitor is tazemetostat. Tazemetostat (also known as EPZ-6438) has a chemical name of N-[(1,2-dihydro-4,6-dimethyl-2-oxo-3-pyridinyl)methyl]-5-[ethyl(tetrahydro-2H-pyran-4-yl)amino]-4-methyl-4'-(4-morpholinylmethyl)-[1,1'-biphenyl]-3-carboxamide, and has the structure:

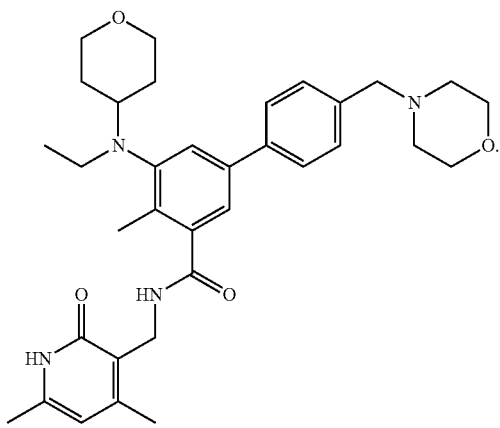 [SMILES: CCN(c1cc(-c2ccc(CN3CCOCC3)cc2)cc(C(=O)NCc2c(C)cc(C)[nH]c2=O)c1C)C1CCOCC1]

In one embodiment, the EZH2 inhibitor is GSK126, or a stereoisomer, mixture of stereoisomers, tautomer, isotopolog, or pharmaceutically acceptable salt thereof. In one embodiment, the EZH2 inhibitor is GSK126 (also known as GSK-2816126). GSK126 has a chemical name of (S)-1-(sec-butyl)-N-((4,6-dimethyl-2-oxo-1,2-dihydropyridin-3-yl)methyl)-3-methyl-6-(6-(piperazin-1-yl)pyridin-3-yl)-1H-indole-4-carboxamide, and has the structure:

In one embodiment, the EZH2 inhibitor is CPI-1205, or a stereoisomer, mixture of stereoisomers, tautomer, isotopolog, or pharmaceutically acceptable salt thereof. In one embodiment, the EZH2 inhibitor is CPI-1205. CPI-1205 has a chemical name of (R)-N-((4-methoxy-6-methyl-2-oxo-1,2-dihydropyridin-3-yl)methyl)-2-methyl-1-(1-(1-(2,2,2-trifluoroethyl)piperidin-4-yl)ethyl)-1H-indole-3-carboxamide, and has the structure:

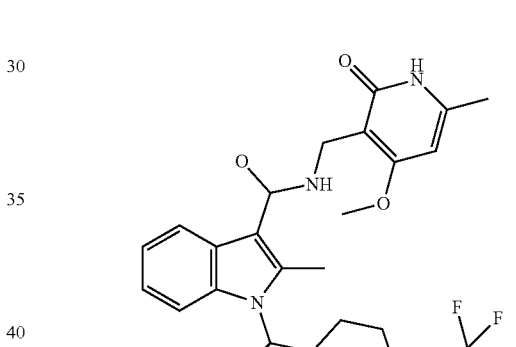

In one embodiment, the EZH2 inhibitor is 3-deazaneplanocin A. In one embodiment, the EZH2 inhibitor is EPZ005687. In one embodiment, the EZH2 inhibitor is EI1. In one embodiment, the EZH2 inhibitor is UNC1999. In one embodiment, the EZH2 inhibitor is sinefungin.

In one embodiment, the second active agent used in the methods provided herein is a bromodomain and extra-terminal motif protein (BET) inhibitor. In one embodiment, the BET inhibitor is birabresib or Compound B, or a stereoisomer, mixture of stereoisomers, tautomer, isotopolog, or pharmaceutically acceptable salt thereof.

In one embodiment, the BET inhibitor is birabresib, or a stereoisomer, mixture of stereoisomers, tautomer, isotopolog, or pharmaceutically acceptable salt thereof. In one embodiment, the BET inhibitor is birabresib. Birabresib (also known as OTX015 or MK-8628) has a chemical name of (S)-2-(4-(4-chlorophenyl)-2,3,9-trimethyl-6H-thieno[3,2-f][1,2,4]triazolo[4,3-a][1,4]diazepin-6-yl)-N-(4-hydroxyphenyl)acetamide, and has the structure:

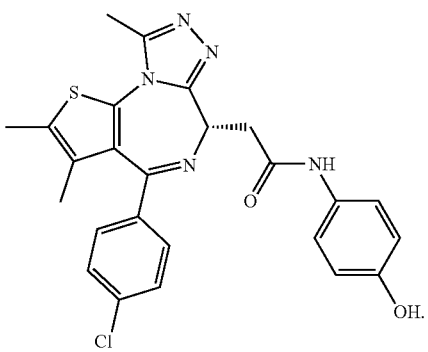 [SMILES: Cc1sc2c(c1C)C(c1ccc(Cl)cc1)=N[C@@H](CC(=O)Nc1ccc(O)cc1)c1nnc(C)n1-2]

In one embodiment, the BET inhibitor is Compound B, or a tautomer, isotopolog, or pharmaceutically acceptable salt thereof. Compound B has a chemical name of 4-[2-(cyclopropylmethoxy)-5-(methanesulfonyl)phenyl]-2-methylisoquinolin-1(2H)-one, and has the structure:

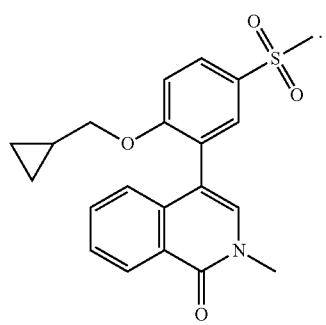 [SMILES: Cn1cc(-c2cc(S(C)(=O)=O)ccc2OCC2CC2)c2ccccc2c1=O]

In one embodiment, the BET inhibitor is BMS-986158, or a stereoisomer, mixture of stereoisomers, tautomer, isotopolog, or pharmaceutically acceptable salt thereof. In one embodiment, the BET inhibitor is BMS-986158. BMS-986158 has the structure:

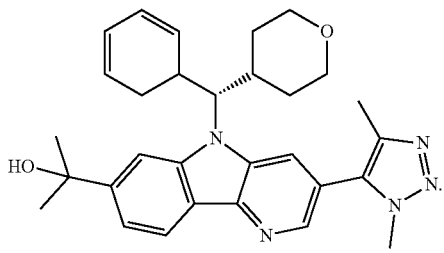 [SMILES: Cc1nnn(C)c1-c1cnc2c3ccc(C(C)(C)O)cc3n([C@H](C3C=CC=CC3)C3CCOCC3)c2c1]

In one embodiment, the BET inhibitor is RO-6870810, or a stereoisomer, mixture of stereoisomers, tautomer, isotopolog, or pharmaceutically acceptable salt thereof. In one embodiment, the BET inhibitor is RO-6870810. RO-6870810 has the structure:

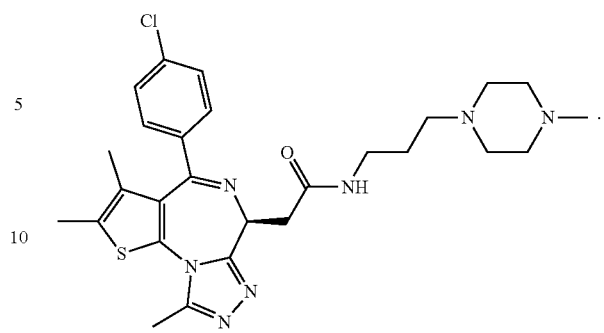

In one embodiment, the BET inhibitor is CPI-0610, or a stereoisomer, mixture of stereoisomers, tautomer, isotopolog, or pharmaceutically acceptable salt thereof. In one embodiment, the BET inhibitor is CPI-0610. CPI-0610 has the structure:

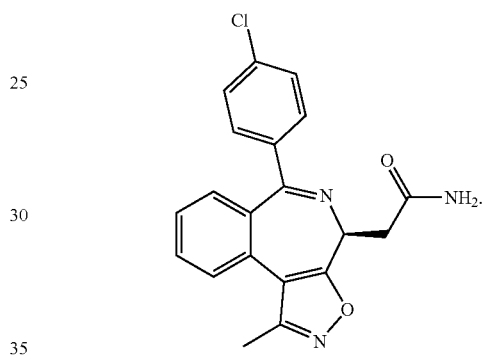

In one embodiment, the BET inhibitor is molibresib, or a stereoisomer, mixture of stereoisomers, tautomer, isotopolog, or pharmaceutically acceptable salt thereof. In one embodiment, the BET inhibitor is molibresib. Molibresib (also known as GSK-525762) has the structure:

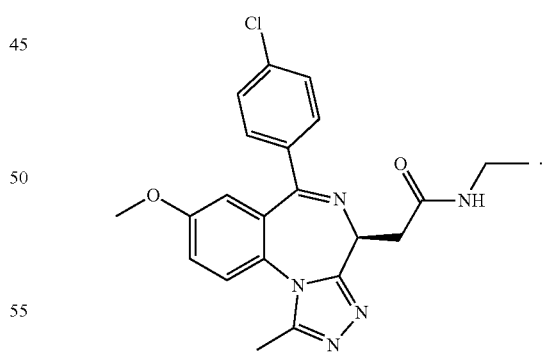

In one embodiment, the second active agent used in the methods provided herein is a hypomethylating agent. In one embodiment, the hypomethylating agent is a DNA methyltransferase inhibitor. In one embodiment, the hypomethylating agent is 5-azacytidine or decitabine, or a stereoisomer, mixture of stereoisomers, tautomer, isotopolog, or pharmaceutically acceptable salt thereof. Unless otherwise specified, the terms "azacytidine" and "azacitidine" are used interchangeably.

In one embodiment, the hypomethylating agent is 5-azacytidine, or a stereoisomer, mixture of stereoisomers, tautomer, isotopolog, or pharmaceutically acceptable salt thereof. In one embodiment, the hypomethylating agent is 5-azacytidine. 5-Azacytidine has a chemical name of 4-amino-1-β-D-ribofuranosyl-1,3,5-triazin-2(1H)-one, and has the structure:

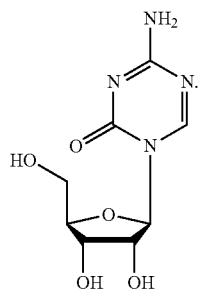

In one embodiment, the hypomethylating agent is decitabine, or a stereoisomer, mixture of stereoisomers, tautomer, isotopolog, or pharmaceutically acceptable salt thereof. In one embodiment, the hypomethylating agent is decitabine. Decitabine has a chemical name of 4-amino-1-(2-deoxy-β-D-erythro-pentofuranosyl)-1,3,5-triazin-2(1H)-one, and has the structure:

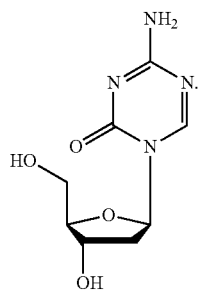

In one embodiment, the second active agent used in the methods provided herein is a disruptor of telomeric silencing 1-like (DOT1L) inhibitor. In one embodiment, the DOT1L inhibitor is pinometostat, or a stereoisomer, mixture of stereoisomers, tautomer, isotopolog, or pharmaceutically acceptable salt thereof. In one embodiment, the DOT1L inhibitor is pinometostat. Pinometostat (also known as EPZ-5676) has a chemical name of (2R,3R,4S,5R)-2-(6-amino-9H-purin-9-yl)-5-((((1r,3S)-3-(2-(5-(tert-butyl)-1H-benzo[d]imidazol-2-yl)ethyl)cyclobutyl)(isopropyl)amino)methyl)tetrahydrofuran-3,4-diol, and has the structure:

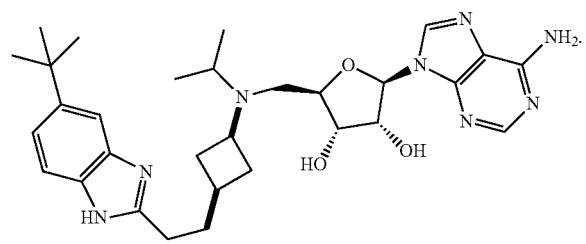

In one embodiment, the DOT1L inhibitor is SGC0946, or a stereoisomer, mixture of stereoisomers, tautomer, isotopolog, or pharmaceutically acceptable salt thereof. In one embodiment, the DOT1L inhibitor is SGC0946. SGC0946 has a chemical name of 5 bromo-7-[5-deoxy-5-[[3-[[[[4-(1,1-dimethylethyl)phenyl]amino]carbonyl]amino]propyl](1-methylethyl)amino]-β-D-ribofuranosyl]-7H-pyrrolo[2,3-d]pyrimidin-4-amine, and has the structure:

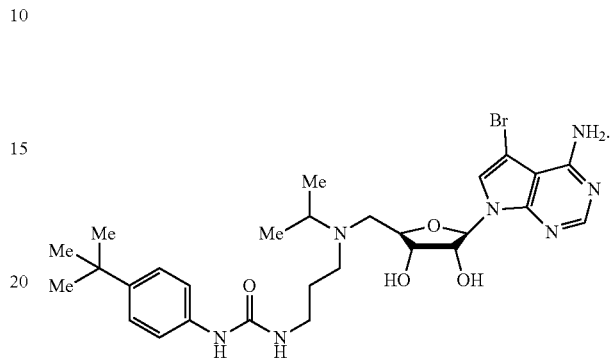

In one embodiment, the second active agent used in the methods provided herein is a histone acetyltransferase (HAT) inhibitor. In one embodiment, the HAT inhibitor is C646, or a tautomer, isotopolog, or pharmaceutically acceptable salt thereof. In one embodiment, the HAT inhibitor is C646. C646 has a chemical name of 4-(4-((5-(4,5-dimethyl-2-nitrophenyl)furan-2-yl)methylene)-3-methyl-5-oxo-4,5-dihydro-1H-pyrazol-1-yl)benzoic acid, and has the structure.

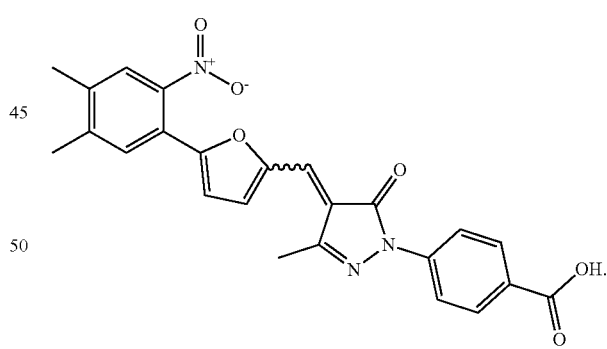

In one embodiment, the second active agent used in the methods provided herein is a WD repeat-containing protein 5 (WDR5) inhibitor. In one embodiment, the WDR5 inhibitor is OICR-9429, or a tautomer, isotopolog, or pharmaceutically acceptable salt thereof. In one embodiment, the WDR5 inhibitor is OICR-9429. OICR-9429 has a chemical name of N-(4-(4-methylpiperazin-1-yl)-3'-(morpholinomethyl)-[1,1'-biphenyl]-3-yl)-6-oxo-4-(trifluoromethyl)-1,6-dihydropyridine-3-carboxamide, and has the structure:

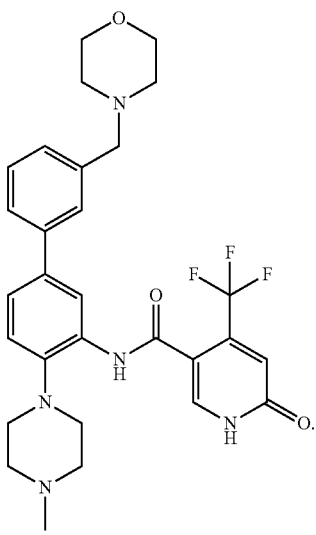 [SMILES: CN1CCN(c2ccc(-c3cccc(CN4CCOCC4)c3)cc2NC(=O)c2c[nH]c(=O)cc2C(F)(F)F)CC1]

In one embodiment, the second active agent used in the methods provided herein is a DNA (cytosine-5)-methyltransferase 1 (DNMT1) inhibitor. In one embodiment, the DNMT1 inhibitor is a DNMT1 selective inhibitor. In one embodiment, the DNMT1 selective inhibitor is GSK3484862, or a stereoisomer, mixture of stereoisomers, tautomer, isotopolog, or pharmaceutically acceptable salt thereof. In one embodiment, the DNMT1 selective inhibitor is GSK3484862. GSK3484862 (also known as GSKMI-714) has a chemical name of (R)-2-((3,5-dicyano-6-(dimethylamino)-4-ethylpyridin-2-yl)thio)-2-phenylacetamide, and has the structure:

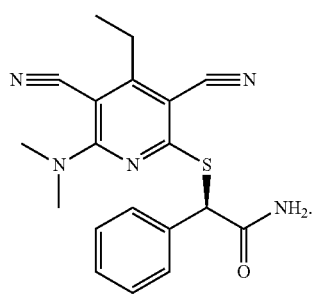 [SMILES: CCc1c(C#N)c(S[C@@H](C(N)=O)c2ccccc2)nc(N(C)C)c1C#N]

In one embodiment, the second active agent used in the methods provided herein is a lysine-specific demethylase 1 (LSD-1) inhibitor. In one embodiment, the LSD-1 inhibitor is Compound C or seclidemstat, or a tautomer, isotopolog, or pharmaceutically acceptable salt thereof.

In one embodiment, the LSD-1 inhibitor is Compound C, or a tautomer, isotopolog, or pharmaceutically acceptable salt thereof. In one embodiment, the LSD-1 inhibitor is Compound C. In one embodiment, the LSD-1 inhibitor is a pharmaceutically acceptable salt of Compound C. In one embodiment, the LSD-1 inhibitor is Compound C besylate. In one embodiment, the LSD-1 inhibitor is Compound C mono-besylate. Compound C has a chemical name of 4-(2-(4-aminopiperidin-1-yl)-5-(3-fluoro-4-methoxyphenyl)-1-methyl-6-oxo-1,6-dihydropyrimidin-4-yl)-2-fluorobenzonitrile, and has the structure:

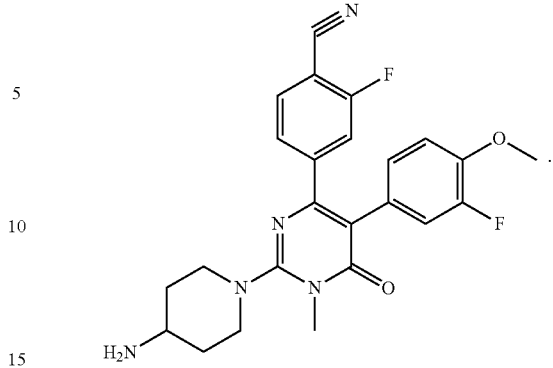

In one embodiment, the LSD-1 inhibitor is seclidemstat, or a tautomer, isotopolog, or pharmaceutically acceptable salt thereof. In one embodiment, the LSD-1 inhibitor is seclidemstat. In one embodiment, the LSD-1 inhibitor is a pharmaceutically acceptable salt of seclidemstat. In one embodiment, the LSD-1 inhibitor is seclidemstat mesylate. Seclidemstat (also known as SP-2577) has a chemical name of (E)-N'-(1-(5-chloro-2-hydroxyphenyl)ethylidene)-3-((4-methylpiperazin-1-yl)sulfonyl)benzohydrazide, and has the structure:

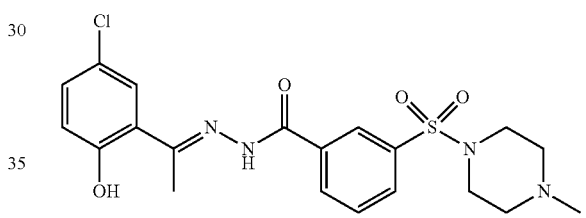

In one embodiment, the second active agent used in the methods provided herein is a G9A (one of the histone H3 methyltransferases) inhibitor. In one embodiment, the G9A inhibitor is UNC0631, or a tautomer, isotopolog, or pharmaceutically acceptable salt thereof. In one embodiment, the G9A inhibitor is UNC0631. UNC0631 has a chemical name of N-(1-(cyclohexylmethyl)piperidin-4-yl)-2-(4-isopropyl-1,4-diazepan-1-yl)-6-methoxy-7-(3-(piperidin-1-yl)propoxy)quinazolin-4-amine, and has the structure:

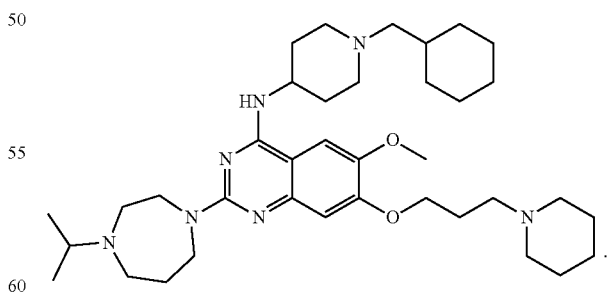

In one embodiment, the second active agent used in the methods provided herein is a protein arginine methyltransferase 5 (PRMT5) inhibitor. In one embodiment, the PRMT5 inhibitor is GSK3326595, or a stereoisomer, mixture of stereoisomers, tautomer, isotopolog, or pharmaceutically acceptable salt thereof. In one embodiment, the PRMT5 inhibitor is GSK3326595. GSK3326595 (also known as EPZ-015938) has a chemical name of (S)-6-((1-acetylpiperidin-4-yl)amino)-N-(3-(3,4-dihydroisoquinolin-2(1H)-yl)-2-hydroxypropyl)pyrimidine-4-carboxamide, and has the structure:

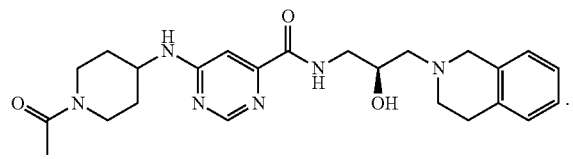 [SMILES: CC(=O)N1CCC(Nc2cc(C(=O)NC[C@H](O)CN3CCc4ccccc4C3)ncn2)CC1]

In one embodiment, the second active agent used in the methods provided herein is a bromodomain (BRD) inhibitor. In one embodiment, the BRD inhibitor is a BRD9/7 inhibitor. In one embodiment, the BRD9/7 inhibitor is LP99, or a stereoisomer, mixture of stereoisomers, tautomer, isotopolog, or pharmaceutically acceptable salt thereof. In one embodiment, the BRD9/7 inhibitor is LP99. LP99 has a chemical name of N-((2R,3S)-2-(4-chlorophenyl)-1-(1,4-dimethyl-2-oxo-1,2-dihydroquinolin-7-yl)-6-oxopiperidin-3-yl)-2-methylpropane-1-sulfonamide, and has the structure:

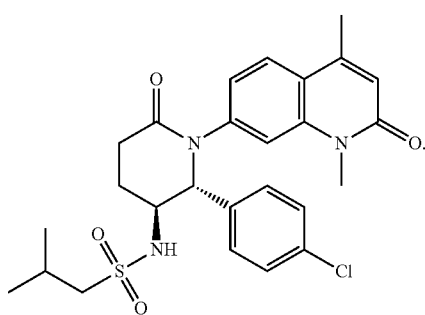 [SMILES: Cc1cc(=O)n(C)c2cc(N3C(=O)CC[C@H](NS(=O)(=O)CC(C)C)[C@H]3c3ccc(Cl)cc3)ccc12]

In one embodiment, the BRD inhibitor is a BRD4 inhibitor. In one embodiment, the BRD4 inhibitor is JQ1, or a stereoisomer, mixture of stereoisomers, tautomer, isotopolog, or pharmaceutically acceptable salt thereof. In one embodiment, the BRD4 inhibitor is JQ1. JQ1 has a chemical name of (S)-tert-butyl 2-(4-(4-chlorophenyl)-2,3,9-trimethyl-6H-thieno[3,2-f][1,2,4]triazolo[4,3-a][1,4]diazepin-6-yl)acetate, and has the structure:

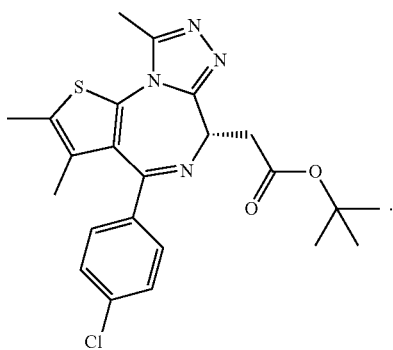 [SMILES: Cc1sc2c(c1C)C(c1ccc(Cl)cc1)=N[C@@H](CC(=O)OC(C)(C)C)c1nnc(C)n1-2]

In one embodiment, the second active agent used in the methods provided herein is a SUV420H1/H2 (two homologous enzymes that methylate lysine 20 of histone H4) inhibitor. In one embodiment, the SUV420H1/H2 inhibitor is A-196, or a tautomer, isotopolog, or pharmaceutically acceptable salt thereof. In one embodiment, the SUV420H1/H2 inhibitor is A-196. A-196 has a chemical name of 6,7-dichloro-N-cyclopentyl-4-(pyridin-4-yl)phthalazin-1-amine, and has the structure:

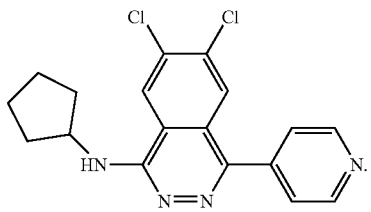 [SMILES: Clc1cc2c(NC3CCCC3)nnc(-c3ccncc3)c2cc1Cl]

In one embodiment, the second active agent used in the methods provided herein is a coactivator-associated arginine methyltransferase 1 (CARM1) inhibitor. In one embodiment, the CARM1 inhibitor is EZM2302, or a stereoisomer, mixture of stereoisomers, tautomer, isotopolog, or pharmaceutically acceptable salt thereof. In one embodiment, the CARM1 inhibitor is EZM2302. EZM2302 has a chemical name of methyl (R)-2-(2-(2-chloro-5-(2-hydroxy-3-(methylamino)propoxy)phenyl)-6-(3,5-dimethylisoxazol-4-yl)-5-methylpyrimidin-4-yl)-2,7-diazaspiro[3.5]nonane-7-carboxylate, and has the structure:

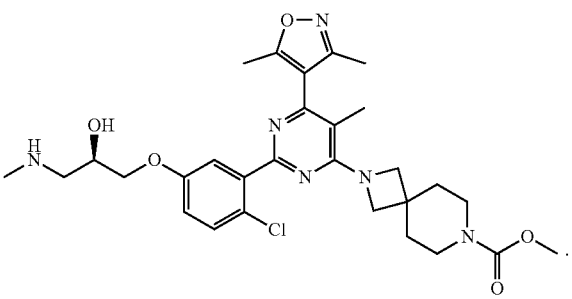

In one embodiment, the second active agent used in the methods provided herein is a polo-like kinase 1 (PLK1) inhibitor. In one embodiment, the PLK1 inhibitor is BI2536, or a stereoisomer, mixture of stereoisomers, tautomer, isotopolog, or pharmaceutically acceptable salt thereof. In one embodiment, the PLK1 inhibitor is BI2536. BI2536 has a chemical name of (R)-4-((8-cyclopentyl-7-ethyl-5-methyl-6-oxo-5,6,7,8-tetrahydropteridin-2-yl)amino)-3-methoxy-N-(1-methylpiperidin-4-yl)benzamide, and has the structure:

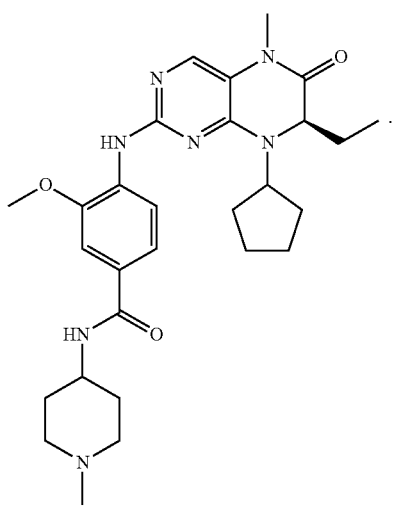 [SMILES: CC[C@@H]1C(=O)N(C)c2cnc(Nc3ccc(C(=O)NC4CCN(C)CC4)cc3OC)nc2N1C1CCCC1]

In one embodiment, the PLK1 inhibitor is volasertib, or a stereoisomer, mixture of stereoisomers, tautomer, isotopolog, or pharmaceutically acceptable salt thereof. In one embodiment, the PLK1 inhibitor is volasertib. Volasertib (also known as BI6727) has the structure:

In one embodiment, the PLK1 inhibitor is CYC140, or a stereoisomer, mixture of stereoisomers, tautomer, isotopolog, or pharmaceutically acceptable salt thereof.

In one embodiment, the PLK1 inhibitor is onvansertib, or a tautomer, isotopolog, or pharmaceutically acceptable salt thereof. In one embodiment, the PLK1 inhibitor is onvansertib. Onvansertib (also known as NMS-1286937) has the structure:

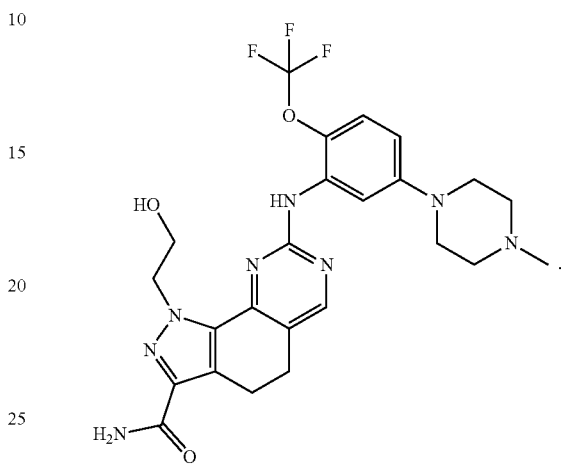

In one embodiment, the PLK1 inhibitor is GSK461364, or a stereoisomer, mixture of stereoisomers, tautomer, isotopolog, or pharmaceutically acceptable salt thereof. In one embodiment, the PLK1 inhibitor is GSK461364. GSK461364 has the structure:

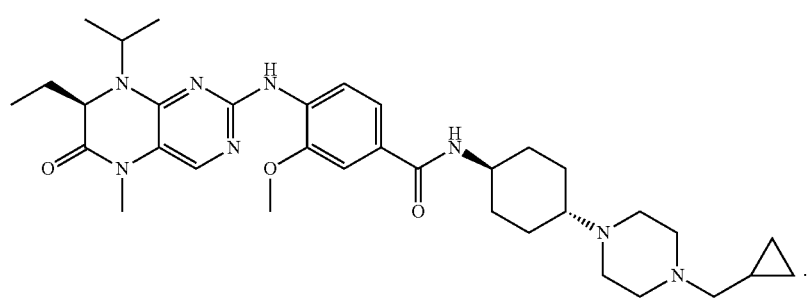 [SMILES: CC[C@@H]1C(=O)N(C)c2cnc(Nc3ccc(C(=O)N[C@H]4CC[C@H](N5CCN(CC6CC6)CC5)CC4)cc3OC)nc2N1C(C)C]

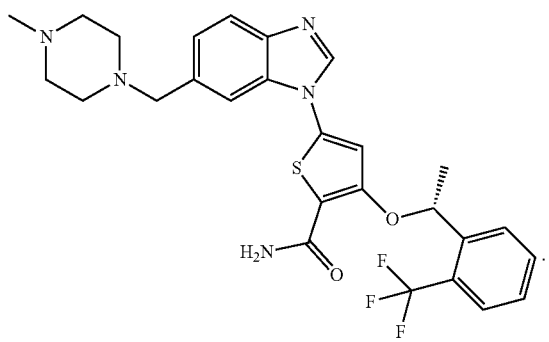 [SMILES: C[C@@H](Oc1cc(-n2cnc3ccc(CN4CCN(C)CC4)cc32)sc1C(N)=O)c1ccccc1C(F)(F)F]

In one embodiment, the PLK1 inhibitor is TAK960, or a tautomer, isotopolog, or pharmaceutically acceptable salt thereof. In one embodiment, the PLK1 inhibitor is TAK960. In one embodiment, the PLK1 inhibitor is a hydrochloride salt of TAK960. TAK960 has the structure:

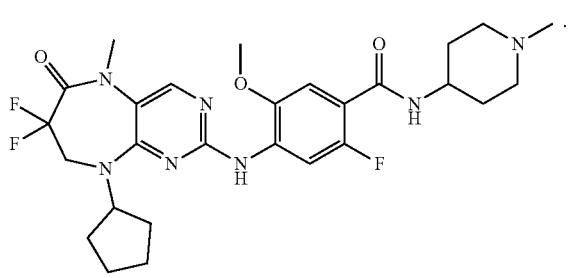 [SMILES: COc1cc(C(=O)NC2CCN(C)CC2)c(F)cc1Nc1ncc2c(n1)N(C1CCCC1)CC(F)(F)C(=O)N2C]

In one embodiment, the second active agent used in the methods provided herein is a serine/threonine-protein kinase (NEK2) inhibitor. In one embodiment, the NEK2 inhibitor is JH295, or a tautomer, isotopolog, or pharmaceutically acceptable salt thereof. In one embodiment, the NEK2 inhibitor is JH295. JH295 has a chemical name of (Z)—N-(3-((2-ethyl-4-methyl-1H-imidazol-5-yl)methylene)-2-oxoindolin-5-yl)propiolamide, and has the structure:

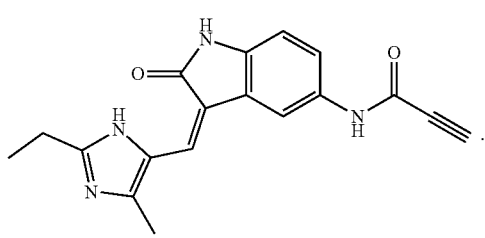 [SMILES: C#CC(=O)Nc1ccc2c(c1)/C(=C/c1[nH]c(CC)nc1C)C(=O)N2]

In one embodiment, the NEK2 inhibitor is rac-CCT 250863, or a stereoisomer, mixture of stereoisomers, tautomer, isotopolog, or pharmaceutically acceptable salt thereof. In one embodiment, the NEK2 inhibitor is rac-CCT 250863. Rac-CCT 250863 has a chemical name of 4-[2-amino-5-[4-[(dimethylamino)methyl]-2-thienyl]-3-pyridinyl]-2-[[(2Z)-4,4,4-trifluoro-1-methyl-2-buten-1-yl]oxy]benzamide, and has the structure:

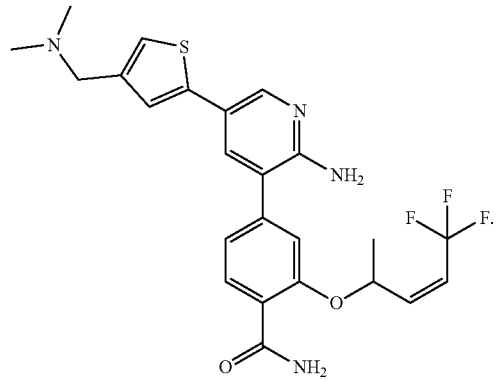 [SMILES: CC(/C=C\C(F)(F)F)Oc1cc(-c2cc(-c3cc(CN(C)C)cs3)cnc2N)ccc1C(N)=O]

In one embodiment, the second active agent used in the methods provided herein is a mitogen-activated extracellular signal-regulated kinase (MEK) inhibitor. In one embodiment, the MEK inhibitor interrupts the function of the RAF/RAS/MEK signal transduction cascade. In one embodiment, the MEK inhibitor is trametinib, trametinib dimethyl sulfoxide, cobimetinib, binimetinib, or selumetinib, or a stereoisomer, mixture of stereoisomers, tautomer, isotopolog, or pharmaceutically acceptable salt thereof. In one embodiment, the MEK inhibitor is trametinib or trametinib dimethyl sulfoxide, or a stereoisomer, mixture of stereoisomers, tautomer, isotopolog, or pharmaceutically acceptable salt thereof. In one embodiment, the MEK inhibitor is trametinib. In one embodiment, the MEK inhibitor is trametinib dimethyl sulfoxide. In one embodiment, the MEK inhibitor is cobimetinib. In one embodiment, the MEK inhibitor is binimetinib. In one embodiment, the MEK inhibitor is selumetinib. Trametinib dimethyl sulfoxide has a chemical name of N-[3-[3-cyclopropyl-5-[(2-fluoro-4-iodophenyl)amino]-3,4,6,7-tetrahydro-6,8-dimethyl-2,4,7-trioxopyrido[4,3-d]pyrimidin-1(2H)-yl]phenyl]-acetamide, compound with dimethyl sulfoxide (1:1). Trametinib dimethyl sulfoxide has the structure:

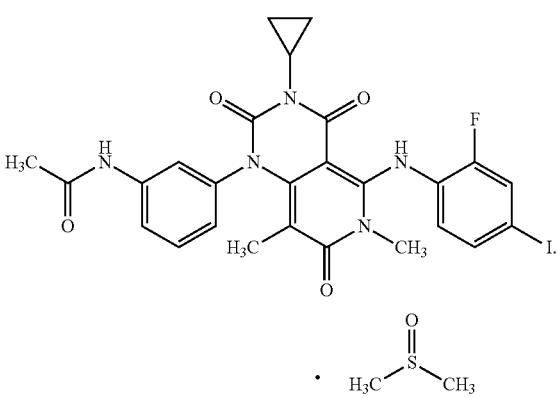

In one embodiment, the second active agent used in the methods provided herein is a PHD Finger Protein 19 (PHF19) inhibitor.

In one embodiment, the second active agent used in the methods provided herein is a proviral integration site for Moloney murine leukemia kinase (PIM) inhibitor. In one embodiment, the PIM inhibitor is a pan-PIM inhibitor. In one embodiment, the PIM inhibitor is LGH-447, AZD1208, SGI-1776, or TP-3654, or a stereoisomer, mixture of stereoisomers, tautomer, isotopolog, or pharmaceutically acceptable salt thereof. In one embodiment, the PIM inhibitor is LGH-447, or a stereoisomer, mixture of stereoisomers, tautomer, isotopolog, or pharmaceutically acceptable salt thereof. In one embodiment, the PIM inhibitor is LGH-447. In one embodiment, the PIM inhibitor is a pharmaceutically acceptable salt of LGH-447. In one embodiment, the PIM inhibitor is a hydrochloride salt of LGH-447. In one embodiment, the hydrochloride salt of LGH-447 is a di-hydrochloride salt. In one embodiment, the hydrochloride salt of LGH-447 is a mono-hydrochloride salt. In one embodiment, the PIM inhibitor is AZD1208. In one embodiment, the PIM inhibitor is SGI-1776. In one embodiment, the PIM inhibitor is TP-3654. LGH-447 has a chemical name of N-[4-[(1R, 3S,5S)-3-amino-5-methylcyclohexyl]-3-pyridinyl]-6-(2,6-difluorophenyl)-5-fluoro-2-pyridinecarboxamide, and has the structure:

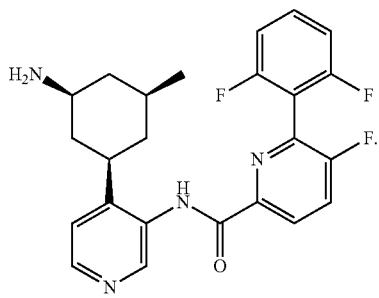 [SMILES: C[C@@H]1C[C@H](N)C[C@H](c2ccncc2NC(=O)c2ccc(F)c(-c3c(F)cccc3F)n2)C1]

In one embodiment, the second active agent used in the methods provided herein is an insulin-like growth factor 1 receptor (IGF-1R) inhibitor. In one embodiment, the IGF-1R inhibitor is linsitinib, or a stereoisomer, mixture of stereoisomers, tautomer, isotopolog, or pharmaceutically acceptable salt thereof. In one embodiment, the IGF-1R inhibitor is linsitinib. Linsitinib has a chemical name of cis-3-[8-amino-1-(2-phenyl-7-quinolinyl)imidazo[1,5-a]pyrazin-3-yl]-1-methylcyclobutanol, and has the structure:

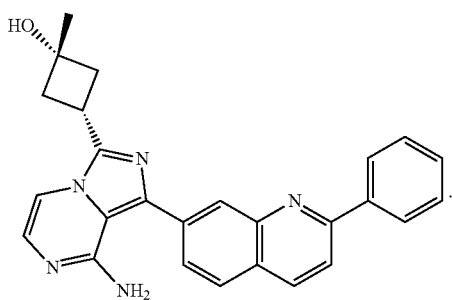 [SMILES: C[C@]1(O)C[C@@H](c2nc(-c3ccc4ccc(-c5ccccc5)nc4c3)c3c(N)nccn32)C1]

In one embodiment, the second active agent used in the methods provided herein is an exportin 1 (XPO1) inhibitor. In one embodiment, the XPO1 inhibitor is selinexor, or a stereoisomer, mixture of stereoisomers, tautomer, isotopolog, or pharmaceutically acceptable salt thereof. In one embodiment, the XPO1 inhibitor is selinexor. Selinexor has a chemical name of (2Z)-3-{3-[3,5-bis(trifluoromethyl)phenyl]-1H-1,2,4-triazol-1-yl}-N'-(pyrazin-2-yl)prop-2-enehydrazide, and has the structure:

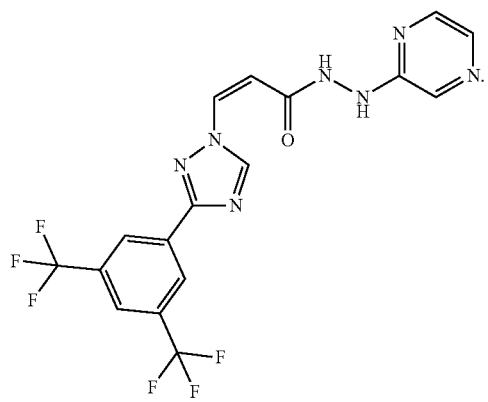 [SMILES: O=C(/C=C\n1cnc(-c2cc(C(F)(F)F)cc(C(F)(F)F)c2)n1)NNc1cnccn1]

In one embodiment, the second active agent used in the methods provided herein is a survivin (also called baculoviral inhibitor of apoptosis repeat-containing 5 or BIRC5) inhibitor. In one embodiment, the BIRC5 inhibitor is YM155, or a tautomer, isotopolog, or pharmaceutically acceptable salt thereof. In one embodiment, the BIRC5 inhibitor is YM155. YM155 has a chemical name of 1-(2-methoxyethyl)-2-methyl-4,9-dioxo-3-(pyrazin-2-ylmethyl)-4,9-dihydro-1H-naphtho[2,3-d]imidazol-3-ium bromide, and has the structure:

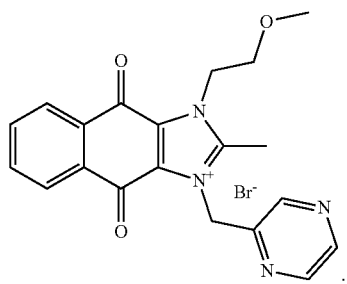 [SMILES: COCCn1c2c([n+](Cc3cnccn3)c1C)C(=O)c1ccccc1C2=O ; [Br-]]

In one embodiment, the second active agent used in the methods provided herein is a chemotherapy. In one embodiment, the chemotherapy is bendamustine, doxorubicin, etoposide, methotrexate, cytarabine, vincristine, ifosfamide, melphalan, oxaliplatin, or dexamethasone, or a stereoisomer, mixture of stereoisomers, tautomer, isotopolog, prodrug, or pharmaceutically acceptable salt thereof.

In one embodiment, the chemotherapy is bendamustine, or a tautomer, isotopolog, or pharmaceutically acceptable salt thereof. In one embodiment, the chemotherapy is bendamustine. In one embodiment, the chemotherapy is a pharmaceutically acceptable salt of bendamustine. In one embodiment, the chemotherapy is bendamustine hydrochloride. In one embodiment, the chemotherapy is a mono-hydrochloride salt of bendamustine. Bendamustine has a chemical name of 4-(5-(bis(2-chloroethyl)amino)-1-methyl-H-benzo[d]imidazol-2-yl)butanoic acid, and has the structure:

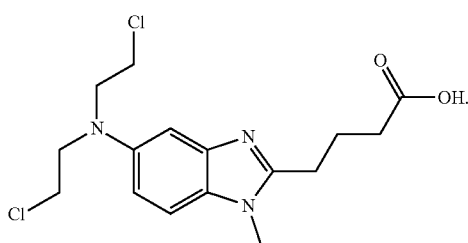

In one embodiment, the chemotherapy is doxorubicin, or a stereoisomer, mixture of stereoisomers, tautomer, isotopolog, or pharmaceutically acceptable salt thereof. In one embodiment, the chemotherapy is doxorubicin. In one embodiment, the chemotherapy is a pharmaceutically acceptable salt of doxorubicin. In one embodiment, the chemotherapy is doxorubicin hydrochloride. In one embodiment, the chemotherapy is a mono-hydrochloride salt of doxorubicin. Doxorubicin has the structure:

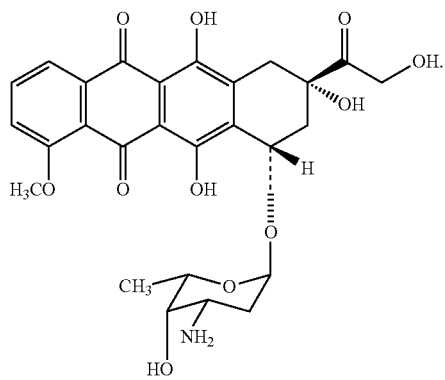

In one embodiment, the chemotherapy is etoposide, or a stereoisomer, mixture of stereoisomers, tautomer, isotopolog, prodrug, or pharmaceutically acceptable salt thereof. In embodiment, the chemotherapy is etoposide. Etoposide has a chemical name of 4'-demethylepipodophyllotoxin 9-[4,6-β-(R)-ethylidene-β-D-glucopyranoside], and has the structure: 1

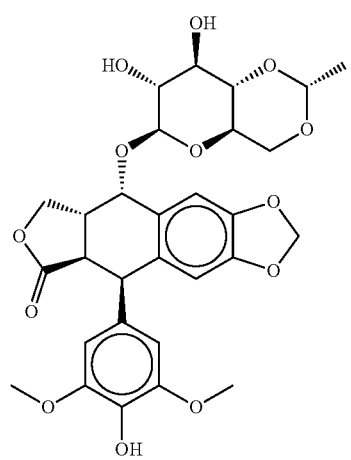

In one embodiment, the chemotherapy is a prodrug of etoposide. In one embodiment, the chemotherapy is an ester prodrug of etoposide. In one embodiment, the chemotherapy is etoposide phosphate. Etoposide phosphate has a chemical name of 4'-demethylepipodophyllotoxin 9-[4,6-β-(R)-ethylidene-β-D-glucopyranoside], 4' (dihydrogen phosphate), and has the structure:

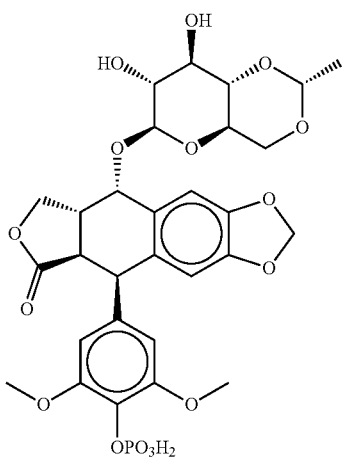

In one embodiment, the chemotherapy is methotrexate, or a stereoisomer, mixture of stereoisomers, tautomer, isotopolog, or pharmaceutically acceptable salt thereof. In one embodiment, the chemotherapy is methotrexate. In one embodiment, the chemotherapy is a pharmaceutically acceptable salt of methotrexate. In one embodiment, the chemotherapy is methotrexate sodium. Methotrexate has a chemical name of (4-(((2,4-diaminopteridin-6-yl)methyl) (methyl)amino)benzoyl)-L-glutamic acid, and has the structure:

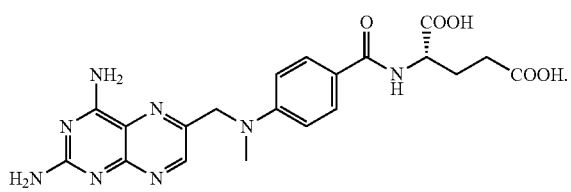 [SMILES: CN(Cc1cnc2nc(N)nc(N)c2n1)c1ccc(C(=O)N[C@@H](CCC(=O)O)C(=O)O)cc1]

In one embodiment, the chemotherapy is cytarabine, or a stereoisomer, mixture of stereoisomers, tautomer, isotopolog, or pharmaceutically acceptable salt thereof. In one embodiment, the chemotherapy is cytarabine. Cytarabine has a chemical name of 4-amino-1-β-D-arabinofuranosyl-2 (1H)pyrimidinone, and has the structure:

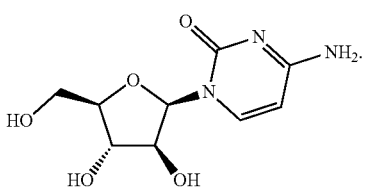 [SMILES: Nc1ccn([C@@H]2O[C@H](CO)[C@@H](O)[C@@H]2O)c(=O)n1]

In one embodiment, the chemotherapy is vincristine, or a stereoisomer, mixture of stereoisomers, tautomer, isotopolog, or pharmaceutically acceptable salt thereof. In one embodiment, the chemotherapy is vincristine. In one embodiment, the chemotherapy is a pharmaceutically acceptable salt of vincristine. In one embodiment, the chemotherapy is vincristine sulfate. In one embodiment, the chemotherapy is a mono-sulfate salt of vincristine. Vincristine has the structure:

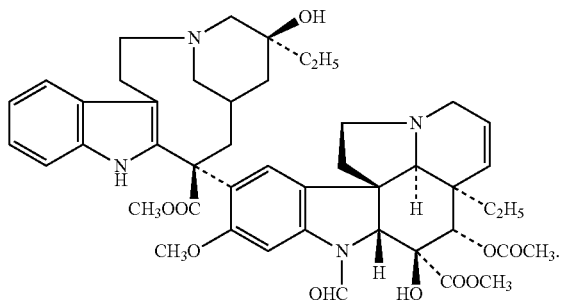

In one embodiment, the chemotherapy is ifosfamide, or a tautomer, isotopolog, or pharmaceutically acceptable salt thereof. In one embodiment, the chemotherapy is ifosfamide. Ifosfamide has a chemical name of 3-(2-chloroethyl)-2-[(2-chloroethyl)amino]tetrahydro-2H-1,3,2-oxazaphosphorine 2-oxide, and has the structure:

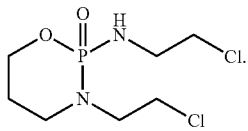 [SMILES: O=P1(NCCCl)OCCCN1CCCl]

In one embodiment, the chemotherapy is melphalan, or a stereoisomer, mixture of stereoisomers, tautomer, isotopolog, or pharmaceutically acceptable salt thereof. In one embodiment, the chemotherapy is melphalan. In one embodiment, the chemotherapy is a pharmaceutically acceptable salt of melphalan. In one embodiment, the chemotherapy is melphalan hydrochloride. In one embodiment, the chemotherapy is a mono-hydrochloride salt of melphalan. Melphalan has a chemical name of 4-[bis(2-chloroethyl)amino]-L-phenylalanine, and has the structure:

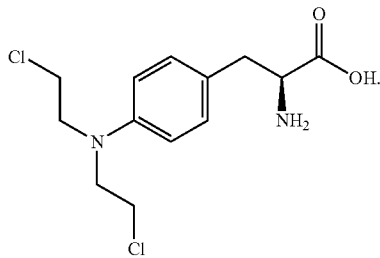 [SMILES: N[C@@H](Cc1ccc(N(CCCl)CCCl)cc1)C(=O)O]

In one embodiment, the chemotherapy is oxaliplatin, or a stereoisomer, mixture of stereoisomers, tautomer, isotopolog, or pharmaceutically acceptable salt thereof. In one embodiment, the chemotherapy is oxaliplatin. Oxaliplatin has a chemical name of cis-[(1R,2R)-1,2cyclohexanediamine-N,N'][oxalato(2-)-O,O']platinum, and has the structure:

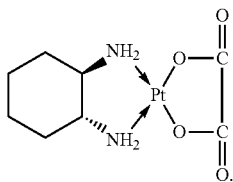

In one embodiment, the chemotherapy is dexamethasone, or a stereoisomer, mixture of stereoisomers, tautomer, isotopolog, or pharmaceutically acceptable salt thereof. In one embodiment, the chemotherapy is dexamethasone. Dexamethasone has a chemical name of (11b,16a)-9-fluoro-11,17,21-trihydroxy-16-methylpregna-1,4-diene-3,20-dione, and has the structure:

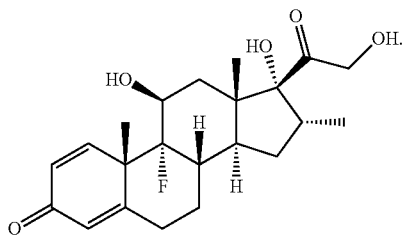

5.4 Methods of Use

In one embodiment, provided herein is a method of treating a hematological malignancy, which comprises administering to a patient a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). Also provided herein is Compound A for use in a method of treating a hematological malignancy, wherein the method comprises administering to a patient a therapeutically effective amount of Compound A, in combination with a second active agent provided herein.

In one embodiment, provided herein is a method of preventing a hematological malignancy, which comprises administering to a patient a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). Also provided herein is Compound A for use in a method of preventing a hematological malignancy, wherein the method comprises administering to a patient a therapeutically effective amount of Compound A, in combination with a second active agent provided herein.

In one embodiment, provided herein is a method of managing a hematological malignancy, which comprises administering to a patient a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). Also provided herein is Compound A for use in a method of managing a hematological malignancy, wherein the method comprises administering to a patient a therapeutically effective amount of Compound A, in combination with a second active agent provided herein.

In one embodiment, the hematological malignancy is leukemia.

In one embodiment, the hematological malignancy is acute myeloid leukemia. In one embodiment, the acute myeloid leukemia is B-cell acute myeloid leukemia.

In one embodiment, the hematological malignancy is acute lymphocytic leukemia.

In one embodiment, the hematological malignancy is chronic lymphocytic leukemia/small lymphocytic lymphoma.

In one embodiment, the hematological malignancy is myeloma.

In one embodiment, the hematological malignancy is multiple myeloma. In one embodiment, the multiple myeloma is plasma cell leukemia (PCL).

In one embodiment, the hematological malignancy is lymphoma.

In one embodiment, the hematological malignancy is non-Hodgkin's lymphoma.

In one embodiment, the hematological malignancy is diffuse large B-cell lymphoma.

In one embodiment, the hematological malignancy is T-cell lymphoma. In one embodiment, the T-cell lymphoma is anaplastic large cell lymphoma (ALCL). In one embodiment, the T-cell lymphoma is Sezary Syndrome.

In one embodiment, the hematological malignancy is Burkitt lymphoma.

In one embodiment, the hematological malignancy is marginal zone lymphoma. In one embodiment, the marginal zone lymphoma is splenic marginal zone lymphoma (SMZL).

In one embodiment, the hematological malignancy is Hodgkin's lymphoma.

In one embodiment, the hematological malignancy is myelodysplastic syndromes.

In one embodiment, the DLBCL is activated B-cell-like DLBCL (ABC-DLBCL). In one embodiment, the DLBCL is germinal center B-cell-like DLBCL (GCB-DLBCL). In one embodiment, the DLBCL is unclassified DLBCL. In one embodiment, the DLBCL is primary mediastinal B-cell type DLBCL (PMBL DLBCL). In one embodiment, the DLBCL is double-hit DLBCL (DHIT DLBCL), also referred to as cMyc/Bcl-2 mutant DLBCL. In one embodiment, the DLBCL is triple-hit DLBCL (THIT DLBCL) also referred to as cMyc/Bcl2/Bcl6 rearrangement DLBCL.

In one embodiment, the DLBCL is newly diagnosed DLBCL. In one embodiment, the DLBCL is primary DLBCL. In one embodiment, the DLBCL is relapsed DLBCL. In one embodiment, the DLBCL is refractory DLBCL. In one embodiment, the DLBCL is relapsed or refractory DLBCL. In one embodiment, the DLBCL is relapsed/refractory DLBCL. In one embodiment, the DLBCL is refractory to doxorubicin. In one embodiment, the DLBCL is resistant to doxorubicin. In one embodiment, the DLBCL is refractory to one or more of rituximab, cyclophosphamide, doxorubicin, vincristine, prednisone, etoposide, bendamustine, lenalidomide, gemcitabine, dexamethasone, ifosfamide, polatuxuab, or CAR-T.

In one embodiment, the DLBCL is treated with two or more prior lines of treatment.

In one embodiment, the DLBCL is transformed lymphoma. In another embodiment, the DLBCL is not otherwise specified (NOS) DLBCL.

As used herein and unless otherwise indicated, "CLL/SLL" or "CLL and/or SLL" means CLL, or SLL, or CLL and SLL. In one embodiment, the methods provided herein are for treating, preventing or managing CLL. In one embodiment, the methods provided herein are for treating, preventing or managing SLL. In one embodiment, the methods provided herein are for treating, preventing or managing CLL and CLL.

In one embodiment, the CLL/SLL subject has failed one or more lines of therapy. In one embodiment, the subject has failed at least one prior therapy. In one embodiment, the subject has failed at least two prior therapies. In one embodiment, the subject has been previously treated with a Bruton's tyrosine kinase (BTK) inhibitor. In one embodiment, the subject is relapsed or refractory to a BTK inhibitor. In one embodiment, the BTK inhibitor is ibrutinib. In one embodiment, the BTK inhibitor is acalabrutinib. In one embodiment, the BTK inhibitor is zanubrutinib. In one embodiment, the BTK inhibitor is tirabrutinib.

In one embodiment, the CLL/SLL is newly diagnosed CLL/SLL. In one embodiment, the CLL/SLL is relapsed or refractory CLL/SLL (R/R CLL/SLL).

In one embodiment, the CLL is characterized by mutated IGHV (Immunoglobulin Heavy Chain Gene). In one embodiment, the CLL is characterized by non-mutated IGHV.

In one embodiment, the CLL is characterized by one or more mutations in TP53 (Tumor Protein 53). In one embodiment, the CLL is characterized by wild type TP53.

In one embodiment, the CLL is characterized by one or more cytogenetic abnormalities, e.g., del(13q), del(11q), del(17p), tri12, t(6;17), del(11q22.3), t(11;14), del(18q), and t(14;19). In one embodiment, the CLL is characterized by del(17p).

In one embodiment, the CLL is characterized by Richter's Transformation (also known as Richter's Syndrome).

In one embodiment, the hematological malignancy is newly diagnosed. In one embodiment, the hematological malignancy is relapsed or refractory.

In one embodiment, the AML is newly diagnosed AML. In one embodiment, the AML is relapsed or refractory AML. In one embodiment, the B-cell AML is newly diagnosed B-cell AML. In one embodiment, the B-cell AML is relapsed or refractory B-cell AML.

In one embodiment, the ALL is newly diagnosed ALL. In one embodiment, the ALL is relapsed or refractory ALL.

In one embodiment, the MM is newly diagnosed MM. In one embodiment, the MM is relapsed or refractory MM. In one embodiment, the PCL is newly diagnosed PCL. In one embodiment, the PCL is relapsed or refractory PCL.

In one embodiment, the HL is newly diagnosed HL. In one embodiment, the HL is relapsed or refractory HL.

In one embodiment, the NHL is newly diagnosed NHL. In one embodiment, the NHL is relapsed or refractory NHL.

In one embodiment, the TCL is newly diagnosed TCL. In one embodiment, the TCL is relapsed or refractory TCL. In one embodiment, the ALCL is newly diagnosed ALCL. In one embodiment, the ALCL is relapsed or refractory ALCL. In one embodiment, the Sezary Syndrome is newly diagnosed Sezary Syndrome. In one embodiment, the Sezary Syndrome is relapsed or refractory Sezary Syndrome.

In one embodiment, the BL is newly diagnosed BL. In one embodiment, the BL is relapsed or refractory BL.

In one embodiment, the MZL is newly diagnosed MZL. In one embodiment, the MZL is relapsed or refractory MZL. In one embodiment, the SMZL is newly diagnosed SMZL. In one embodiment, the SMZL is relapsed or refractory SMZL.

In one embodiment, the MDS is newly diagnosed MDS. In one embodiment, the MDS is relapsed or refractory MDS.

In one embodiment, provided herein are methods for achieving a complete response, partial response, or stable disease in a patient, comprising administering to a patient having a hematological malignancy provided herein a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, the hematological malignancy is AML (e.g., B-cell AML). In one embodiment, the hematological malignancy is ALL. In one embodiment, the hematological malignancy is CLL/SLL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, provided herein are methods for achieving a complete response, partial response, or stable disease, as determined by the Lugano response criteria in a patient, comprising administering to a patient having DLBCL a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone).

In one embodiment, provided herein are methods for achieving a complete response, partial response, or stable disease, as determined by the International Workshop on Chronic Lymphocytic Leukemia criteria in a patient, comprising administering to patient having CLL/SLL a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, minimal residual disease (MRD) detection may be performed in subjects who undergo bone marrow evaluation for confirmation of a complete response (CR). In one embodiment, provided herein are methods for achieving minimal residual disease (MRD) negativity in a patient, comprising administering to patient having CLL/SLL a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, the MRD negativity is measured in peripheral blood and/or bone marrow. In one embodiment, the MRD negativity lasts for a minimum of 3 months.

In one embodiment, provided herein are methods for achieving an increase in overall survival, progression-free survival, event-free survival, time to progression, or disease-free survival in a patient, comprising administering to a patient having a hematological malignancy provided herein a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, the hematological malignancy is AML (e.g., B-cell AML). In one embodiment, the hematological malignancy is ALL. In one embodiment, the hematological malignancy is CLL/SLL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, provided herein are methods for achieving an increase in overall survival in a patient, comprising administering to a patient having a hematological malignancy provided herein a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, the hematological malignancy is AML (e.g., B-cell AML). In one embodiment, the hematological malignancy is ALL. In one embodiment, the hematological malignancy is CLL/SLL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, provided herein are methods for achieving an increase in progression-free survival in a patient, comprising administering to a patient having a hematological malignancy provided herein a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, the hematological malignancy is AML (e.g., B-cell AML). In one embodiment, the hematological malignancy is ALL. In one embodiment, the hematological malignancy is CLL/SLL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, provided herein are methods for achieving an increase in event-free survival in a patient, comprising administering to a patient having a hematological malignancy provided herein a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, the hematological malignancy is AML (e.g., B-cell AML). In one embodiment, the hematological malignancy is ALL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, provided herein are methods for achieving an increase in time to progression in a patient, comprising administering to a patient having a hematological malignancy provided herein a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, the hematological malignancy is AML (e.g., B-cell AML). In one embodiment, the hematological malignancy is ALL. In one embodiment, the hematological malignancy is CLL/SLL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, provided herein are methods for achieving an increase in disease-free survival in a patient, comprising administering to a patient having a hematological malignancy provided herein a therapeutically effective amount of Compound A, in combination with a second active agent, wherein the second active agent is one or more of an HDAC inhibitor (e.g., panobinostat, romidepsin, vorinostat, or citarinostat), a BCL2 inhibitor (e.g., venetoclax), a BTK inhibitor (e.g., ibrutinib or acalabrutinib), an mTOR inhibitor (e.g., everolimus), a PI3K inhibitor (e.g., idelalisib), a PKCβ inhibitor (e.g., enzastaurin), a SYK inhibitor (e.g., fostamatinib), a JAK2 inhibitor (e.g., fedratinib, pacritinib, ruxolitinib, baricitinib, gandotinib, lestaurtinib, or momelotinib), an Aurora kinase inhibitor (e.g., alisertib), an EZH2 inhibitor (e.g., tazemetostat, GSK126, CPI-1205, 3-deazaneplanocin A, EPZ005687, EI1, UNC1999, or sinefungin), a BET inhibitor (e.g., birabresib or Compound B), a hypomethylating agent (e.g., 5-azacytidine or decitabine), a DOT1L inhibitor (e.g., pinometostat), a HAT inhibitor (e.g., C646), a WDR5 inhibitor (e.g., OICR-9429), a DNMT1 inhibitor (e.g., GSK3484862), an LSD-1 inhibitor (e.g., Compound C or seclidemstat), a G9A inhibitor (e.g., UNC 0631), a PRMT5 inhibitor (e.g., GSK3326595), a BRD inhibitor (e.g., LP99), a SUV420H1/H2 inhibitor (e.g., A-196), a CARM1 inhibitor (e.g., EZM2302), a PLK1 inhibitor (e.g., BI2536), an NEK2 inhibitor (e.g., JH295), an MEK inhibitor (e.g., trametinib), a PHF19 inhibitor, a PIM inhibitor (e.g., LGH-447), an IGF-1R inhibitor (e.g., linsitinib), an XPO1 inhibitor (e.g., selinexor), a BIRC5 inhibitor (e.g., YM155), or a chemotherapy (e.g., bendamustine, doxorubicin, etoposide, methotrexate, cytarabine, vincristine, ifosfamide, melphalan, oxaliplatin, or dexamethasone). In one embodiment, the hematological malignancy is AML (e.g., B-cell AML). In one embodiment, the hematological malignancy is ALL. In one embodiment, the hematological malignancy is CLL/SLL. In one embodiment, the hematological malignancy is MM. In one embodiment, the hematological malignancy is PCL. In one embodiment, the hematological malignancy is NHL. In one embodiment, the hematological malignancy is DLBCL. In one embodiment, the hematological malignancy is TCL (e.g., ALCL or Sezary Syndrome). In one embodiment, the hematological malignancy is Burkitt lymphoma. In one embodiment, the hematological malignancy is HL. In one embodiment, the hematological malignancy is MZL (e.g., SMZL). In one embodiment, the hematological malignancy is MDS.

In one embodiment, a method provided herein further comprises administering to the patient a therapeutically effective amount of obinutuzumab. In one embodiment, provided herein is a method of treating a hematological malignancy provided herein, which comprises administering to a patient a therapeutically effective amount of Compound A, in combination with a second active agent provided herein (e.g., venetoclax), and further in combination with obinutuzumab.

In one embodiment, provided herein is a method of treating DLBCL, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating DLBCL, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating DLBCL, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating DLBCL, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating DLBCL, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating DLBCL, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating DLBCL, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating DLBCL, which comprises administering to a patient a therapeutically effective amount of Compound 1A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating DLBCL, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating DLBCL, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating DLBCL, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating DLBCL, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating DLBCL, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating DLBCL, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating DLBCL, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating DLBCL, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating DLBCL, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating DLBCL, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating DLBCL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating DLBCL, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating DLBCL, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating DLBCL, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating DLBCL, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating DLBCL, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating DLBCL, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating DLBCL, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating DLBCL, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating DLBCL, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating DLBCL, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating DLBCL, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating DLBCL, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating DLBCL, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating DLBCL, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating DLBCL, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating DLBCL, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating DLBCL, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating DLBCL, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating DLBCL, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating DLBCL, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating DLBCL, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating DLBCL, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating DLBCL, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating DLBCL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating DLBCL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating DLBCL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating DLBCL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating DLBCL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

In one embodiment, provided herein is a method of treating CLL/SLL, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating CLL/SLL, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating CLL/SLL, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating CLL/SLL, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating CLL/SLL, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating CLL/SLL, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating CLL/SLL, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating CLL/SLL, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating CLL/SLL, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating CLL/SLL, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating CLL/SLL, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating CLL/SLL, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating CLL/SLL, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating CLL/SLL, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating CLL/SLL, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating CLL/SLL, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating CLL/SLL, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating CLL/SLL, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating CLL/SLL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating CLL/SLL, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating CLL/SLL, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating CLL/SLL, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating CLL/SLL, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating CLL/SLL, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating CLL/SLL, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating CLL/SLL, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating CLL/SLL, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating CLL/SLL, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating CLL/SLL, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating CLL/SLL, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating CLL/SLL, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating CLL/SLL, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating CLL/SLL, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating CLL/SLL, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating CLL/SLL, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating CLL/SLL, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating CLL/SLL, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating CLL/SLL, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating CLL/SLL, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating CLL/SLL, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating CLL/SLL, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating CLL/SLL, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating CLL/SLL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating CLL/SLL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating CLL/SLL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating CLL/SLL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating CLL/SLL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

In one embodiment, provided herein is a method of treating AML, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate. In one embodiment, the AML is B-cell AML.

In one embodiment, provided herein is a method of treating AML, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin. In one embodiment, the AML is B-cell AML.

In one embodiment, provided herein is a method of treating AML, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat. In one embodiment, the AML is B-cell AML.

In one embodiment, provided herein is a method of treating AML, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat. In one embodiment, the AML is B-cell AML.

In one embodiment, provided herein is a method of treating AML, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax. In one embodiment, the AML is B-cell AML.

In one embodiment, provided herein is a method of treating AML, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib. In one embodiment, the AML is B-cell AML.

In one embodiment, provided herein is a method of treating AML, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is everolimus. In one embodiment, the AML is B-cell AML.

In one embodiment, provided herein is a method of treating AML, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib. In one embodiment, the AML is B-cell AML.

In one embodiment, provided herein is a method of treating AML, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin. In one embodiment, the AML is B-cell AML.

In one embodiment, provided herein is a method of treating AML, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate. In one embodiment, the AML is B-cell AML.

In one embodiment, provided herein is a method of treating AML, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib. In one embodiment, the AML is B-cell AML.

In one embodiment, provided herein is a method of treating AML, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib. In one embodiment, the AML is B-cell AML.

In one embodiment, provided herein is a method of treating AML, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate. In one embodiment, the AML is B-cell AML.

In one embodiment, provided herein is a method of treating AML, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is alisertib. In one embodiment, the AML is B-cell AML.

In one embodiment, provided herein is a method of treating AML, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat. In one embodiment, the AML is B-cell AML.

In one embodiment, provided herein is a method of treating AML, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is GSK126. In one embodiment, the AML is B-cell AML.

In one embodiment, provided herein is a method of treating AML, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205. In one embodiment, the AML is B-cell AML.

In one embodiment, provided herein is a method of treating AML, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is birabresib. In one embodiment, the AML is B-cell AML.

In one embodiment, provided herein is a method of treating AML, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is Compound B. In one embodiment, the AML is B-cell AML.

In one embodiment, provided herein is a method of treating AML, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine. In one embodiment, the AML is B-cell AML.

In one embodiment, provided herein is a method of treating AML, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is decitabine. In one embodiment, the AML is B-cell AML.

In one embodiment, provided herein is a method of treating AML, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat. In one embodiment, the AML is B-cell AML.

In one embodiment, provided herein is a method of treating AML, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is C646. In one embodiment, the AML is B-cell AML.

In one embodiment, provided herein is a method of treating AML, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429. In one embodiment, the AML is B-cell AML.

In one embodiment, provided herein is a method of treating AML, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862. In one embodiment, the AML is B-cell AML.

In one embodiment, provided herein is a method of treating AML, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate. In one embodiment, the AML is B-cell AML.

In one embodiment, provided herein is a method of treating AML, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate. In one embodiment, the AML is B-cell AML.

In one embodiment, provided herein is a method of treating AML, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631. In one embodiment, the AML is B-cell AML.

In one embodiment, provided herein is a method of treating AML, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595. In one embodiment, the AML is B-cell AML.

In one embodiment, provided herein is a method of treating AML, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is LP99. In one embodiment, the AML is B-cell AML.

In one embodiment, provided herein is a method of treating AML, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is A-196. In one embodiment, the AML is B-cell AML.

In one embodiment, provided herein is a method of treating AML, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302. In one embodiment, the AML is B-cell AML.

In one embodiment, provided herein is a method of treating AML, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride. In one embodiment, the AML is B-cell AML.

In one embodiment, provided herein is a method of treating AML, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride. In one embodiment, the AML is B-cell AML.

In one embodiment, provided herein is a method of treating AML, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate. In one embodiment, the AML is B-cell AML.

In one embodiment, provided herein is a method of treating AML, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium. In one embodiment, the AML is B-cell AML.

In one embodiment, provided herein is a method of treating AML, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine. In one embodiment, the AML is B-cell AML.

In one embodiment, provided herein is a method of treating AML, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate. In one embodiment, the AML is B-cell AML.

In one embodiment, provided herein is a method of treating AML, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide. In one embodiment, the AML is B-cell AML.

In one embodiment, provided herein is a method of treating AML, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride. In one embodiment, the AML is B-cell AML.

In one embodiment, provided herein is a method of treating AML, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin. In one embodiment, the AML is B-cell AML.

In one embodiment, provided herein is a method of treating AML, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone. In one embodiment, the AML is B-cell AML.

In one embodiment, provided herein is a method of treating AML, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is BI2536. In one embodiment, the AML is B-cell AML.

In one embodiment, provided herein is a method of treating AML, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is JQ1. In one embodiment, the AML is B-cell AML.

In one embodiment, provided herein is a method of treating AML, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is Compound B. In one embodiment, the AML is B-cell AML.

In one embodiment, provided herein is a method of treating AML, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating AML, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863. In one embodiment, the AML is B-cell AML.

In one embodiment, provided herein is a method of treating ALL, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating ALL, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating ALL, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating ALL, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating ALL, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating ALL, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating ALL, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating ALL, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating ALL, which comprises administering to a patient a therapeutically effective amount of A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating ALL, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating ALL, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating ALL, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating ALL, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating ALL, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating ALL, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating ALL, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating ALL, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating ALL, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating ALL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating ALL, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating ALL, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating ALL, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating ALL, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating ALL, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating ALL, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating ALL, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating ALL, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating ALL, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating ALL, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating ALL, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating ALL, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating ALL, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating ALL, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating ALL, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating ALL, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating ALL, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating ALL, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating ALL, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating ALL, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating ALL, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating ALL, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating ALL, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating ALL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating ALL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating ALL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating ALL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating ALL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

In one embodiment, provided herein is a method of treating MM, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating MM, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating MM, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating MM, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating MM, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating MM, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating MM, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating MM, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating MM, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating MM, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating MM, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating MM, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating MM, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating MM, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating MM, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating MM, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating MM, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating MM, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating MM, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating MM, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating MM, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating MM, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating MM, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating MM, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating MM, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating MM, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating MM, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating MM, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating MM, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating MM, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating MM, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating MM, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating MM, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating MM, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating MM, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating MM, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating MM, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating MM, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating MM, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating MM, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating MM, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating MM, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating MM, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating MM, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating MM, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating MM, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating MM, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

In one embodiment, provided herein is a method of treating PCL, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating PCL, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating PCL, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating PCL, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating PCL, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating PCL, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating PCL, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating PCL, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating PCL, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating PCL, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating PCL, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating PCL, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating PCL, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating PCL, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating PCL, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating PCL, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating PCL, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating PCL, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating PCL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating PCL, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating PCL, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating PCL, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating PCL, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating PCL, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating PCL, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating PCL, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating PCL, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating PCL, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating PCL, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating PCL, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating PCL, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating PCL, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating PCL, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating PCL, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating PCL, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating PCL, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating PCL, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating PCL, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating PCL, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating PCL, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating PCL, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating PCL, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating PCL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating PCL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating PCL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating PCL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating PCL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

In one embodiment, provided herein is a method of treating NHL, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating NHL, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating NHL, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating NHL, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating NHL, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating NHL, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating NHL, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating NHL, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating NHL, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating NHL, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating NHL, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating NHL, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating NHL, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib.

In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating NHL, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating NHL, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating NHL, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating NHL, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating NHL, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating NHL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating NHL, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating NHL, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating NHL, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating NHL, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating NHL, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating NHL, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating NHL, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating NHL, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating NHL, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating NHL, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating NHL, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating NHL, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating NHL, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating NHL, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating NHL, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating NHL, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating NHL, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating NHL, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating NHL, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating NHL, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating NHL, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating NHL, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating NHL, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating NHL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating NHL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating NHL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating NHL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating NHL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

In one embodiment, provided herein is a method of treating TCL, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate. In one embodiment, the TCL is ALCL. In one embodiment, the TCL is Sezary Syndrome.

In one embodiment, provided herein is a method of treating TCL, which comprises administering to a patient a therapeutically effective amount of A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is C646. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is LP99. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is A-196. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin. In one embodiment, the TCL is ALCL. In one embodiment, the TCL is Sezary Syndrome.

In one embodiment, provided herein is a method of treating TCL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B. In one embodiment, the TCL is ALCL. In one embodiment, the TCL is Sezary Syndrome.

In one embodiment, provided herein is a method of treating TCL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating TCL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863. In one embodiment, the TCL is ALCL. In one embodiment, the TCL is Sezary Syndrome.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is citarinostat, or a tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is C646, or a tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is OICR-9429, or a tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is Compound C, or a tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is seclidemstat, or a tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is UNC0631, or a tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is A-196, or a tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating BL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating BL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating BL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating BL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating BL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating BL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is citarinostat, or a tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is C646, or a tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is OICR-9429, or a tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is Compound C, or a tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is seclidemstat, or a tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is UNC0631, or a tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is A-196, or a tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating HL, which comprises administering to a patient a therapeutically effective amount of Compound 1, or an enantiomer, mixture of enantiomers, tautomer, isotopolog, or pharmaceutically acceptable salt thereof, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating HL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating HL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating HL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating HL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating HL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

In one embodiment, provided herein is a method of treating MZL, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate. In one embodiment, the MZL is SMZL.

In one embodiment, provided herein is a method of treating MZL, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin. In one embodiment, the MZL is SMZL.

In one embodiment, provided herein is a method of treating MZL, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat. In one embodiment, the MZL is SMZL.

In one embodiment, provided herein is a method of treating MZL, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat. In one embodiment, the MZL is SMZL.

In one embodiment, provided herein is a method of treating MZL, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax. In one embodiment, the MZL is SMZL.

In one embodiment, provided herein is a method of treating MZL, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib. In one embodiment, the MZL is SMZL.

In one embodiment, provided herein is a method of treating MZL, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is everolimus. In one embodiment, the MZL is SMZL.

In one embodiment, provided herein is a method of treating MZL, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib. In one embodiment, the MZL is SMZL.

In one embodiment, provided herein is a method of treating MZL, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin. In one embodiment, the MZL is SMZL.

In one embodiment, provided herein is a method of treating MZL, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate. In one embodiment, the MZL is SMZL.

In one embodiment, provided herein is a method of treating MZL, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib. In one embodiment, the MZL is SMZL.

In one embodiment, provided herein is a method of treating MZL, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib. In one embodiment, the MZL is SMZL.

In one embodiment, provided herein is a method of treating MZL, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate. In one embodiment, the MZL is SMZL.

In one embodiment, provided herein is a method of treating MZL, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is alisertib. In one embodiment, the MZL is SMZL.

In one embodiment, provided herein is a method of treating MZL, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat. In one embodiment, the MZL is SMZL.

In one embodiment, provided herein is a method of treating MZL, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is GSK126. In one embodiment, the MZL is SMZL.

In one embodiment, provided herein is a method of treating MZL, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205. In one embodiment, the MZL is SMZL.

In one embodiment, provided herein is a method of treating MZL, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is birabresib. In one embodiment, the MZL is SMZL.

In one embodiment, provided herein is a method of treating MZL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B. In one embodiment, the MZL is SMZL.

In one embodiment, provided herein is a method of treating MZL, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine. In one embodiment, the MZL is SMZL.

In one embodiment, provided herein is a method of treating MZL, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is decitabine. In one embodiment, the MZL is SMZL.

In one embodiment, provided herein is a method of treating MZL, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat. In one embodiment, the MZL is SMZL.

In one embodiment, provided herein is a method of treating MZL, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is C646. In one embodiment, the MZL is SMZL.

In one embodiment, provided herein is a method of treating MZL, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429. In one embodiment, the MZL is SMZL.

In one embodiment, provided herein is a method of treating MZL, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862. In one embodiment, the MZL is SMZL.

In one embodiment, provided herein is a method of treating MZL, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate. In one embodiment, the MZL is SMZL.

In one embodiment, provided herein is a method of treating MZL, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate. In one embodiment, the MZL is SMZL.

In one embodiment, provided herein is a method of treating MZL, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631. In one embodiment, the MZL is SMZL.

In one embodiment, provided herein is a method of treating MZL, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595. In one embodiment, the MZL is SMZL.

In one embodiment, provided herein is a method of treating MZL, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is LP99. In one embodiment, the MZL is SMZL.

In one embodiment, provided herein is a method of treating MZL, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is A-196. In one embodiment, the MZL is SMZL.

In one embodiment, provided herein is a method of treating MZL, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302. In one embodiment, the MZL is SMZL.

In one embodiment, provided herein is a method of treating MZL, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride. In one embodiment, the MZL is SMZL.

In one embodiment, provided herein is a method of treating MZL, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride. In one embodiment, the MZL is SMZL.

In one embodiment, provided herein is a method of treating MZL, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate. In one embodiment, the MZL is SMZL.

In one embodiment, provided herein is a method of treating MZL, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium. In one embodiment, the MZL is SMZL.

In one embodiment, provided herein is a method of treating MZL, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine. In one embodiment, the MZL is SMZL.

In one embodiment, provided herein is a method of treating MZL, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate. In one embodiment, the MZL is SMZL.

In one embodiment, provided herein is a method of treating MZL, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide. In one embodiment, the MZL is SMZL.

In one embodiment, provided herein is a method of treating MZL, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride. In one embodiment, the MZL is SMZL.

In one embodiment, provided herein is a method of treating MZL, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin. In one embodiment, the MZL is SMZL.

In one embodiment, provided herein is a method of treating MZL, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone. In one embodiment, the MZL is SMZL.

In one embodiment, provided herein is a method of treating MZL, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is BI2536. In one embodiment, the MZL is SMZL.

In one embodiment, provided herein is a method of treating MZL, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is JQ1. In one embodiment, the MZL is SMZL.

In one embodiment, provided herein is a method of treating MZL, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is Compound B. In one embodiment, the MZL is SMZL.

In one embodiment, provided herein is a method of treating MZL, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating MZL, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863. In one embodiment, the MZL is SMZL.

In one embodiment, provided herein is a method of treating MDS, which comprises administering to a patient a therapeutically effective amount of Compound A, in combination with a second active agent, wherein the second active agent is panobinostat, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is panobinostat lactate.

In one embodiment, provided herein is a method of treating MDS, which comprises administering to a patient a therapeutically effective amount of Compound A, in combination with a second active agent, wherein the second active agent is romidepsin, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is romidepsin.

In one embodiment, provided herein is a method of treating MDS, which comprises administering to a patient a therapeutically effective amount of Compound A, in combination with a second active agent, wherein the second active agent is vorinostat, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is vorinostat.

In one embodiment, provided herein is a method of treating MDS, which comprises administering to a patient a therapeutically effective amount of Compound A, in combination with a second active agent, wherein the second active agent is citarinostat, or a tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is citarinostat.

In one embodiment, provided herein is a method of treating MDS, which comprises administering to a patient a therapeutically effective amount of Compound A, in combination with a second active agent, wherein the second active agent is venetoclax, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is venetoclax.

In one embodiment, provided herein is a method of treating MDS, which comprises administering to a patient a therapeutically effective amount of Compound A, in combination with a second active agent, wherein the second active agent is ibrutinib, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is ibrutinib.

In one embodiment, provided herein is a method of treating MDS, which comprises administering to a patient a therapeutically effective amount of Compound A, in combination with a second active agent, wherein the second active agent is everolimus, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is everolimus.

In one embodiment, provided herein is a method of treating MDS, which comprises administering to a patient a therapeutically effective amount of Compound A, in combination with a second active agent, wherein the second active agent is idelalisib, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is idelalisib.

In one embodiment, provided herein is a method of treating MDS, which comprises administering to a patient a therapeutically effective amount of Compound A, in combination with a second active agent, wherein the second active agent is enzastaurin, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is enzastaurin. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is a hydrochloride salt of enzastaurin.

In one embodiment, provided herein is a method of treating MDS, which comprises administering to a patient a therapeutically effective amount of Compound A, in combination with a second active agent, wherein the second active agent is fostamatinib, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is fostamatinib disodium hexahydrate.

In one embodiment, provided herein is a method of treating MDS, which comprises administering to a patient a therapeutically effective amount of Compound A, in combination with a second active agent, wherein the second active agent is fedratinib, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is fedratinib.

In one embodiment, provided herein is a method of treating MDS, which comprises administering to a patient a therapeutically effective amount of Compound A, in combination with a second active agent, wherein the second active agent is pacritinib, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is pacritinib.

In one embodiment, provided herein is a method of treating MDS, which comprises administering to a patient a therapeutically effective amount of Compound A, in combination with a second active agent, wherein the second active agent is ruxolitinib, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is ruxolitinib phosphate.

In one embodiment, provided herein is a method of treating MDS, which comprises administering to a patient a therapeutically effective amount of Compound A, in combination with a second active agent, wherein the second active agent is alisertib, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is alisertib.

In one embodiment, provided herein is a method of treating MDS, which comprises administering to a patient a therapeutically effective amount of Compound A, in combination with a second active agent, wherein the second active agent is tazemetostat, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is tazemetostat.

In one embodiment, provided herein is a method of treating MDS, which comprises administering to a patient a therapeutically effective amount of Compound A, in combination with a second active agent, wherein the second active agent is GSK126, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is GSK126.

In one embodiment, provided herein is a method of treating MDS, which comprises administering to a patient a therapeutically effective amount of Compound A, in combination with a second active agent, wherein the second active agent is CPI-1205, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is CPI-1205.

In one embodiment, provided herein is a method of treating MDS, which comprises administering to a patient a therapeutically effective amount of Compound A, in combination with a second active agent, wherein the second active agent is birabresib, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is birabresib.

In one embodiment, provided herein is a method of treating MDS, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating MDS, which comprises administering to a patient a therapeutically effective amount of Compound A, in combination with a second active agent, wherein the second active agent is 5-azacytidine, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is 5-azacytidine.

In one embodiment, provided herein is a method of treating MDS, which comprises administering to a patient a therapeutically effective amount of Compound A, in combination with a second active agent, wherein the second active agent is decitabine, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is decitabine.

In one embodiment, provided herein is a method of treating MDS, which comprises administering to a patient a therapeutically effective amount of Compound A, in combination with a second active agent, wherein the second active agent is pinometostat, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is pinometostat.

In one embodiment, provided herein is a method of treating MDS, which comprises administering to a patient a therapeutically effective amount of Compound A, in combination with a second active agent, wherein the second active agent is C646, or a tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is C646.

In one embodiment, provided herein is a method of treating MDS, which comprises administering to a patient a therapeutically effective amount of Compound A, in combination with a second active agent, wherein the second active agent is OICR-9429, or a tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is OICR-9429.

In one embodiment, provided herein is a method of treating MDS, which comprises administering to a patient a therapeutically effective amount of Compound A, in combination with a second active agent, wherein the second active agent is GSK3484862, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is GSK3484862.

In one embodiment, provided herein is a method of treating MDS, which comprises administering to a patient a therapeutically effective amount of Compound A, in combination with a second active agent, wherein the second active agent is Compound C, or a tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is Compound C. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is Compound C besylate.

In one embodiment, provided herein is a method of treating MDS, which comprises administering to a patient a therapeutically effective amount of Compound A, in combination with a second active agent, wherein the second active agent is seclidemstat, or a tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is seclidemstat mesylate.

In one embodiment, provided herein is a method of treating MDS, which comprises administering to a patient a therapeutically effective amount of Compound A, in combination with a second active agent, wherein the second active agent is UNC0631, or a tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is UNC0631.

In one embodiment, provided herein is a method of treating MDS, which comprises administering to a patient a therapeutically effective amount of Compound A, in combination with a second active agent, wherein the second active agent is GSK3326595, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is GSK3326595.

In one embodiment, provided herein is a method of treating MDS, which comprises administering to a patient a therapeutically effective amount of Compound A, in combination with a second active agent, wherein the second active agent is LP99, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is LP99.

In one embodiment, provided herein is a method of treating MDS, which comprises administering to a patient a therapeutically effective amount of Compound A, in combination with a second active agent, wherein the second active agent is A-196, or a tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is A-196.

In one embodiment, provided herein is a method of treating MDS, which comprises administering to a patient a therapeutically effective amount of Compound A, in combination with a second active agent, wherein the second active agent is EZM2302, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is EZM2302.

In one embodiment, provided herein is a method of treating MDS, which comprises administering to a patient a therapeutically effective amount of Compound A, in combination with a second active agent, wherein the second active agent is bendamustine, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is bendamustine hydrochloride.

In one embodiment, provided herein is a method of treating MDS, which comprises administering to a patient a therapeutically effective amount of Compound A, in combination with a second active agent, wherein the second active agent is doxorubicin, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is doxorubicin hydrochloride.

In one embodiment, provided herein is a method of treating MDS, which comprises administering to a patient a therapeutically effective amount of Compound A, in combination with a second active agent, wherein the second active agent is etoposide, or a stereoisomer, mixture of stereoisomers, tautomer, isotopolog, prodrug, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is etoposide. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is etoposide phosphate.

In one embodiment, provided herein is a method of treating MDS, which comprises administering to a patient a therapeutically effective amount of Compound A, in combination with a second active agent, wherein the second active agent is methotrexate, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is methotrexate sodium.

In one embodiment, provided herein is a method of treating MDS, which comprises administering to a patient a therapeutically effective amount of Compound A, in combination with a second active agent, wherein the second active agent is cytarabine, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is cytarabine.

In one embodiment, provided herein is a method of treating MDS, which comprises administering to a patient a therapeutically effective amount of Compound A, in combination with a second active agent, wherein the second active agent is vincristine, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is vincristine. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is vincristine sulfate.

In one embodiment, provided herein is a method of treating MDS, which comprises administering to a patient a therapeutically effective amount of Compound A, in combination with a second active agent, wherein the second active agent is ifosfamide, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is ifosfamide.

In one embodiment, provided herein is a method of treating MDS, which comprises administering to a patient a therapeutically effective amount of Compound A, in combination with a second active agent, wherein the second active agent is melphalan, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is melphalan. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is melphalan hydrochloride.

In one embodiment, provided herein is a method of treating MDS, which comprises administering to a patient a therapeutically effective amount of Compound A, in combination with a second active agent, wherein the second active agent is oxaliplatin, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is oxaliplatin.

In one embodiment, provided herein is a method of treating MDS, which comprises administering to a patient a therapeutically effective amount of Compound A, in combination with a second active agent, wherein the second active agent is dexamethasone, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is dexamethasone.

In one embodiment, provided herein is a method of treating MDS, which comprises administering to a patient a therapeutically effective amount of Compound A, in combination with a second active agent, wherein the second active agent is BI2536, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is BI2536.

In one embodiment, provided herein is a method of treating MDS, which comprises administering to a patient a therapeutically effective amount of Compound A, in combination with a second active agent, wherein the second active agent is JQ1, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is JQ1.

In one embodiment, provided herein is a method of treating MDS, which comprises administering to a patient a therapeutically effective amount of Compound A, in combination with a second active agent, wherein the second active agent is Compound B, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is Compound B.

In one embodiment, provided herein is a method of treating MDS, which comprises administering to a patient a therapeutically effective amount of Compound A, in combination with a second active agent, wherein the second active agent is rac-CCT 250863, or a stereoisomer, mixture of stereoisomers, tautomer, isotopolog, or pharmaceutically acceptable salt thereof. In one embodiment, provided herein is a method of treating MDS, which comprises administering to a patient a therapeutically effective amount of Compound 1 or pharmaceutically acceptable salt thereof (e.g., a hydrochloride salt of Compound 1), in combination with a second active agent, wherein the second active agent is rac-CCT 250863.

As used herein, the term "in combination" does not restrict the order in which therapies (e.g., prophylactic and/or therapeutic agents) are administered to a patient with a disease or disorder. In one embodiment, a first therapy (e.g., a prophylactic or therapeutic agent such as a compound provided herein, e.g., Compound 1, or an enantiomer, mixture of enantiomers, tautomer, isotopolog, or pharmaceutically acceptable salt thereof) is administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before) the administration of a second therapy (e.g., a second active agent provided herein). In one embodiment, a first therapy (e.g., a prophylactic or therapeutic agent such as a compound provided herein, e.g., Compound 1, or an enantiomer, mixture of enantiomers, tautomer, isotopolog, or pharmaceutically acceptable salt thereof) is administered concomitantly with the administration of a second therapy (e.g., a second active agent provided herein). In one embodiment, a first therapy (e.g., a prophylactic or therapeutic agent such as a compound provided herein, e.g., Compound 1, or an enantiomer, mixture of enantiomers, tautomer, isotopolog, or pharmaceutically acceptable salt thereof) is administered subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapy (e.g., a second active agent provided herein).

Administration of Compound 1, or an enantiomer, mixture of enantiomers, tautomer, isotopolog, or pharmaceutically acceptable salt thereof, and a second active agent provided herein, to a patient can occur simultaneously or sequentially by the same or different routes of administration. The suitability of a particular route of administration employed for a particular active agent will depend on the active agent itself (e.g., whether it can be administered orally without decomposing prior to entering the blood stream).

The route of administration of Compound 1, or an enantiomer, mixture of enantiomers, tautomer, isotopolog, or pharmaceutically acceptable salt thereof, is independent of the route of administration of a second active agent provided herein. In one embodiment, Compound 1, or an enantiomer, mixture of enantiomers, tautomer, isotopolog, or pharmaceutically acceptable salt thereof, is administered orally. In another embodiment, Compound 1, is administered intravenously. In one embodiment, a second active agent provided herein is administered orally. In one embodiment, a second active agent provided herein is administered intravenously. Thus, in accordance with these embodiments, Compound 1, or an enantiomer, mixture of enantiomers, tautomer, isotopolog, or pharmaceutically acceptable salt thereof, is administered orally or intravenously, and a second active agent provided herein is administered orally or intravenously. In one embodiment, Compound 1, or an enantiomer, mixture of enantiomers, tautomer, isotopolog, or pharmaceutically acceptable salt thereof, and a second active agent provided herein are administered by the same mode of administration, orally or by IV. In another embodiment, Compound 1, or an enantiomer, mixture of enantiomers, tautomer, isotopolog, or pharmaceutically acceptable salt thereof, is administered by one mode of administration, e.g., orally, whereas a second active agent provided herein is administered by another mode of administration, e.g., intravenously.

The methods provided herein encompass treating a patient regardless of patient's age. In some embodiments, the subject is 18 years or older. In other embodiments, the subject is more than 18, 25, 35, 40, 45, 50, 55, 60, 65, or 70 years old. In other embodiments, the subject is less than 65 years old. In other embodiments, the subject is more than 65 years old.

5.5 Pharmaceutical Composition and Routes of Administration of Compound 1

The compound provided herein can be administered to a subject orally, topically or parenterally in the conventional form of preparations, such as capsules, microcapsules, tablets, granules, powder, troches, pills, suppositories, injections, suspensions, syrups, patches, creams, lotions, ointments, gels, sprays, solutions and emulsions. Suitable formulations can be prepared by methods commonly employed using conventional, organic or inorganic additives, such as a diluent (e.g., sucrose, starch, mannitol, sorbitol, lactose, glucose, cellulose, talc, calcium phosphate or calcium carbonate), a binder (e.g., cellulose, methylcellulose, hydroxymethylcellulose, polypropylpyrrolidone, polyvinylpyrrolidone, gelatin, gum arabic, polyethyleneglycol, sucrose or starch), a disintegrant (e.g., starch, carboxymethylcellulose, hydroxypropylstarch, low substituted hydroxypropylcellulose, sodium bicarbonate, calcium phosphate or calcium citrate), a lubricant (e.g., magnesium stearate, light anhydrous silicic acid, talc or sodium lauryl sulfate), a flavoring agent (e.g., citric acid, menthol, glycine or orange powder), a preservative (e.g, sodium benzoate, sodium bisulfite, methylparaben or propylparaben), a stabilizer (e.g., citric acid, sodium citrate or acetic acid), a suspending agent (e.g., methylcellulose, polyvinyl pyrroliclone or aluminum stearate), a dispersing agent (e.g., hydroxypropylmethylcellulose), water, and base wax (e.g., cocoa butter, white petrolatum or polyethylene glycol). The effective amount of the compounds in the pharmaceutical composition may be at a level that will exercise the desired effect for both oral and parenteral administration.

A compound provided herein can be administered orally. In one embodiment, when administered orally, a compound provided herein is administered with a meal and water. In another embodiment, the compound provided herein is dispersed in water or juice (e.g., apple juice or orange juice) and administered orally as a solution or a suspension.

The compound provided herein can also be administered intradermally, intramuscularly, intraperitoneally, percutaneously, intravenously, subcutaneously, intranasally, epidurally, sublingually, intracerebrally, intravaginally, transdermally, rectally, mucosally, by inhalation, or topically to the ears, nose, eyes, or skin. The mode of administration is left to the discretion of the health-care practitioner, and can depend in-part upon the site of the medical condition.

In one embodiment, provided herein are capsules containing a compound provided herein without an additional excipient. In another embodiment, provided herein are compositions comprising an effective amount of a compound provided herein and a pharmaceutically acceptable excipient, wherein a pharmaceutically acceptable excipient can comprise a diluent, binder, disintegrant, glidant, lubricant, or a mixture thereof. In one embodiment, the composition is a pharmaceutical composition.

The compositions can be in the form of tablets, chewable tablets, capsules, solutions, parenteral solutions, troches, suppositories and suspensions and the like. Compositions can be formulated to contain a daily dose, or a convenient fraction of a daily dose, in a dosage unit, which may be a single tablet or capsule or convenient volume of a liquid. In one embodiment, the solutions are prepared from water-soluble salts. In general, all of the compositions are prepared according to known methods in pharmaceutical chemistry. Capsules can be prepared by mixing a compound provided herein with a suitable excipient and filling the proper amount of the mixture in capsules. The usual excipients include, but are not limited to, inert powdered substances such as starch of many different kinds, powdered cellulose, especially crystalline and microcrystalline cellulose, sugars such as fructose, mannitol and sucrose, grain flours and similar edible powders. Capsules fill can also be prepared by wet granulation or by dry granulation.

A lubricant might be necessary in a capsule formulation to prevent the powder from sticking to the pin. The lubricant can be chosen from such slippery solids as talc, magnesium and calcium stearate, sodium stearyl fumarate, stearic acid and hydrogenated vegetable oils. Disintegrants are substances that swell when wetted to break up the capsule slug and release the compound. They include starches, clays, celluloses, crospovidone, croscarmellose sodium, sodium starch glycolate, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Glidants may also be used, including silicon dioxide, talc, and calcium silicate.

Tablets can be prepared by direct compression, by wet granulation, or by dry granulation. Their formulations usually incorporate diluents, binders, lubricants and disintegrants as well as the compound. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders are substances such as starch, gelatin and sugars such as lactose, fructose, glucose and the like. Natural and synthetic gums are also convenient, including acacia, alginates, methylcellulose, polyvinylpyrrolidine and the like. Polyethylene glycol, ethylcellulose and waxes can also serve as binders.

A lubricant might be necessary in a tablet formulation to prevent the tablet and punches from sticking in the die. The lubricant can be chosen from such slippery solids as talc, magnesium and calcium stearate, sodium stearyl fumarate, stearic acid and hydrogenated vegetable oils. Tablet disintegrants are substances that swell when wetted to break up the tablet and release the compound. They include starches, clays, celluloses, crospovidone, croscarmellose sodium, sodium starch glycolate, algins and gums. More particularly, corn and potato starches, methylcellulose, agar, bentonite, wood cellulose, powdered natural sponge, cation-exchange resins, alginic acid, guar gum, citrus pulp and carboxymethyl cellulose, for example, can be used as well as sodium lauryl sulfate. Glidants may also be used, including silicon dioxide, talc, and calcium silicate. Tablets can be coated with sugar as a flavor and sealant, or with film-forming protecting agents to modify the dissolution properties of the tablet. The compositions can also be formulated as chewable tablets, for example, by using substances such as mannitol in the formulation.

When it is desired to administer a compound provided herein as a suppository, typical bases can be used. Cocoa butter is a traditional suppository base, which can be modified by addition of waxes to raise its melting point slightly. Water-miscible suppository bases comprising, particularly, polyethylene glycols of various molecular weights are in wide use.

The effect of the compound provided herein can be delayed or prolonged by proper formulation. For example, a slowly soluble pellet of the compound provided herein can be prepared and incorporated in a tablet or capsule, or as a slow-release implantable device. The technique also includes making pellets of several different dissolution rates and filling capsules with a mixture of the pellets. Tablets or capsules can be coated with a film that resists dissolution for a predictable period of time. Even the parenteral preparations can be made long-acting, by dissolving or suspending the compound provided herein in oily or emulsified vehicles that allow it to disperse slowly in the serum.

Depending on the state of the disease to be treated and the subject's condition, Compound 1, or an enantiomer, mixture of enantiomers, tautomer, isotopolog, or pharmaceutically acceptable salt thereof, may be administered by oral, parenteral (e.g., intramuscular, intraperitoneal, intravenous, CIV, intracisternal injection or infusion, subcutaneous injection, or implant), inhalation, nasal, vaginal, rectal, sublingual, or topical (e.g., transdermal or local) routes of administration. Compound 1, or an enantiomer, mixture of enantiomers, tautomer, isotopolog, or pharmaceutically acceptable salt thereof, may be formulated, alone or together, in suitable dosage unit with pharmaceutically acceptable excipients, carriers, adjuvants and vehicles, appropriate for each route of administration.

In one embodiment, Compound 1, or an enantiomer, mixture of enantiomers, tautomer, isotopolog, or pharmaceutically acceptable salt thereof, is administered orally. In another embodiment, Compound 1, or an enantiomer, mixture of enantiomers, tautomer, isotopolog, or pharmaceutically acceptable salt thereof, is administered parenterally. In yet another embodiment, Compound 1, or an enantiomer, mixture of enantiomers, tautomer, isotopolog, or pharmaceutically acceptable salt thereof, is administered intravenously.

Compound 1, or an enantiomer, mixture of enantiomers, tautomer, isotopolog, or pharmaceutically acceptable salt thereof, can be delivered as a single dose such as, e.g., a single bolus injection, or oral capsules, tablets or pills; or overtime, such as, e.g., continuous infusion over time or divided bolus doses over time. The compounds as described herein can be administered repeatedly if necessary, for example, until the patient experiences stable disease or regression, or until the patient experiences disease progression or unacceptable toxicity.

Compound 1, or an enantiomer, mixture of enantiomers, tautomer, isotopolog, or pharmaceutically acceptable salt thereof, can be administered once daily (QD), or divided into multiple daily doses such as twice daily (BID), three times daily (TID), and four times daily (QID). In addition, the administration can be continuous (i.e., daily for consecutive days or every day), intermittent, e.g., in cycles (i.e., including days, weeks, or months of rest without drug). As used herein, the term "daily" is intended to mean that a therapeutic compound, such as Compound 1, or an enantiomer, mixture of enantiomers, tautomer, isotopolog, or pharmaceutically acceptable salt thereof, is administered once or more than once each day, for example, for a period of time. The term "continuous" is intended to mean that a therapeutic compound, such as Compound 1, or an enantiomer, mixture of enantiomers, tautomer, isotopolog, or pharmaceutically acceptable salt thereof, is administered daily for an uninterrupted period of at least 7 days to 52 weeks. The term "intermittent" or "intermittently" as used herein is intended to mean stopping and starting at either regular or irregular intervals. For example, intermittent administration of Compound 1, or an enantiomer, mixture of enantiomers, tautomer, isotopolog, or pharmaceutically acceptable salt thereof, is administration for one to six days per week, administration in cycles (e.g., daily administration for two to eight consecutive weeks, then a rest period with no administration for up to one week), or administration on alternate days. The term "cycling" as used herein is intended to mean that a therapeutic compound, such as Compound 1, or an enantiomer, mixture of enantiomers, tautomer, isotopolog, or pharmaceutically acceptable salt thereof, is administered daily or continuously but with a rest period.

In some embodiments, the frequency of administration is in the range of about a daily dose to about a monthly dose. In certain embodiments, administration is once a day, twice a day, three times a day, four times a day, once every other day, twice a week, once every week, once every two weeks, once every three weeks, or once every four weeks. In one embodiment, Compound 1, or an enantiomer, mixture of enantiomers, tautomer, isotopolog, or pharmaceutically acceptable salt thereof, is administered once a day. In another embodiment, Compound 1, or an enantiomer, mixture of enantiomers, tautomer, isotopolog, or pharmaceutically acceptable salt thereof, is administered twice a day. In yet another embodiment, Compound 1, or an enantiomer, mixture of enantiomers, tautomer, isotopolog, or pharmaceutically acceptable salt thereof, is administered three times a day. In still another embodiment, Compound 1, or an enantiomer, mixture of enantiomers, tautomer, isotopolog, or pharmaceutically acceptable salt thereof, is administered four times a day.

In certain embodiments, the methods provided herein include an administration of a therapeutically effective amount of Compound 1, or an enantiomer, mixture of enantiomers, tautomer, isotopolog, or pharmaceutically acceptable salt thereof, in one or more 7-day treatment cycles. In another embodiment, the methods provided herein include an administration of a therapeutically effective amount of Compound 1, or an enantiomer, mixture of enantiomers, tautomer, isotopolog, or pharmaceutically acceptable salt thereof, on days 1 to 5 of a 7-day cycle. In another embodiment, the methods provided herein include an administration of a therapeutically effective amount of Compound 1, or an enantiomer, mixture of enantiomers, tautomer, isotopolog, or pharmaceutically acceptable salt thereof, on days 1 to 3 of a 7-day cycle.

In certain embodiments, the methods provided herein include an administration of a therapeutically effective amount of Compound 1, or an enantiomer, mixture of enantiomers, tautomer, isotopolog, or pharmaceutically acceptable salt thereof, in one or more 14-day treatment cycles. In another embodiment, the methods provided herein include an administration of a therapeutically effective amount of Compound 1, or an enantiomer, mixture of enantiomers, tautomer, isotopolog, or pharmaceutically acceptable salt thereof, on days 1 to 7 of a 14-day cycle. In another embodiment, the methods provided herein include an administration of a therapeutically effective amount of Compound 1, or an enantiomer, mixture of enantiomers, tautomer, isotopolog, or pharmaceutically acceptable salt thereof, on days 1 to 10 of a 14-day cycle.

In certain embodiments, the methods provided herein include an administration of a therapeutically effective amount of Compound 1, or an enantiomer, mixture of enantiomers, tautomer, isotopolog, or pharmaceutically acceptable salt thereof, in one or more 28-day treatment cycles. In another embodiment, the methods provided herein include an administration of a therapeutically effective amount of Compound 1, or an enantiomer, mixture of enantiomers, tautomer, isotopolog, or pharmaceutically acceptable salt thereof, on days 1 to 21 of a 28-day cycle. In another embodiment, the methods provided herein include an administration of a therapeutically effective amount of Compound 1, or an enantiomer, mixture of enantiomers, tautomer, isotopolog, or pharmaceutically acceptable salt thereof, on days 1 to 5, days 8 to 12, days 15 to 19, and days 22 to 26 of a 28-day cycle. In another embodiment, the methods provided herein include an administration of a therapeutically effective amount of Compound 1, or an enantiomer, mixture of enantiomers, tautomer, isotopolog, or pharmaceutically acceptable salt thereof, on days 1 to 10 and days 15 to 24 of a 28-day cycle.

In one embodiment, Compound 1, or an enantiomer, mixture of enantiomers, tautomer, isotopolog, or pharmaceutically acceptable salt thereof, is administered once daily for 5 days followed by 2 days of rest. In one embodiment, Compound 1, or an enantiomer, mixture of enantiomers, tautomer, isotopolog, or pharmaceutically acceptable salt thereof, is administered once daily for 3 days followed by 4 days of rest. In one embodiment, Compound 1, or an enantiomer, mixture of enantiomers, tautomer, isotopolog, or pharmaceutically acceptable salt thereof, is administered once daily for 7 days followed by 7 days of rest. In one embodiment, Compound 1, or an enantiomer, mixture of enantiomers, tautomer, isotopolog, or pharmaceutically acceptable salt thereof, is administered once daily for 10 days followed by 4 days of rest. In one embodiment, Compound 1, or an enantiomer, mixture of enantiomers, tautomer, isotopolog, or pharmaceutically acceptable salt thereof, is administered once daily for 21 days followed by 7 days of rest.

Any treatment cycle described herein can be repeated for at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30 or more cycles. In certain instances, the treatment cycle as described herein includes from 1 to about 24 cycles, from about 2 to about 16 cycles, or from about 2 to about 4 cycles. In certain instances a treatment cycle as described herein includes from 1 to about 4 cycles. In some embodiments, a therapeutically effective amount of Compound 1, or an enantiomer, mixture of enantiomers, tautomer, isotopolog, or pharmaceutically acceptable salt thereof, is administered for 1 to 13 cycles of 28 days (e.g., about 1 year). In some embodiments, a therapeutically effective amount of Compound 1, or an enantiomer, mixture of enantiomers, tautomer, isotopolog, or pharmaceutically acceptable salt thereof, is administered for 1 to 24 cycles of 28 days (e.g., about 2 years). In certain instances, the cycling therapy is not limited to the number of cycles, and the therapy is continued until disease progression. Cycles can in certain instances include varying the duration of administration periods and/or rest periods described herein.

5.6 Dosing of Second Active Agents

In one embodiment, the specific amount (dosage) of a second active agent provided herein as used in the methods provided herein is determined by factors such as the specific agent used, the type of hematological malignancies being treated or managed, the severity and stage of disease, the amount of Compound 1, or an enantiomer, mixture of enantiomers, tautomer, isotopolog, or pharmaceutically acceptable salt thereof, and any optional additional active agents concurrently administered to the patient.

In one embodiment, the dosage of a second active agent provided herein as used in the methods provided herein is determined based on a commercial package insert of medicament (e.g., a label) as approved by the FDA or a similar regulatory agency of a country other than the USA for said active agent. In one embodiment, the dosage of a second active agent provided herein as used in the methods provided herein is a dosage approved by the FDA or a similar regulatory agency of a country other than the USA for said active agent. In one embodiment, the dosage of a second active agent provided herein as used in the methods provided herein is a dosage used in a human clinical trial for said active agent. In one embodiment, the dosage of a second active agent provided herein as used in the methods provided herein is lower than a dosage approved by the FDA or a similar regulatory agency of a country other than the USA for said active agent or a dosage used in a human clinical trial for said active agent, depending on, e.g., the synergistic effects between the second active agent and Compound 1.

In one embodiment, the second active agent used in the methods provided herein is an HDAC inhibitor.

In one embodiment, the HDAC inhibitor (e.g., panobinostat or panobinostat lactate) is administered at a dosage of in the range of from about 5 mg to about 40 mg, from about 10 mg to about 30 mg, or from about 15 mg to about 25 mg once every other day. In one embodiment, the HDAC inhibitor (e.g., panobinostat or panobinostat lactate) is administered at a dosage of no more than about 40 mg, no more than about 30 mg, no more than about 25 mg, no more than about 20 mg, no more than about 15 mg, no more than about 10 mg, or no more than about 5 mg once every other day. In one embodiment, the HDAC inhibitor (e.g., panobinostat or panobinostat lactate) is administered at a dosage of about 5 mg once every other day. In one embodiment, the HDAC inhibitor (e.g., panobinostat or panobinostat lactate) is administered at a dosage of about 10 mg once every other day. In one embodiment, the HDAC inhibitor (e.g., panobinostat or panobinostat lactate) is administered at a dosage of about 15 mg once every other day. In one embodiment, the HDAC inhibitor (e.g., panobinostat or panobinostat lactate) is administered at a dosage of about 20 mg once every other day. In one embodiment, the HDAC inhibitor (e.g., panobinostat or panobinostat lactate) is administered at a dosage of about 25 mg once every other day. In one embodiment, the HDAC inhibitor (e.g., panobinostat or panobinostat lactate) is administered at a dosage of about 30 mg once every other day. In one embodiment, the HDAC inhibitor (e.g., panobinostat or panobinostat lactate) is administered at a dosage of about 40 mg once every other day. In one embodiment, the HDAC inhibitor (e.g., panobinostat or panobinostat lactate) is administered at a dosage described herein once every other day for 3 doses per week (on Days 1, 3, 5, 8, 10, and 12) of Weeks 1 and 2 of each 21-day cycle. In one embodiment, the HDAC inhibitor (e.g., panobinostat or panobinostat lactate) is administered at a dosage of about 20 mg once every other day for 3 doses per week (on Days 1, 3, 5, 8, 10, and 12) of Weeks 1 and 2 of each 21-day cycle. In one embodiment, the HDAC inhibitor (e.g., panobinostat or panobinostat lactate) is administered for 8 cycles. In one embodiment, the HDAC inhibitor (e.g., panobinostat or panobinostat lactate) is administered orally.

In one embodiment, the HDAC inhibitor (e.g., romidepsin) is administered at a dosage of in the range of from about 3.5 mg/m$^2$ to about 28 mg/m$^2$, from about 7 mg/m$^2$ to about 21 mg/m$^2$, or from about 10 mg/m$^2$ to about 18 mg/m$^2$. In one embodiment, the HDAC inhibitor (e.g., romidepsin) is administered at a dosage of no more than about 28 mg/m$^2$, no more than about 21 mg/m$^2$, no more than about 18 mg/m$^2$, no more than about 14 mg/m$^2$, no more than about 10 mg/m$^2$, no more than about 7 mg/m$^2$, or no more than about 3.5 mg/m$^2$. In one embodiment, the HDAC inhibitor (e.g., romidepsin) is administered at a dosage of about 3.5 mg/m$^2$. In one embodiment, the HDAC inhibitor (e.g., romidepsin) is administered at a dosage of about 7 mg/m$^2$. In one embodiment, the HDAC inhibitor (e.g., romidepsin) is administered at a dosage of about 10 mg/m$^2$. In one embodiment, the HDAC inhibitor (e.g., romidepsin) is administered at a dosage of about 14 mg/m$^2$. In one embodiment, the HDAC inhibitor (e.g., romidepsin) is administered at a dosage of about 18 mg/m$^2$. In one embodiment, the HDAC inhibitor (e.g., romidepsin) is administered at a dosage of about 21 mg/m$^2$. In one embodiment, the HDAC inhibitor (e.g., romidepsin) is administered at a dosage of about 28 mg/m$^2$. In one embodiment, the HDAC inhibitor (e.g., romidepsin) is administered at a dosage described herein on days 1, 8, and 15 of a 28-day cycle. In one embodiment, the HDAC inhibitor (e.g., romidepsin) is administered at a dosage of about 14 mg/m$^2$ on days 1, 8, and 15 of a 28-day cycle. In one embodiment, the HDAC inhibitor (e.g., romidepsin) is administered intravenously. In one embodiment, the HDAC inhibitor (e.g., romidepsin) is administered intravenously over a period of about 4 hours.

In one embodiment, the HDAC inhibitor (e.g., vorinostat) is administered at a dosage of in the range of from about 100 mg to about 600 mg, from about 200 mg to about 500 mg, or from about 300 mg to about 400 mg once daily. In one embodiment, the HDAC inhibitor (e.g., vorinostat) is administered at a dosage of no more than about 600 mg, no more than about 500 mg, no more than about 400 mg, no more than about 300 mg, no more than about 200 mg, or no more than about 100 mg once daily. In one embodiment, the HDAC inhibitor (e.g., vorinostat) is administered at a dosage of about 100 mg once daily. In one embodiment, the HDAC inhibitor (e.g., vorinostat) is administered at a dosage of about 200 mg once daily. In one embodiment, the HDAC inhibitor (e.g., vorinostat) is administered at a dosage of about 300 mg once daily. In one embodiment, the HDAC inhibitor (e.g., vorinostat) is administered at a dosage of about 400 mg once daily. In one embodiment, the HDAC inhibitor (e.g., vorinostat) is administered at a dosage of about 500 mg once daily. In one embodiment, the HDAC inhibitor (e.g., vorinostat) is administered at a dosage of about 600 mg once daily. In one embodiment, the HDAC inhibitor (e.g., vorinostat) is administered orally.

In one embodiment, the second active agent used in the methods provided herein is an HDAC6 inhibitor. In one embodiment, the HDAC6 inhibitor (e.g., citarinostat) is administered at a dosage of in the range of from about 100 mg to about 550 mg, or from about 180 mg to about 480 mg once daily. In one embodiment, the HDAC6 inhibitor (e.g., citarinostat) is administered at a dosage of no more than about 550 mg, no more than about 480 mg, no more than about 360 mg, no more than about 180 mg, or no more than about 100 mg once daily. In one embodiment, the HDAC6 inhibitor (e.g., citarinostat) is administered at a dosage of about 100 mg once daily. In one embodiment, the HDAC6 inhibitor (e.g., citarinostat) is administered at a dosage of about 180 mg once daily. In one embodiment, the HDAC6 inhibitor (e.g., citarinostat) is administered at a dosage of about 360 mg once daily. In one embodiment, the HDAC6 inhibitor (e.g., citarinostat) is administered at a dosage of about 480 mg once daily. In one embodiment, the HDAC6 inhibitor (e.g., citarinostat) is administered at a dosage of about 550 mg once daily. In one embodiment, the HDAC6 inhibitor (e.g., citarinostat) is administered orally.

In one embodiment, the second active agent used in the methods provided herein is a BCL2 inhibitor. In one embodiment, the BCL2 inhibitor (e.g., venetoclax) is administered at a dosage of in the range of from about 5 mg to about 600 mg, from about 10 mg to about 500 mg, from about 20 mg to about 400 mg, or from about 50 mg to about 200 mg once daily. In one embodiment, the BCL2 inhibitor (e.g., venetoclax) is administered at a dosage of no more than about 600 mg, no more than about 500 mg, no more than about 400 mg, no more than about 200 mg, no more than about 100 mg, no more than about 50 mg, no more than about 20 mg, no more than about 10 mg, or no more than about 5 mg once daily. In one embodiment, the BCL2 inhibitor (e.g., venetoclax) is administered at a dosage of about 5 mg once daily. In one embodiment, the BCL2 inhibitor (e.g., venetoclax) is administered at a dosage of about 10 mg once daily. In one embodiment, the BCL2 inhibitor (e.g., venetoclax) is administered at a dosage of about 20 mg once daily. In one embodiment, the BCL2 inhibitor (e.g., venetoclax) is administered at a dosage of about 50 mg once daily. In one embodiment, the BCL2 inhibitor (e.g., venetoclax) is administered at a dosage of about 100 mg once daily. In one embodiment, the BCL2 inhibitor (e.g., venetoclax) is administered at a dosage of about 200 mg once daily. In one embodiment, the BCL2 inhibitor (e.g., venetoclax) is administered at a dosage of about 400 mg once daily. In one embodiment, the BCL2 inhibitor (e.g., venetoclax) is administered at a dosage of about 500 mg once daily. In one embodiment, the BCL2 inhibitor (e.g., venetoclax) is administered at a dosage of about 600 mg once daily. In one embodiment, the BCL2 inhibitor (e.g., venetoclax) is administered at a dosage of about 20 mg once daily in Week 1, about 50 mg once daily in Week 2, about 100 mg once daily in Week 3, about 200 mg once daily in Week 4, and about 400 mg once daily in Week 5 and beyond. In one embodiment, the BCL2 inhibitor (e.g., venetoclax) is administered orally.

In one embodiment, the second active agent used in the methods provided herein is a BTK inhibitor. In one embodiment, the BTK inhibitor (e.g., ibrutinib) is administered at a dosage of in the range of from about 140 mg to about 700 mg, from about 280 mg to about 560 mg, or from about 420 mg to about 560 mg once daily. In one embodiment, the BTK inhibitor (e.g., ibrutinib) is administered at a dosage of no more than about 700 mg, no more than about 560 mg, no more than about 420 mg, no more than about 280 mg, or no more than about 140 mg once daily. In one embodiment, the BTK inhibitor (e.g., ibrutinib) is administered at a dosage of about 560 mg once daily. In one embodiment, the BTK inhibitor (e.g., ibrutinib) is administered at a dosage of about 420 mg once daily. In one embodiment, the BTK inhibitor (e.g., ibrutinib) is administered at a dosage of about 280 mg once daily. In one embodiment, the BTK inhibitor (e.g., ibrutinib) is administered at a dosage of about 140 mg once daily. In one embodiment, the BTK inhibitor (e.g., ibrutinib) is administered orally.

In one embodiment, the second active agent used in the methods provided herein is an mTOR inhibitor. In one embodiment, the mTOR inhibitor (e.g., everolimus) is administered at a dosage of in the range of from about 1 mg to about 20 mg, from about 2.5 mg to about 15 mg, or from about 5 mg to about 10 mg once daily. In one embodiment, the mTOR inhibitor (e.g., everolimus) is administered at a dosage of no more than about 20 mg, no more than about 15 mg, no more than about 10 mg, no more than about 5 mg, or no more than about 2.5 mg once daily. In one embodiment, the mTOR inhibitor (e.g., everolimus) is administered at a dosage of about 10 mg once daily. In one embodiment, the mTOR inhibitor (e.g., everolimus) is administered at a dosage of about 5 mg once daily. In one embodiment, the mTOR inhibitor (e.g., everolimus) is administered at a dosage of about 2.5 mg once daily. In one embodiment, the mTOR inhibitor (e.g., everolimus) is administered orally.

In one embodiment, the second active agent used in the methods provided herein is a PI3K inhibitor. In one embodiment, the PI3K inhibitor (e.g., idelalisib) is administered at a dosage of in the range of from about 50 mg to about 300 mg, or from about 100 mg to about 200 mg twice daily. In one embodiment, the PI3K inhibitor (e.g., idelalisib) is administered at a dosage of no more than about 300 mg, no more than about 200 mg, no more than about 150 mg, no more than about 100 mg, or no more than about 50 mg twice daily. In one embodiment, the PI3K inhibitor (e.g., idelalisib) is administered at a dosage of about 50 mg twice daily. In one embodiment, the PI3K inhibitor (e.g., idelalisib) is administered at a dosage of about 100 mg twice daily. In one embodiment, the PI3K inhibitor (e.g., idelalisib) is administered at a dosage of about 150 mg twice daily. In one embodiment, the PI3K inhibitor (e.g., idelalisib) is administered at a dosage of about 200 mg twice daily. In one embodiment, the PI3K inhibitor (e.g., idelalisib) is administered at a dosage of about 300 mg twice daily. In one embodiment, the PI3K inhibitor (e.g., idelalisib) is administered orally.

In one embodiment, the second active agent used in the methods provided herein is a PKCβ inhibitor. In one embodiment, the PKCβ inhibitor (e.g., enzastaurin or a hydrochloride salt of enzastaurin) is administered at a dosage of in the range of from about 250 mg to about 1250 mg, from about 500 mg to about 1125 mg, or from about 400 mg to about 600 mg per day. In one embodiment, the PKCβ inhibitor (e.g., enzastaurin or a hydrochloride salt of enzastaurin) is administered at a dosage of no more than about 1250 mg, no more than about 1125 mg, no more than about 1000 mg, no more than about 750 mg, no more than about 600 mg, no more than about 500 mg, no more than about 400 mg, or no more than about 250 mg per day. In one embodiment, the PKCβ inhibitor (e.g., enzastaurin or a hydrochloride salt of enzastaurin) is administered at a dosage of about 1250 mg per day. In one embodiment, the PKCβ inhibitor (e.g., enzastaurin or a hydrochloride salt of enzastaurin) is administered at a dosage of about 1125 mg per day. In one embodiment, the PKCβ inhibitor (e.g., enzastaurin or a hydrochloride salt of enzastaurin) is administered at a dosage of about 1000 mg per day. In one embodiment, the PKCβ inhibitor (e.g., enzastaurin or a hydrochloride salt of enzastaurin) is administered at a dosage of about 750 mg per day. In one embodiment, the PKC inhibitor (e.g., enzastaurin or a hydrochloride salt of enzastaurin) is administered at a dosage of about 600 mg per day. In one embodiment, the PKCβ inhibitor (e.g., enzastaurin or a hydrochloride salt of enzastaurin) is administered at a dosage of about 500 mg per day. In one embodiment, the PKCβ inhibitor (e.g., enzastaurin or a hydrochloride salt of enzastaurin) is administered at a dosage of about 400 mg per day. In one embodiment, the PKCβ inhibitor (e.g., enzastaurin or a hydrochloride salt of enzastaurin) is administered at a dosage of about 250 mg per day. In one embodiment, the PKCβ inhibitor (e.g., enzastaurin or a hydrochloride salt of enzastaurin) is administered at an initial dosage of about 1125 mg for one day, followed by a dosage of about 500 mg per day (on days thereafter). In one embodiment, the PKCβ inhibitor (e.g., enzastaurin or a hydrochloride salt of enzastaurin) is administered orally.

In one embodiment, the second active agent used in the methods provided herein is a SYK inhibitor. In one embodiment, the SYK inhibitor (e.g., fostamatinib or fostamatinib disodium hexahydrate) is administered at a dosage of in the range of from about 50 mg to about 250 mg, from about 75 mg to about 200 mg, or from about 100 mg to about 150 mg twice daily. In one embodiment, the SYK inhibitor (e.g., fostamatinib or fostamatinib disodium hexahydrate) is administered at a dosage of no more than about 250 mg, no more than about 200 mg, no more than about 150 mg, no more than about 125 mg, no more than about 100 mg, no more than about 75 mg, or no more than about 50 mg twice daily. In one embodiment, the SYK inhibitor (e.g., fostamatinib or fostamatinib disodium hexahydrate) is administered at a dosage of about 250 mg twice daily. In one embodiment, the SYK inhibitor (e.g., fostamatinib or fostamatinib disodium hexahydrate) is administered at a dosage of about 200 mg twice daily. In one embodiment, the SYK inhibitor (e.g., fostamatinib or fostamatinib disodium hexahydrate) is administered at a dosage of about 150 mg twice daily. In one embodiment, the SYK inhibitor (e.g., fostamatinib or fostamatinib disodium hexahydrate) is administered at a dosage of about 125 mg twice daily. In one embodiment, the SYK inhibitor (e.g., fostamatinib or fostamatinib disodium hexahydrate) is administered at a dosage of about 100 mg twice daily. In one embodiment, the SYK inhibitor (e.g., fostamatinib or fostamatinib disodium hexahydrate) is administered at a dosage of about 75 mg twice daily. In one embodiment, the SYK inhibitor (e.g., fostamatinib or fostamatinib disodium hexahydrate) is administered at a dosage of about 50 mg twice daily. In one embodiment, the SYK inhibitor (e.g., fostamatinib or fostamatinib disodium hexahydrate) is administered at a dosage of about 100 mg twice daily for 4 weeks, followed by a dosage of about 150 mg twice daily (on days thereafter). In one embodiment, the SYK inhibitor (e.g., fostamatinib or fostamatinib disodium hexahydrate) is administered orally.

In one embodiment, the second active agent used in the methods provided herein is a JAK2 inhibitor.

In one embodiment, the JAK2 inhibitor (e.g., fedratinib) is administered at a dosage of in the range of from about 120 mg to about 680 mg, from about 240 mg to about 500 mg, or from about 300 mg to about 400 mg once daily. In one embodiment, the JAK2 inhibitor (e.g., fedratinib) is administered at a dosage of no more than about 680 mg, no more than about 500 mg, no more than about 400 mg, no more than about 300 mg, or no more than about 240 mg once daily. In one embodiment, the JAK2 inhibitor (e.g., fedratinib) is administered at a dosage of about 500 mg once daily. In one embodiment, the JAK2 inhibitor (e.g., fedratinib) is administered at a dosage of about 400 mg once daily. In one embodiment, the JAK2 inhibitor (e.g., fedratinib) is administered at a dosage of about 300 mg once daily. In one embodiment, the JAK2 inhibitor (e.g., fedratinib) is administered orally.

In one embodiment, the JAK2 inhibitor (e.g., pacritinib) is administered at a dosage of in the range of from about 50 mg to about 400 mg, or from about 100 mg to about 300 mg twice daily. In one embodiment, the JAK2 inhibitor (e.g., pacritinib) is administered at a dosage of no more than about 400 mg, no more than about 300 mg, no more than about 200 mg, no more than about 100 mg, or no more than about 150 mg twice daily. In one embodiment, the JAK2 inhibitor (e.g., pacritinib) is administered at a dosage of about 400 mg twice daily. In one embodiment, the JAK2 inhibitor (e.g., pacritinib) is administered at a dosage of about 300 mg twice daily. In one embodiment, the JAK2 inhibitor (e.g., pacritinib) is administered at a dosage of about 200 mg twice daily. In one embodiment, the JAK2 inhibitor (e.g., pacritinib) is administered at a dosage of about 100 mg twice daily. In one embodiment, the JAK2 inhibitor (e.g., pacritinib) is administered at a dosage of about 50 mg twice daily. In one embodiment, the JAK2 inhibitor (e.g., pacritinib) is administered orally.

In one embodiment, the JAK2 inhibitor (e.g., ruxolitinib or ruxolitinib phosphate) is administered at a dosage of in the range of from about 5 mg to about 30 mg, from about 10 mg to about 25 mg, or from about 15 mg to about 20 mg twice daily. In one embodiment, the JAK2 inhibitor (e.g., ruxolitinib or ruxolitinib phosphate) is administered at a dosage of no more than about 30 mg, no more than about 25 mg, no more than about 20 mg, no more than about 15 mg, no more than about 10 mg, or no more than about 5 mg twice daily. In one embodiment, the JAK2 inhibitor (e.g., ruxolitinib or ruxolitinib phosphate) is administered at a dosage of about 30 mg twice daily. In one embodiment, the JAK2 inhibitor (e.g., ruxolitinib or ruxolitinib phosphate) is administered at a dosage of about 25 mg twice daily. In one embodiment, the JAK2 inhibitor (e.g., ruxolitinib or ruxolitinib phosphate) is administered at a dosage of about 20 mg twice daily. In one embodiment, the JAK2 inhibitor (e.g., ruxolitinib or ruxolitinib phosphate) is administered at a dosage of about 15 mg twice daily. In one embodiment, the JAK2 inhibitor (e.g., ruxolitinib or ruxolitinib phosphate) is administered at a dosage of about 10 mg twice daily. In one embodiment, the JAK2 inhibitor (e.g., ruxolitinib or ruxolitinib phosphate) is administered at a dosage of about 5 mg twice daily. In one embodiment, the JAK2 inhibitor (e.g., ruxolitinib or ruxolitinib phosphate) is administered orally.

In one embodiment, the second active agent used in the methods provided herein is an Aurora kinase inhibitor. In one embodiment, the Aurora kinase A inhibitor (e.g., alisertib) is administered at a dosage of in the range of from about 5 mg to about 70 mg, from about 10 mg to about 60 mg, from about 20 mg to about 50 mg, or from about 30 mg to about 40 mg twice daily. In one embodiment, the Aurora kinase A inhibitor (e.g., alisertib) is administered at a dosage of no more than about 70 mg, no more than about 60 mg, no more than about 50 mg, no more than about 40 mg, no more than about 30 mg, no more than about 20 mg, no more than about 10 mg, or no more than about 5 mg twice daily. In one embodiment, the Aurora kinase A inhibitor (e.g., alisertib) is administered at a dosage of about 70 mg twice daily. In one embodiment, the Aurora kinase A inhibitor (e.g., alisertib) is administered at a dosage of about 60 mg twice daily. In one embodiment, the Aurora kinase A inhibitor (e.g., alisertib) is administered at a dosage of about 50 mg twice daily. In one embodiment, the Aurora kinase A inhibitor (e.g., alisertib) is administered at a dosage of about 40 mg twice daily. In one embodiment, the Aurora kinase A inhibitor (e.g., alisertib) is administered at a dosage of about 30 mg twice daily. In one embodiment, the Aurora kinase A inhibitor (e.g., alisertib) is administered at a dosage of about 20 mg twice daily. In one embodiment, the Aurora kinase A inhibitor (e.g., alisertib) is administered at a dosage of about 10 mg twice daily. In one embodiment, the Aurora kinase A inhibitor (e.g., alisertib) is administered at a dosage of about 5 mg twice daily. In one embodiment, the Aurora kinase A inhibitor (e.g., alisertib) is administered orally.

In one embodiment, the Aurora kinase inhibitor (e.g., AZD1152) is administered at a dosage of in the range of from about 50 mg to about 200 mg, from about 75 mg to about 150 mg, or from about 100 mg to about 110 mg per day. In one embodiment, the Aurora kinase inhibitor (e.g., AZD1152) is administered at a dosage of no more than about 200 mg, no more than about 150 mg, no more than about 110 mg, no more than about 100 mg, no more than about 75 mg, or no more than about 50 mg per day. In one embodiment, the Aurora kinase inhibitor (e.g., AZD1152) is administered at a dosage of about 200 mg, about 150 mg, about 110 mg, about 100 mg, about 75 mg, or about 50 mg per day. In one embodiment, the Aurora kinase inhibitor (e.g., AZD1152) is administered at a dosage described herein on days 1, 2, 15, and 16 of a 28-day cycle. In one embodiment, the Aurora kinase inhibitor (e.g., AZD1152) is administered intravenously. In one embodiment, the Aurora kinase inhibitor (e.g., AZD1152) is administered at a dosage of about 150 mg as a 48-hour continuous infusion every 14 days out of a 28-day cycle. In one embodiment, the Aurora kinase inhibitor (e.g., AZD1152) is administered at a dosage of about 220 mg as 2×2-hour infusions every 14 days out of a 28-day cycle (e.g., 110 mg/day on days 1, 2, 15, and 16). In one embodiment, the Aurora kinase inhibitor (e.g., AZD1152) is administered at a dosage of about 200 mg as a 2-hour infusion every 7 days. In one embodiment, the Aurora kinase inhibitor (e.g., AZD1152) is administered at a dosage of about 450 mg as a 2-hour infusion every 14 days.

In one embodiment, the second active agent used in the methods provided herein is an EZH2 inhibitor.

In one embodiment, the EZH2 inhibitor (e.g., tazemetostat) is administered at a dosage of in the range of from about 50 mg to about 1600 mg, from about 100 mg to about 800 mg, or from about 200 mg to about 400 mg twice daily. In one embodiment, the EZH2 inhibitor (e.g., tazemetostat) is administered at a dosage of no more than about 800 mg, no more than about 600 mg, no more than about 400 mg, no more than about 200 mg, or no more than about 100 mg twice daily. In one embodiment, the EZH2 inhibitor (e.g., tazemetostat) is administered at a dosage of about 800 mg twice daily. In one embodiment, the EZH2 inhibitor (e.g., tazemetostat) is administered at a dosage of about 600 mg twice daily. In one embodiment, the EZH2 inhibitor (e.g., tazemetostat) is administered at a dosage of about 400 mg twice daily. In one embodiment, the EZH2 inhibitor (e.g., tazemetostat) is administered at a dosage of about 200 mg twice daily. In one embodiment, the EZH2 inhibitor (e.g., tazemetostat) is administered orally.

In one embodiment, the EZH2 inhibitor (e.g., GSK126) is administered at a dosage of in the range of from about 50 mg to about 3000 mg, from about 100 mg to about 2400 mg, from about 200 mg to about 1800 mg, or from about 400 mg to about 1200 mg twice weekly. In one embodiment, the EZH2 inhibitor (e.g., GSK126) is administered at a dosage of no more than about 3000 mg, no more than about 2400 mg, no more than about 1800 mg, no more than about 1200 mg, no more than about 800 mg, no more than about 400 mg, no more than about 200 mg, no more than about 100 mg, or no more than about 50 mg twice weekly. In one embodiment, the EZH2 inhibitor (e.g., GSK126) is administered at a dosage of about 3000 mg twice weekly. In one embodiment, the EZH2 inhibitor (e.g., GSK126) is administered at a dosage of about 2400 mg twice weekly. In one embodiment, the EZH2 inhibitor (e.g., GSK126) is administered at a dosage of about 1800 mg twice weekly. In one embodiment, the EZH2 inhibitor (e.g., GSK126) is administered at a dosage of about 1200 mg twice weekly. In one embodiment, the EZH2 inhibitor (e.g., GSK126) is administered at a dosage of about 800 mg twice weekly. In one embodiment, the EZH2 inhibitor (e.g., GSK126) is administered at a dosage of about 400 mg twice weekly. In one embodiment, the EZH2 inhibitor (e.g., GSK126) is administered at a dosage of about 200 mg twice weekly. In one embodiment, the EZH2 inhibitor (e.g., GSK126) is administered at a dosage of about 100 mg twice weekly. In one embodiment, the EZH2 inhibitor (e.g., GSK126) is administered at a dosage of about 50 mg twice weekly. In one embodiment, the EZH2 inhibitor (e.g., GSK126) is administered intravenously.

In one embodiment, the EZH2 inhibitor (e.g., CPI-1205) is administered at a dosage of in the range of from about 100 mg to about 3200 mg, from about 200 mg to about 1600 mg, or from about 400 mg to about 800 mg twice daily. In one embodiment, the EZH2 inhibitor (e.g., CPI-1205) is administered at a dosage of no more than about 3200 mg, no more than about 1600 mg, no more than about 800 mg, no more than about 400 mg, no more than about 200 mg, or no more than about 100 mg twice daily. In one embodiment, the EZH2 inhibitor (e.g., CPI-1205) is administered at a dosage of about 3200 mg twice daily. In one embodiment, the EZH2 inhibitor (e.g., CPI-1205) is administered at a dosage of about 1600 mg twice daily. In one embodiment, the EZH2 inhibitor (e.g., CPI-1205) is administered at a dosage of about 800 mg twice daily. In one embodiment, the EZH2 inhibitor (e.g., CPI-1205) is administered at a dosage of about 400 mg twice daily. In one embodiment, the EZH2 inhibitor (e.g., CPI-1205) is administered at a dosage of about 200 mg twice daily. In one embodiment, the EZH2 inhibitor (e.g., CPI-1205) is administered at a dosage of about 100 mg twice daily. In one embodiment, the EZH2 inhibitor (e.g., CPI-1205) is administered for one or more 28-day cycles. In one embodiment, the EZH2 inhibitor (e.g., CPI-1205) is administered orally.

In one embodiment, the second active agent used in the methods provided herein is an BET inhibitor. In one embodiment, the BET inhibitor (e.g., birabresib) is administered at a dosage of in the range of from about 10 mg to about 160 mg, from about 20 mg to about 120 mg, or from about 40 mg to about 80 mg once daily. In one embodiment, the BET inhibitor (e.g., birabresib) is administered at a dosage of no more than about 160 mg, no more than about 120 mg, no more than about 80 mg, no more than about 40 mg, no more than about 20 mg, or no more than about 10 mg once daily. In one embodiment, the BET inhibitor (e.g., birabresib) is administered at a dosage of about 160 mg once daily. In one embodiment, the BET inhibitor (e.g., birabresib) is administered at a dosage of about 120 mg once daily. In one embodiment, the BET inhibitor (e.g., birabresib) is administered at a dosage of about 80 mg once daily. In one embodiment, the BET inhibitor (e.g., birabresib) is administered at a dosage of about 40 mg once daily. In one embodiment, the BET inhibitor (e.g., birabresib) is administered at a dosage of about 20 mg once daily. In one embodiment, the BET inhibitor (e.g., birabresib) is administered at a dosage of about 10 mg once daily. In one embodiment, the BET inhibitor (e.g., birabresib) is administered at a dosage described herein on Days 1 to 7 of a 21-day cycle. In one embodiment, the BET inhibitor (e.g., birabresib) is administered at a dosage described herein on Days 1 to 14 of a 21-day cycle. In one embodiment, the BET inhibitor (e.g., birabresib) is administered at a dosage described herein on Days 1 to 21 of a 21-day cycle. In one embodiment, the BET inhibitor (e.g., birabresib) is administered at a dosage described herein on Days 1 to 5 of a 7-day cycle. In one embodiment, the BET inhibitor (e.g., birabresib) is administered orally.

In one embodiment, the second active agent used in the methods provided herein is a hypomethylating agent.

In one embodiment, the hypomethylating agent (e.g., 5-azacytidine) is administered at a dosage of in the range of from about 25 mg/m$^2$ to about 150 mg/m$^2$, from about 50 mg/m$^2$ to about 125 mg/m$^2$, or from about 75 mg/m$^2$ to about 100 mg/m$^2$ daily. In one embodiment, the hypomethylating agent (e.g., 5-azacytidine) is administered at a dosage of no more than about 150 mg/m$^2$, no more than about 125 mg/m$^2$, no more than about 100 mg/m$^2$, no more than about 75 mg/m$^2$, no more than about 50 mg/m$^2$, or no more than about 25 mg/m$^2$ daily. In one embodiment, the hypomethylating agent (e.g., 5-azacytidine) is administered at a dosage of about 150 mg/m$^2$ daily. In one embodiment, the hypomethylating agent (e.g., 5-azacytidine) is administered at a dosage of about 125 mg/m$^2$ daily. In one embodiment, the hypomethylating agent (e.g., 5-azacytidine) is administered at a dosage of about 100 mg/m$^2$ daily. In one embodiment, the hypomethylating agent (e.g., 5-azacytidine) is administered at a dosage of about 75 mg/m$^2$ daily. In one embodiment, the hypomethylating agent (e.g., 5-azacytidine) is administered at a dosage of about 50 mg/m$^2$ daily. In one embodiment, the hypomethylating agent (e.g., 5-azacytidine) is administered at a dosage of about 25 mg/m$^2$ daily. In one embodiment, the hypomethylating agent (e.g., 5-azacytidine) is administered subcutaneously. In one embodiment, the hypomethylating agent (e.g., 5-azacytidine) is administered intravenously.

In one embodiment, the hypomethylating agent (e.g., 5-azacytidine) is administered at a dosage of in the range of from about 100 mg to about 500 mg, or from about 200 mg to about 400 mg once daily. In one embodiment, the hypomethylating agent (e.g., 5-azacytidine) is administered at a dosage of no more than about 500 mg, no more than about 400 mg, no more than about 300 mg, no more than about 200 mg, or no more than about 100 mg once daily. In one embodiment, the hypomethylating agent (e.g., 5-azacytidine) is administered at a dosage of about 500 mg once daily. In one embodiment, the hypomethylating agent (e.g., 5-azacytidine) is administered at a dosage of about 400 mg once daily. In one embodiment, the hypomethylating agent (e.g., 5-azacytidine) is administered at a dosage of about 300 mg once daily. In one embodiment, the hypomethylating agent (e.g., 5-azacytidine) is administered at a dosage of about 200 mg once daily. In one embodiment, the hypomethylating agent (e.g., 5-azacytidine) is administered at a dosage of about 100 mg once daily. In one embodiment, the hypomethylating agent (e.g., 5-azacytidine) is administered at a dosage of in the range of from about 100 mg to about 300 mg, or from about 150 mg to about 250 mg twice daily. In one embodiment, the hypomethylating agent (e.g., 5-azacytidine) is administered at a dosage of no more than about 300 mg, no more than about 250 mg, no more than about 200 mg, no more than about 150 mg, or no more than about 100 mg twice daily. In one embodiment, the hypomethylating agent (e.g., 5-azacytidine) is administered at a dosage of about 300 mg twice daily. In one embodiment, the hypomethylating agent (e.g., 5-azacytidine) is administered at a dosage of about 250 mg twice daily. In one embodiment, the hypomethylating agent (e.g., 5-azacytidine) is administered at a dosage of about 200 mg twice daily. In one embodiment, the hypomethylating agent (e.g., 5-azacytidine) is administered at a dosage of about 150 mg twice daily. In one embodiment, the hypomethylating agent (e.g., 5-azacytidine) is administered at a dosage of about 100 mg twice daily. In one embodiment, the hypomethylating agent (e.g., 5-azacytidine) is administered at a dosage described herein on Days 1 to 14 of a 28-day cycle. In one embodiment, the hypomethylating agent (e.g., 5-azacytidine) is administered at a dosage described herein on Days 1 to 21 of a 28-day cycle. In one embodiment, the hypomethylating agent (e.g., 5-azacytidine) is administered orally.

In one embodiment, the hypomethylating agent (e.g., decitabine) is administered at a dosage of in the range of from about 5 mg/m$^2$ to about 30 mg/m$^2$, from about 10 mg/m$^2$ to about 25 mg/m$^2$, or from about 15 mg/m$^2$ to about 20 mg/m$^2$. In one embodiment, the hypomethylating agent (e.g., decitabine) is administered at a dosage of no more than about 30 mg/m$^2$, no more than about 25 mg/m$^2$, no more than about 20 mg/m$^2$, no more than about 15 mg/m$^2$, no more than about 10 mg/m$^2$, or no more than about 5 mg/m$^2$. In one embodiment, the hypomethylating agent (e.g., decitabine) is administered at a dosage of about 30 mg/m$^2$. In one embodiment, the hypomethylating agent (e.g., decitabine) is administered at a dosage of about 25 mg/m$^2$. In one embodiment, the hypomethylating agent (e.g., decitabine) is administered at a dosage of about 20 mg/m$^2$. In one embodiment, the hypomethylating agent (e.g., decitabine) is administered at a dosage of about 15 mg/m$^2$. In one embodiment, the hypomethylating agent (e.g., decitabine) is administered at a dosage of about 10 mg/m$^2$. In one embodiment, the hypomethylating agent (e.g., decitabine) is administered at a dosage of about 5 mg/m$^2$. In one embodiment, the hypomethylating agent (e.g., decitabine) is administered at a dosage described herein over 3 hours repeated every 8 hours for 3 days. In one embodiment, the hypomethylating agent (e.g., decitabine) is administered at a dosage described herein over 1 hour repeated daily for 5 days. In one embodiment, the hypomethylating agent (e.g., decitabine) is administered at a dosage of about 15 mg/m$^2$ over 3 hours repeated every 8 hours for 3 days. In one embodiment, the hypomethylating agent (e.g., decitabine) is administered at a dosage of about 20 mg/m$^2$ over 1 hour repeated daily for 5 days. In one embodiment, the hypomethylating agent (e.g., decitabine) is administered subcutaneously. In one embodiment, the hypomethylating agent (e.g., decitabine) is administered intravenously.

In one embodiment, the second active agent used in the methods provided herein is a DOT1L inhibitor. In one embodiment, the DOT1L inhibitor (e.g., SGC0946) is administered at a dosage of in the range of from about 10 mg to about 500 mg, from about 25 mg to about 400 mg, from about 50 mg to about 300 mg, from about 75 mg to about 200 mg, or from about 100 mg to about 150 mg per day. In one embodiment, the DOT1L inhibitor (e.g., SGC0946) is administered at a dosage of no more than about 500 mg, no more than about 400 mg, no more than about 300 mg, no more than about 200 mg, no more than about 150 mg, no more than about 100 mg, no more than about 75 mg, no more than about 50 mg, or no more than about 25 mg per day. In one embodiment, the DOT1L inhibitor (e.g., SGC0946) is administered at a dosage of about 25 mg, about 50 mg, about 75 mg, about 100 mg, about 150 mg, about 200 mg, about 300 mg, about 400 mg, or about 500 mg. In one embodiment, the DOT1L inhibitor (e.g., SGC0946) is administered at a dosage of in the range of from about 18 mg/m$^2$ to about 126 mg/m$^2$, from about 36 mg/m$^2$ to about 108 mg/m$^2$, or from about 54 mg/m$^2$ to about 90 mg/m$^2$ per day. In one embodiment, the DOT1L inhibitor (e.g., SGC0946) is administered at a dosage of no more than about 126 mg/m$^2$, no more than about 108 mg/m$^2$, no more than about 90 mg/m$^2$, no more than about 72 mg/m$^2$, no more than about 54 mg/m$^2$, no more than about 36 mg/m$^2$, or no more than about 18 mg/m$^2$ per day. In one embodiment, the DOT1L inhibitor (e.g., SGC0946) is administered at a dosage of about 18 mg/m², about 36 mg/m², about 54 mg/m², about 72 mg/m², about 90 mg/m², about 108 mg/m², or about 126 mg/m² per day. In one embodiment, the DOT1L inhibitor (e.g., SGC0946) is administered orally. In one embodiment, the DOT1L inhibitor (e.g., SGC0946) is administered intravenously.

In one embodiment, the DOT1L inhibitor (e.g., pinometostat) is administered at a dosage of in the range of from about 18 mg/m² to about 108 mg/m², from about 36 mg/m² to about 90 mg/m², or from about 54 mg/m² to about 72 mg/m² per day. In one embodiment, the DOT1L inhibitor (e.g., pinometostat) is administered at a dosage of no more than about 108 mg/m², no more than about 90 mg/m², no more than about 72 mg/m², no more than about 54 mg/m², no more than about 36 mg/m², or no more than about 18 mg/m² per day. In one embodiment, the DOT1L inhibitor (e.g., pinometostat) is administered at a dosage of about 18 mg/m² per day. In one embodiment, the DOT1L inhibitor (e.g., pinometostat) is administered at a dosage of about 36 mg/m² per day. In one embodiment, the DOT1L inhibitor (e.g., pinometostat) is administered at a dosage of about 54 mg/m² per day. In one embodiment, the DOT1L inhibitor (e.g., pinometostat) is administered at a dosage of about 70 mg/m² per day. In one embodiment, the DOT1L inhibitor (e.g., pinometostat) is administered at a dosage of about 72 mg/m² per day. In one embodiment, the DOT1L inhibitor (e.g., pinometostat) is administered at a dosage of about 90 mg/m² per day. In one embodiment, the DOT1L inhibitor (e.g., pinometostat) is administered at a dosage of about 108 mg/m² per day. In one embodiment, the DOT1L inhibitor (e.g., pinometostat) is administered intravenously.

In one embodiment, the second active agent used in the methods provided herein is a PLK1 inhibitor. In one embodiment, the PLK1 inhibitor (e.g., BI2536) is administered at a dosage of in the range of from about 20 mg to about 200 mg, from about 40 mg to about 100 mg, or from about 50 mg to about 60 mg per day. In one embodiment, the PLK1 inhibitor (e.g., BI2536) is administered at a dosage of no more than about 200 mg, no more than about 100 mg, no more than about 60 mg, no more than about 50 mg, no more than about 40 mg, or no more than about 20 mg per day. In one embodiment, the PLK1 inhibitor (e.g., BI2536) is administered at a dosage of about 200 mg, about 100 mg, about 60 mg, about 50 mg, about 40 mg, or about 20 mg per day. In one embodiment, the PLK1 inhibitor (e.g., BI2536) is administered at a dosage of about 200 mg once every 21-day cycle. In one embodiment, the PLK1 inhibitor (e.g., BI2536) is administered at a dosage of about 100 mg per day on days 1 and 8 of 21-day cycle. In one embodiment, the PLK1 inhibitor (e.g., BI2536) is administered at a dosage of about 50 mg per day on days 1 to 3 of 21-day cycle. In one embodiment, the PLK1 inhibitor (e.g., BI2536) is administered at a dosage of about 60 mg per day on days 1 to 3 of 21-day cycle. In one embodiment, the PLK1 inhibitor (e.g., BI2536) is administered intravenously.

In one embodiment, the second active agent used in the methods provided herein is an MEK inhibitor. In one embodiment, the MEK inhibitor (e.g., trametinib or trametinib dimethyl sulfoxide) is administered at a dosage of in the range of from about 0.25 mg to about 3 mg, from about 0.5 mg to about 2 mg, or from about 1 mg to about 1.5 mg once daily. In one embodiment, the MEK inhibitor (e.g., trametinib or trametinib dimethyl sulfoxide) is administered at a dosage of no more than about 2 mg, no more than about 1.5 mg, no more than about 1 mg, or no more than about 0.5 mg once daily. In one embodiment, the MEK inhibitor (e.g., trametinib or trametinib dimethyl sulfoxide) is administered at a dosage of about 2 mg once daily. In one embodiment, the MEK inhibitor (e.g., trametinib or trametinib dimethyl sulfoxide) is administered at a dosage of about 1.5 mg once daily. In one embodiment, the MEK inhibitor (e.g., trametinib or trametinib dimethyl sulfoxide) is administered at a dosage of about 1 mg once daily. In one embodiment, the MEK inhibitor (e.g., trametinib or trametinib dimethyl sulfoxide) is administered at a dosage of about 0.5 mg once daily. In one embodiment, the MEK inhibitor (e.g., trametinib or trametinib dimethyl sulfoxide) is administered orally.

In one embodiment, the second active agent used in the methods provided herein is a PIM inhibitor. In one embodiment, the PIM inhibitor (e.g., LGH-447) is administered at a dosage of in the range of from about 30 mg to about 1000 mg, from about 70 mg to about 700 mg, from about 150 mg to about 500 mg, from about 200 mg to about 350 mg, or from about 250 mg to about 300 mg once daily. In one embodiment, the PIM inhibitor (e.g., LGH-447) is administered at a dosage of no more than about 700 mg, no more than about 500 mg, no more than about 350 mg, no more than about 300 mg, no more than about 250 mg, no more than about 200 mg, no more than about 150 mg, or no more than about 70 mg once daily. In one embodiment, the PIM inhibitor (e.g., LGH-447) is administered at a dosage of about 500 mg once daily. In one embodiment, the PIM inhibitor (e.g., LGH-447) is administered at a dosage of about 350 mg once daily. In one embodiment, the PIM inhibitor (e.g., LGH-447) is administered at a dosage of about 300 mg once daily. In one embodiment, the PIM inhibitor (e.g., LGH-447) is administered at a dosage of about 250 mg once daily. In one embodiment, the PIM inhibitor (e.g., LGH-447) is administered at a dosage of about 200 mg once daily. In one embodiment, the PIM inhibitor (e.g., LGH-447) is administered at a dosage of about 150 mg once daily. In one embodiment, the PIM inhibitor (e.g., LGH-447) is administered orally.

In one embodiment, the second active agent used in the methods provided herein is an IGF-1R inhibitor. In one embodiment, the IGF-1R inhibitor (e.g., linsitinib) is administered at a dosage of in the range of from about 100 mg to about 500 mg, from about 150 mg to about 450 mg, from about 200 mg to about 400 mg, or from about 250 mg to about 300 mg daily. In one embodiment, the IGF-1R inhibitor (e.g., linsitinib) is administered at a dosage of in the range of from about 50 mg to about 250 mg, from about 75 mg to about 225 mg, from about 100 mg to about 200 mg, or from about 125 mg to about 150 mg twice daily (BID). In one embodiment, the IGF-1R inhibitor (e.g., linsitinib) is administered at a dosage of no more than about 450 mg, no more than about 400 mg, no more than about 300 mg, no more than about 250 mg, no more than about 200 mg, or no more than about 150 mg daily. In one embodiment, the IGF-1R inhibitor (e.g., linsitinib) is administered at a dosage of no more than about 450 mg, no more than about 400 mg, no more than about 300 mg, no more than about 250 mg, no more than about 200 mg, or no more than about 150 mg daily. In one embodiment, the IGF-1R inhibitor (e.g., linsitinib) is administered at a dosage of no more than about 225 mg, no more than about 200 mg, no more than about 150 mg, no more than about 125 mg, no more than about 100 mg, or no more than about 75 mg twice daily. In one embodiment, the IGF-1R inhibitor (e.g., linsitinib) is administered at a dosage of about 450 mg, about 400 mg, about 300 mg, about 250 mg, about 200 mg, or about 150 mg daily. In one embodiment, the IGF-1R inhibitor (e.g., linsitinib) is administered at a dosage of about 225 mg, about 200 mg, about 150 mg, about 125 mg, about 100 mg, or about 75 mg twice daily. In one embodiment, the IGF-1R inhibitor (e.g., linsitinib) is administered on days 1 to 3 every 7 days. In one embodiment, the IGF-1R inhibitor (e.g., linsitinib) is administered orally.

In one embodiment, the second active agent used in the methods provided herein is an XPO1 inhibitor. In one embodiment, the XPO1 inhibitor (e.g., selinexor) is administered at a dosage of in the range of from about 30 mg to about 200 mg twice weekly, from about 45 mg to about 150 mg twice weekly, or from about 60 mg to about 100 mg twice weekly. In one embodiment, the XPO1 inhibitor (e.g., selinexor) is administered at a dosage of no more than about 100 mg, no more than about 80 mg, no more than about 60 mg, or no more than about 40 mg twice weekly. In one embodiment, the XPO1 inhibitor (e.g., selinexor) is administered at a dosage of about 20 mg, about 30 mg, about 40 mg, about 50 mg, about 60 mg, about 70 mg, about 80 mg, about 90 mg, or about 100 mg twice weekly. In one embodiment, the dosage is about 40 mg twice weekly. In one embodiment, the dosage is about 60 mg twice weekly. In one embodiment, the dosage is about 80 mg twice weekly. In one embodiment, the dosage is about 100 mg twice weekly. In one embodiment, the XPO1 inhibitor (e.g., selinexor) is administered orally.

In one embodiment, the second active agent used in the methods provided herein is a BIRC5 inhibitor. In one embodiment, the BIRC5 inhibitor (e.g., YM155) is administered at a dosage of in the range of from about 2 mg/m$^2$ to about 15 mg/m$^2$, or from about 4 mg/m$^2$ to about 10 mg/m$^2$ per day. In one embodiment, the BIRC5 inhibitor (e.g., YM155) is administered at a dosage of no more than about 15 mg/m$^2$, no more than about 10 mg/m$^2$, no more than about 4.8 mg/m$^2$, no more than about 4 mg/m$^2$, or no more than about 2 mg/m$^2$ per day. In one embodiment, the BIRC5 inhibitor (e.g., YM155) is administered at a dosage of about 15 mg/m$^2$ per day. In one embodiment, the BIRC5 inhibitor (e.g., YM155) is administered at a dosage of about 10 mg/m$^2$ per day. In one embodiment, the BIRC5 inhibitor (e.g., YM155) is administered at a dosage of about 4.8 mg/m$^2$ per day. In one embodiment, the BIRC5 inhibitor (e.g., YM155) is administered at a dosage of about 4 mg/m$^2$ per day. In one embodiment, the BIRC5 inhibitor (e.g., YM155) is administered at a dosage of about 2 mg/m$^2$ per day. In one embodiment, the BIRC5 inhibitor (e.g., YM155) is administered intravenously. In one embodiment, the BIRC5 inhibitor (e.g., YM155) is administered at a dosage of about 4.8 mg/m$^2$/day by about 168 hours continuous IV infusion every 3 weeks. In one embodiment, the BIRC5 inhibitor (e.g., YM155) is administered at a dosage of about 5 mg/m$^2$/day by about 168 hours continuous IV infusion every 3 weeks. In one embodiment, the BIRC5 inhibitor (e.g., YM155) is administered at a dosage of about 10 mg/m$^2$/day by about 72 hours continuous IV infusion every 3 weeks.

In one embodiment, the second active agent used in the methods provided herein is a chemotherapy.

In one embodiment, the chemotherapy (e.g., bendamustine or bendamustine hydrochloride) is administered at a dosage of in the range of from about 25 mg/m$^2$ to about 200 mg/m$^2$, or from about 50 mg/m$^2$ to about 150 mg/m$^2$. In one embodiment, the chemotherapy (e.g., bendamustine or bendamustine hydrochloride) is administered at a dosage of no more than about 200 mg/m$^2$, no more than about 150 mg/m$^2$, no more than about 100 mg/m$^2$, no more than about 50 mg/m$^2$, or no more than about 25 mg/m$^2$. In one embodiment, the chemotherapy (e.g., bendamustine or bendamustine hydrochloride) is administered at a dosage of about 200 mg/m$^2$. In one embodiment, the chemotherapy (e.g., bendamustine or bendamustine hydrochloride) is administered at a dosage of about 150 mg/m$^2$. In one embodiment, the chemotherapy (e.g., bendamustine or bendamustine hydrochloride) is administered at a dosage of about 100 mg/m$^2$. In one embodiment, the chemotherapy (e.g., bendamustine or bendamustine hydrochloride) is administered at a dosage of about 50 mg/m$^2$. In one embodiment, the chemotherapy (e.g., bendamustine or bendamustine hydrochloride) is administered at a dosage of about 25 mg/m$^2$. In one embodiment, the chemotherapy (e.g., bendamustine or bendamustine hydrochloride) is administered at a dosage described herein over 30 minutes on Days 1 and 2 of a 28-day cycle. In one embodiment, the chemotherapy (e.g., bendamustine or bendamustine hydrochloride) is administered intravenously.

In one embodiment, the chemotherapy (e.g., doxorubicin or doxorubicin hydrochloride) is administered at a dosage of in the range of from about 10 mg/m$^2$ to about 50 mg/m$^2$, or from about 20 mg/m$^2$ to about 40 mg/m$^2$. In one embodiment, the chemotherapy (e.g., doxorubicin or doxorubicin hydrochloride) is administered at a dosage of no more than about 50 mg/m$^2$, no more than about 40 mg/m$^2$, no more than about 30 mg/m$^2$, no more than about 20 mg/m$^2$, or no more than about 10 mg/m$^2$. In one embodiment, the chemotherapy (e.g., doxorubicin or doxorubicin hydrochloride) is administered at a dosage of about 50 mg/m$^2$. In one embodiment, the chemotherapy (e.g., doxorubicin or doxorubicin hydrochloride) is administered at a dosage of about 40 mg/m$^2$. In one embodiment, the chemotherapy (e.g., doxorubicin or doxorubicin hydrochloride) is administered at a dosage of about 30 mg/m$^2$. In one embodiment, the chemotherapy (e.g., doxorubicin or doxorubicin hydrochloride) is administered at a dosage of about 20 mg/m$^2$. In one embodiment, the chemotherapy (e.g., doxorubicin or doxorubicin hydrochloride) is administered at a dosage of about 10 mg/m$^2$. In one embodiment, the chemotherapy (e.g., doxorubicin or doxorubicin hydrochloride) is administered at a dosage described herein over 60 minutes on day 4 of a 21-day cycle. In one embodiment, the chemotherapy (e.g., doxorubicin or doxorubicin hydrochloride) is administered at a dosage of about 30 mg/m$^2$ over 60 minutes on day 4 of a 21-day cycle. In one embodiment, the chemotherapy (e.g., doxorubicin or doxorubicin hydrochloride) is administered intravenously.

In one embodiment, the chemotherapy (e.g., etoposide or etoposide phosphate) is administered at a dosage of in the range of from about 10 mg/m$^2$ to about 150 mg/m$^2$, from about 25 mg/m$^2$ to about 125 mg/m$^2$, from about 35 mg/m$^2$ to about 50 mg/m$^2$, or from about 50 mg/m$^2$ to about 100 mg/m$^2$. In one embodiment, the chemotherapy (e.g., etoposide or etoposide phosphate) is administered at a dosage of no more than about 150 mg/m$^2$, no more than about 125 mg/m$^2$, no more than about 100 mg/m$^2$, no more than about 50 mg/m$^2$, no more than about 35 mg/m$^2$, no more than about 25 mg/m$^2$, or no more than about 10 mg/m$^2$. In one embodiment, the chemotherapy (e.g., etoposide or etoposide phosphate) is administered at a dosage of about 150 mg/m$^2$. In one embodiment, the chemotherapy (e.g., etoposide or etoposide phosphate) is administered at a dosage of about 125 mg/m$^2$. In one embodiment, the chemotherapy (e.g., etoposide or etoposide phosphate) is administered at a dosage of about 100 mg/m$^2$. In one embodiment, the chemotherapy (e.g., etoposide or etoposide phosphate) is administered at a dosage of about 50 mg/m$^2$. In one embodiment, the chemotherapy (e.g., etoposide or etoposide phosphate) is administered at a dosage of about 35 mg/m². In one embodiment, the chemotherapy (e.g., etoposide or etoposide phosphate) is administered at a dosage of about 25 mg/m². In one embodiment, the chemotherapy (e.g., etoposide or etoposide phosphate) is administered at a dosage of about 10 mg/m². In one embodiment, the chemotherapy (e.g., etoposide or etoposide phosphate) is administered at a dosage described herein over 5 minutes to 3.5 hours on days 1 through 5 of a 21-day or 28-day cycle. In one embodiment, the chemotherapy (e.g., etoposide or etoposide phosphate) is administered at a dosage described herein over 5 minutes to 3.5 hours on days 1, 3, and 5 of a 21-day or 28-day cycle. In one embodiment, the chemotherapy (e.g., etoposide or etoposide phosphate) is administered at a dosage described herein over 5 minutes to 3.5 hours for 4 days. In one embodiment, the chemotherapy (e.g., etoposide or etoposide phosphate) is administered at a dosage described herein over 5 minutes to 3.5 hours for 5 days. In one embodiment, the chemotherapy (e.g., etoposide or etoposide phosphate) is administered intravenously. In one embodiment, the chemotherapy (e.g., etoposide or etoposide phosphate) is administered orally.

In one embodiment, the chemotherapy (e.g., methotrexate or methotrexate sodium) is administered at a dosage of in the range of from about 5 mg/m² to about 60 mg/m², from about 10 mg/m² to about 50 mg/m², or from about 20 mg/m² to about 40 mg/m². In one embodiment, the chemotherapy (e.g., methotrexate or methotrexate sodium) is administered at a dosage of in the range of from about 3 g/m² to about 3.5 g/m². In one embodiment, the chemotherapy (e.g., methotrexate or methotrexate sodium) is administered at a dosage of no more than about 3.5 g/m², no more than about 3 g/m², no more than about 60 mg/m², no more than about 50 mg/m², no more than about 40 mg/m², no more than about 30 mg/m², no more than about 20 mg/m², no more than about 10 mg/m², or no more than about 5 mg/m². In one embodiment, the chemotherapy (e.g., methotrexate or methotrexate sodium) is administered at a dosage of about 3.5 g/m². In one embodiment, the chemotherapy (e.g., methotrexate or methotrexate sodium) is administered at a dosage of about 3 g/m². In one embodiment, the chemotherapy (e.g., methotrexate or methotrexate sodium) is administered at a dosage of about 60 mg/m². In one embodiment, the chemotherapy (e.g., methotrexate or methotrexate sodium) is administered at a dosage of about 50 mg/m². In one embodiment, the chemotherapy (e.g., methotrexate or methotrexate sodium) is administered at a dosage of about 40 mg/m². In one embodiment, the chemotherapy (e.g., methotrexate or methotrexate sodium) is administered at a dosage of about 30 mg/m². In one embodiment, the chemotherapy (e.g., methotrexate or methotrexate sodium) is administered at a dosage of about 20 mg/m². In one embodiment, the chemotherapy (e.g., methotrexate or methotrexate sodium) is administered at a dosage of about 10 mg/m². In one embodiment, the chemotherapy (e.g., methotrexate or methotrexate sodium) is administered at a dosage of about 5 mg/m². In one embodiment, the chemotherapy (e.g., methotrexate or methotrexate sodium) is administered at a dosage described herein once weekly. In one embodiment, the once weekly dosage is administered as divided dosages multiple times a week. In one embodiment, the chemotherapy (e.g., methotrexate or methotrexate sodium) is administered intravenously. In one embodiment, the chemotherapy (e.g., methotrexate or methotrexate sodium) is administered orally. In one embodiment, the chemotherapy (e.g., methotrexate or methotrexate sodium) is administered intrathecally (intraventricular or lumbar puncture).

In one embodiment, the chemotherapy (e.g., cytarabine) is administered at a dosage of in the range of from about 30 mg to about 70 mg, or from about 40 mg to about 60 mg. In one embodiment, the chemotherapy (e.g., cytarabine) is administered at a dosage of no more than about 70 mg, no more than about 60 mg, no more than about 50 mg, no more than about 40 mg, or no more than about 30 mg. In one embodiment, the chemotherapy (e.g., cytarabine) is administered at a dosage of about 70 mg. In one embodiment, the chemotherapy (e.g., cytarabine) is administered at a dosage of about 60 mg. In one embodiment, the chemotherapy (e.g., cytarabine) is administered at a dosage of about 50 mg. In one embodiment, the chemotherapy (e.g., cytarabine) is administered at a dosage of about 40 mg. In one embodiment, the chemotherapy (e.g., cytarabine) is administered at a dosage of about 30 mg. In one embodiment, the chemotherapy (e.g., cytarabine) is administered at a dosage described herein once every 14 days. In one embodiment, the chemotherapy (e.g., cytarabine) is administered at a dosage described herein once every 28 days. In one embodiment, the chemotherapy (e.g., cytarabine) is administered intrathecally (intraventricular or lumbar puncture).

In one embodiment, the chemotherapy (e.g., vincristine or vincristine sulfate) is administered at a dosage of in the range of from about 1 mg/m² to about 4 mg/m², from about 1.5 mg/m² to about 3 mg/m², or from about 2 mg/m² to about 2.5 mg/m². In one embodiment, the chemotherapy (e.g., vincristine or vincristine sulfate) is administered at a dosage of no more than about 4 mg/m², no more than about 3 mg/m², no more than about 2.5 mg/m², no more than about 2.25 mg/m², no more than about 2 mg/m², no more than about 1.5 mg/m², or no more than about 1 mg/m². In one embodiment, the chemotherapy (e.g., vincristine or vincristine sulfate) is administered at a dosage of about 4 mg/m². In one embodiment, the chemotherapy (e.g., vincristine or vincristine sulfate) is administered at a dosage of about 3 mg/m². In one embodiment, the chemotherapy (e.g., vincristine or vincristine sulfate) is administered at a dosage of about 2.5 mg/m². In one embodiment, the chemotherapy (e.g., vincristine or vincristine sulfate) is administered at a dosage of about 2.25 mg/m². In one embodiment, the chemotherapy (e.g., vincristine or vincristine sulfate) is administered at a dosage of about 2 mg/m². In one embodiment, the chemotherapy (e.g., vincristine or vincristine sulfate) is administered at a dosage of about 1.5 mg/m². In one embodiment, the chemotherapy (e.g., vincristine or vincristine sulfate) is administered at a dosage of about 1 mg/m². In one embodiment, the chemotherapy (e.g., vincristine or vincristine sulfate) is administered at a dosage described herein over 1 hour once every 7 days. In one embodiment, the chemotherapy (e.g., vincristine or vincristine sulfate) is administered at a dosage of about 2.25 mg/m² over 1 hour once every 7 days. In one embodiment, the chemotherapy (e.g., vincristine or vincristine sulfate) is administered intravenously.

In one embodiment, the chemotherapy (e.g., ifosfamide) is administered at a dosage of in the range of from about 0.5 mg/m² to about 2 mg/m², from about 0.8 mg/m² to about 1.6 mg/m², or from about 1 mg/m² to about 1.4 mg/m² per day. In one embodiment, the chemotherapy (e.g., ifosfamide) is administered at a dosage of no more than about 2 mg/m², no more than about 1.6 mg/m², no more than about 1.4 mg/m², no more than about 1.2 mg/m², no more than about 1 mg/m², no more than about 0.8 mg/m², or no more than about 0.5 mg/m² per day. In one embodiment, the chemotherapy (e.g., ifosfamide) is administered at a dosage of about 2 mg/m² per day. In one embodiment, the chemotherapy (e.g., ifosfamide) is administered at a dosage of about 1.6 mg/m² per day. In one embodiment, the chemotherapy (e.g., ifosfamide) is administered at a dosage of about 1.4 mg/m² per day. In one embodiment, the chemotherapy (e.g., ifosfamide) is administered at a dosage of about 1.2 mg/m² per day. In one embodiment, the chemotherapy (e.g., ifosfamide) is administered at a dosage of about 1 mg/m² per day. In one embodiment, the chemotherapy (e.g., ifosfamide) is administered at a dosage of about 0.8 mg/m² per day. In one embodiment, the chemotherapy (e.g., ifosfamide) is administered at a dosage of about 0.5 mg/m² per day. In one embodiment, the chemotherapy (e.g., ifosfamide) is administered intravenously.

In one embodiment, the chemotherapy (e.g., melphalan or melphalan hydrochloride) is administered at a dosage of in the range of from about 50 mg/m² to about 150 mg/m², or from about 75 mg/m² to about 125 mg/m² per day. In one embodiment, the chemotherapy (e.g., melphalan or melphalan hydrochloride) is administered at a dosage of no more than about 150 mg/m², no more than about 125 mg/m², no more than about 100 mg/m², no more than about 75 mg/m², or no more than about 50 mg/m² per day. In one embodiment, the chemotherapy (e.g., melphalan or melphalan hydrochloride) is administered at a dosage of about 150 mg/m² per day. In one embodiment, the chemotherapy (e.g., melphalan or melphalan hydrochloride) is administered at a dosage of about 125 mg/m² per day. In one embodiment, the chemotherapy (e.g., melphalan or melphalan hydrochloride) is administered at a dosage of about 100 mg/m² per day. In one embodiment, the chemotherapy (e.g., melphalan or melphalan hydrochloride) is administered at a dosage of about 75 mg/m² per day. In one embodiment, the chemotherapy (e.g., melphalan or melphalan hydrochloride) is administered at a dosage of about 50 mg/m² per day. In one embodiment, the chemotherapy (e.g., melphalan or melphalan hydrochloride) is administered intravenously.

In one embodiment, the chemotherapy (e.g., melphalan or melphalan hydrochloride) is administered at a dosage of in the range of from about 2 mg to about 10 mg, or from about 4 mg to about 8 mg per day. In one embodiment, the chemotherapy (e.g., melphalan or melphalan hydrochloride) is administered at a dosage of no more than about 10 mg, no more than about 8 mg, no more than about 6 mg, no more than about 4 mg, or no more than about 2 mg per day. In one embodiment, the chemotherapy (e.g., melphalan or melphalan hydrochloride) is administered at a dosage of about 10 mg per day. In one embodiment, the chemotherapy (e.g., melphalan or melphalan hydrochloride) is administered at a dosage of about 8 mg per day. In one embodiment, the chemotherapy (e.g., melphalan or melphalan hydrochloride) is administered at a dosage of about 6 mg per day. In one embodiment, the chemotherapy (e.g., melphalan or melphalan hydrochloride) is administered at a dosage of about 4 mg per day. In one embodiment, the chemotherapy (e.g., melphalan or melphalan hydrochloride) is administered at a dosage of about 2 mg per day. In one embodiment, the chemotherapy (e.g., melphalan or melphalan hydrochloride) is administered orally.

In one embodiment, the chemotherapy (e.g., oxaliplatin) is administered at a dosage of in the range of from about 50 mg/m² to about 100 mg/m², or from about 65 mg/m² to about 85 mg/m² per day. In one embodiment, the chemotherapy (e.g., oxaliplatin) is administered at a dosage of no more than about 100 mg/m², no more than about 85 mg/m², no more than about 75 mg/m², no more than about 65 mg/m², or no more than about 50 mg/m² per day. In one embodiment, the chemotherapy (e.g., oxaliplatin) is administered at a dosage of about 100 mg/m² per day. In one embodiment, the chemotherapy (e.g., oxaliplatin) is administered at a dosage of about 85 mg/m² per day. In one embodiment, the chemotherapy (e.g., oxaliplatin) is administered at a dosage of about 75 mg/m² per day. In one embodiment, the chemotherapy (e.g., oxaliplatin) is administered at a dosage of about 65 mg/m² per day. In one embodiment, the chemotherapy (e.g., oxaliplatin) is administered at a dosage of about 50 mg/m² per day. In one embodiment, the chemotherapy (e.g., oxaliplatin) is administered intravenously.

In one embodiment, the chemotherapy (e.g., dexamethasone) is administered at a dosage of from about 0.5 to about 2,000 mg per day, from about 1 to about 1,000 mg per day, from about 1 to about 500 mg per day, from about 1 to about 250 mg per day, from about 5 to about 250 mg per day, from about 7.5 to about 250 mg per day, from about 10 to about 250 mg per day, from about 20 to about 250 mg per day, from about 20 to about 200 mg per day, from about 1 to about 100 mg per day, from about 1 to about 50 mg per day, from about 0.5 to about 25 mg per day, or from about 0.5 to about 10 mg per day. In one embodiment, the chemotherapy (e.g., dexamethasone) is administered at a dosage of from about 0.5 to about 2,000 mg per day. In one embodiment, the chemotherapy (e.g., dexamethasone) is administered at a dosage of from about 1 to about 1,000 mg per day. In one embodiment, the chemotherapy (e.g., dexamethasone) is administered at a dosage of from about 1 to about 500 mg per day. In one embodiment, the chemotherapy (e.g., dexamethasone) is administered at a dosage of from about 1 to about 250 mg per day. In one embodiment, the chemotherapy (e.g., dexamethasone) is administered at a dosage of from about 5 to about 250 mg per day. In one embodiment, the chemotherapy (e.g., dexamethasone) is administered at a dosage of from about 7.5 to about 250 mg per day. In one embodiment, the chemotherapy (e.g., dexamethasone) is administered at a dosage of from about 10 to about 250 mg per day. In one embodiment, the chemotherapy (e.g., dexamethasone) is administered at a dosage of from about 20 to about 250 mg per day. In one embodiment, the chemotherapy (e.g., dexamethasone) is administered at a dosage of from about 20 to about 200 mg per day. In one embodiment, the chemotherapy (e.g., dexamethasone) is administered at a dosage of from about 1 to about 100 mg per day. In one embodiment, the chemotherapy (e.g., dexamethasone) is administered at a dosage of from about 1 to about 50 mg per day. In one embodiment, the chemotherapy (e.g., dexamethasone) is administered at a dosage of from about 0.5 to about 25 mg per day. In one embodiment, the chemotherapy (e.g., dexamethasone) is administered at a dosage of from about 0.5 to about 10 mg per day.

In one embodiment, the chemotherapy (e.g., dexamethasone) is administered at a dosage of about 0.5, about 1, about 2, about 5, about 10, about 15, about 20, about 25, about 30, about 40, about 45, about 50, about 60, about 70, about 80, about 90, about 100, about 150, or about 200 mg per day. In one embodiment, the chemotherapy (e.g., dexamethasone) is administered at a dosage of about 0.5 mg per day. In one embodiment, the chemotherapy (e.g., dexamethasone) is administered at a dosage of about 1 mg per day. In one embodiment, the chemotherapy (e.g., dexamethasone) is administered at a dosage of about 2 mg per day. In one embodiment, the chemotherapy (e.g., dexamethasone) is administered at a dosage of about 5 mg per day. In one embodiment, the chemotherapy (e.g., dexamethasone) is administered at a dosage of about 10 mg per day. In one embodiment, the chemotherapy (e.g., dexamethasone) is administered at a dosage of about 15 mg per day. In one embodiment, the chemotherapy (e.g., dexamethasone) is administered at a dosage of about 20 mg per day. In one embodiment, the chemotherapy (e.g., dexamethasone) is administered at a dosage of about 25 mg per day. In one embodiment, the chemotherapy (e.g., dexamethasone) is administered at a dosage of about 30 mg per day. In one embodiment, the chemotherapy (e.g., dexamethasone) is administered at a dosage of about 40 mg per day. In one embodiment, the chemotherapy (e.g., dexamethasone) is administered at a dosage of about 45 mg per day. In one embodiment, the chemotherapy (e.g., dexamethasone) is administered at a dosage of about 50 mg per day. In one embodiment, the chemotherapy (e.g., dexamethasone) is administered at a dosage of about 60 mg per day. In one embodiment, the chemotherapy (e.g., dexamethasone) is administered at a dosage of about 70 mg per day. In one embodiment, the chemotherapy (e.g., dexamethasone) is administered at a dosage of about 80 mg per day. In one embodiment, the chemotherapy (e.g., dexamethasone) is administered at a dosage of about 90 mg per day. In one embodiment, the chemotherapy (e.g., dexamethasone) is administered at a dosage of about 100 mg per day. In one embodiment, the chemotherapy (e.g., dexamethasone) is administered at a dosage of about 150 mg per day. In one embodiment, the chemotherapy (e.g., dexamethasone) is administered at a dosage of about 200 mg per day.

In one embodiment, the recommended daily dose range of the chemotherapy (e.g., dexamethasone) for the conditions described herein lie within the range of from about 0.5 mg to about 100 mg per day, preferably given as a single once-a-day dose, or in divided doses throughout a day. In some embodiments, the dosage ranges from about 1 mg to about 100 mg per day. In other embodiments, the dosage ranges from about 0.5 to about 20 mg per day. Specific doses include 0.5, 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 60, 70, 80, 90 or 100 mg per day.

In some embodiments, the chemotherapy (e.g., dexamethasone) is administered at a 4 mg dose on days 1 and 8 of a 21 day cycle. In some other embodiments, the chemotherapy (e.g., dexamethasone) is administered at a 4 mg dose on days 1, 4, 8 and 11 of a 21 day cycle. In some embodiments, the chemotherapy (e.g., dexamethasone) is administered at a 4 mg dose on days 1, 8, and 15 of a 28 day cycle. In some other embodiments, the chemotherapy (e.g., dexamethasone) is administered at a 4 mg dose on days 1, 4, 8, 11, 15 and 18 of a 28 day cycle. In some embodiments, the chemotherapy (e.g., dexamethasone) is administered at a 4 mg dose on days 1, 8, 15, and 22 of a 28 day cycle. In one such embodiment, the chemotherapy (e.g., dexamethasone) is administered at a 4 mg dose on days 1, 10, 15, and 22 of Cycle 1. In some embodiments, the chemotherapy (e.g., dexamethasone) is administered at a 4 mg dose on days 1, 3, 15, and 17 of a 28 day cycle. In one such embodiment, the chemotherapy (e.g., dexamethasone) is administered at a 4 mg dose on days 1, 3, 14, and 17 of Cycle 1.

In some other embodiments, the chemotherapy (e.g., dexamethasone) is administered at a 8 mg dose on days 1 and 8 of a 21 day cycle. In some other embodiments, the chemotherapy (e.g., dexamethasone) is administered at a 8 mg dose on days 1, 4, 8 and 11 of a 21 day cycle. In some embodiments, the chemotherapy (e.g., dexamethasone) is administered at a 8 mg dose on days 1, 8, and 15 of a 28 day cycle. In some other embodiments, the chemotherapy (e.g., dexamethasone) is administered at a 8 mg dose on days 1, 4, 8, 11, 15 and 18 of a 28 day cycle. In some embodiments, the chemotherapy (e.g., dexamethasone) is administered at a 8 mg dose on days 1, 8, 15, and 22 of a 28 day cycle. In one such embodiment, the chemotherapy (e.g., dexamethasone) is administered at a 8 mg dose on days 1, 10, 15, and 22 of Cycle 1. In some embodiments, the chemotherapy (e.g., dexamethasone) is administered at a 8 mg dose on days 1, 3, 15, and 17 of a 28 day cycle. In one such embodiment, the chemotherapy (e.g., dexamethasone) is administered at a 8 mg dose on days 1, 3, 14, and 17 of Cycle 1.

In some embodiments, the chemotherapy (e.g., dexamethasone) is administered at a 10 mg dose on days 1 and 8 of a 21 day cycle. In some other embodiments, the chemotherapy (e.g., dexamethasone) is administered at a 10 mg dose on days 1, 4, 8 and 11 of a 21 day cycle. In some embodiments, the chemotherapy (e.g., dexamethasone) is administered at a 10 mg dose on days 1, 8, and 15 of a 28 day cycle. In some other embodiments, the chemotherapy (e.g., dexamethasone) is administered at a 10 mg dose on days 1, 4, 8, 11, 15 and 18 of a 28 day cycle. In some embodiments, the chemotherapy (e.g., dexamethasone) is administered at a 10 mg dose on days 1, 8, 15, and 22 of a 28 day cycle. In one such embodiment, the chemotherapy (e.g., dexamethasone) is administered at a 10 mg dose on days 1, 10, 15, and 22 of Cycle 1. In some embodiments, the chemotherapy (e.g., dexamethasone) is administered at a 10 mg dose on days 1, 3, 15, and 17 of a 28 day cycle. In one such embodiment, the chemotherapy (e.g., dexamethasone) is administered at a 10 mg dose on days 1, 3, 14, and 17 of Cycle 1.

In some embodiments, the chemotherapy (e.g., dexamethasone) is administered at a 20 mg dose on days 1 and 8 of a 21 day cycle. In some other embodiments, the chemotherapy (e.g., dexamethasone) is administered at a 20 mg dose on days 1, 4, 8 and 11 of a 21 day cycle. In some embodiments, the chemotherapy (e.g., dexamethasone) is administered at a 20 mg dose on days 1, 8, and 15 of a 28 day cycle. In some other embodiments, the chemotherapy (e.g., dexamethasone) is administered at a 20 mg dose on days 1, 4, 8, 11, 15 and 18 of a 28 day cycle. In some embodiments, the chemotherapy (e.g., dexamethasone) is administered at a 20 mg dose on days 1, 8, 15, and 22 of a 28 day cycle. In one such embodiment, the chemotherapy (e.g., dexamethasone) is administered at a 20 mg dose on days 1, 10, 15, and 22 of Cycle 1. In some embodiments, the chemotherapy (e.g., dexamethasone) is administered at a 20 mg dose on days 1, 3, 15, and 17 of a 28 day cycle. In one such embodiment, the chemotherapy (e.g., dexamethasone) is administered at a 20 mg dose on days 1, 3, 14, and 17 of Cycle 1.

In some embodiments, the chemotherapy (e.g., dexamethasone) is administered at a 40 mg dose on days 1 and 8 of a 21 day cycle. In some other embodiments, the chemotherapy (e.g., dexamethasone) is administered at a 40 mg dose on days 1, 4, 8 and 11 of a 21 day cycle. In some embodiments, the chemotherapy (e.g., dexamethasone) is administered at a 40 mg dose on days 1, 8, and 15 of a 28 day cycle. In one such embodiment, the chemotherapy (e.g., dexamethasone) is administered at a 40 mg dose on days 1, 10, 15, and 22 of Cycle 1. In some other embodiments, the chemotherapy (e.g., dexamethasone) is administered at a 40 mg dose on days 1, 4, 8, 11, 15 and 18 of a 28 day cycle. In other such embodiments, the chemotherapy (e.g., dexamethasone) is administered at a 40 mg dose on days 1, 8, 15, and 22 of a 28 day cycle. In other such embodiments, the chemotherapy (e.g., dexamethasone) is administered at a 40 mg dose on days 1, 3, 15, and 17 of a 28 day cycle. In one such embodiment, the chemotherapy (e.g., dexamethasone) is administered at a 40 mg dose on days 1, 3, 14, and 17 of Cycle 1.

6. EXAMPLES

Certain embodiments of the invention are illustrated by the following non-limiting examples.

Abbreviations Used

| | |
|---|---|
| DCM | Dichloromethane |
| DIEA | N,N-Diisopropylethylamine |
| DMSO | Dimethylsulfoxide |
| ESI | Electrospray ionization |
| EtOAc | Ethyl acetate |
| LCMS | Liquid chromatography mass spectrometry |
| MeOH | Methanol |
| MS | Mass spectrometry |
| NMP | N-Methylpyrrolidone |
| NMR | Nuclear magnetic resonance |

6.1 Synthesis of (S)-2-(2,6-dioxopiperidin-3-yl)-4-((2-fluoro-4-((3-morpholinoazetidin-1-yl)methyl)benzyl)amino)isoindoline-1,3-dione (Compound 1)

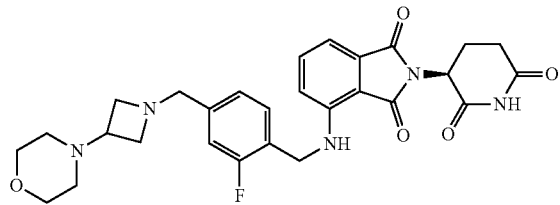 [SMILES: O=C1CC[C@H](N2C(=O)c3cccc(NCc4ccc(CN5CC(N6CCOCC6)C5)cc4F)c3C2=O)C(=O)N1]

(S)-2-(2,6-Dioxopiperidin-3-yl)-4-((2-fluoro-4-(hydroxymethyl)benzyl)amino)isoindoline-1,3-dione: A suspension of (S)-4-amino-2-(2,6-dioxopiperidin-3-yl)isoindoline-1,3-dione (5.00 g, 18.3 mmol) and 2-fluoro-4-(hydroxymethyl)benzaldehyde (2.82 g, 18.30 mmol) in 2:1 dioxane-MeOH (75 mL) was cooled to 0° C. and $B_{10}H_{14}$ (4.92 g, 40.3 mmol) was added in small portions over 5 minutes. The reaction flask was fitted with a septum and needle vent (pressure) and vigorously stirred for 10 minutes. The mixture was allowed to reach ambient temperature and stirred for 3 hours. The mixture was concentrated and the residue purified by silica gel chromatography (0-10% MeOH-DCM) to provide (S)-2-(2,6-dioxopiperidin-3-yl)-4-((2-fluoro-4-(hydroxymethyl)benzyl)amino)isoindoline-1,3-dione as a yellow solid (4.23 g, 56%). LCMS (ESI) m/z 411.8 [M+H]+.

(S)-4-((4-(Chloromethyl)-2-fluorobenzyl)amino)-2-(2,6-dioxopiperidin-3-yl)isoindoline-1,3-dione: A solution of (S)-2-(2,6-dioxopiperidin-3-yl)-4-((2-fluoro-4-(hydroxymethyl)benzyl)amino)isoindoline-1,3-dione (0.727 g, 1.77 mmol) in dry NMP (6 mL) was cooled to 0° C. and methane sulfonyl chloride (0.275 mL, 3.35 mmol) and DIEA (0.617 mL, 3.53 mmol) were added sequentially. The reaction mixture was allowed to reach ambient temperature and was stirred for 18 hours. The reaction mixture was slowly added to H₂O (60 mL) cooled to 0° C. with vigorous mixing. The resulting suspension was filtered and the collected solid was washed with H₂O and Et₂O. The solid was dissolved in EtOAc and the solution dried with MgSO₄, filtered and concentrated to provide (S)-4-((4-(chloromethyl)-2-fluorobenzyl)amino)-2-(2,6-dioxopiperidin-3-yl)isoindoline-1,3-dione as a yellow solid (0.600 g, 79%). LCMS (ESI) m/z 430.0 [M+H]+.

(S)-2-(2,6-Dioxopiperidin-3-yl)-4-((2-fluoro-4-((3-morpholinoazetidin-1-yl)methyl)benzyl)amino)isoindoline-1,3-dione: To a solution of (S)-4-((4-(chloromethyl)-2-fluorobenzyl)amino)-2-(2,6-dioxopiperidin-3-yl)isoindoline-1,3-dione (300 mg, 0.698 mmol) in dry DMSO (1.0 mL) was added 4-(azetidin-3-yl)morpholine hydrochloride (125 mg, 0.698 mmol) and DIEA (0.122 mL, 0.698 mmol). The reaction mixture was stirred at ambient temperature for 18 hours and was diluted with DMSO (1 mL). The solution was purified by chiral reverse-phase chromatography to give (S)-2-(2,6-dioxopiperidin-3-yl)-4-((2-fluoro-4-((3-morpholinoazetidin-1-yl)methyl)benzyl)amino)isoindoline-1,3-dione (89 mg, 24%, 97% ee). LCMS (ESI) m/z 536.2 [M+H]$^+$.

6.2 Effect of Treatment with Compound 1 in Combination with Second Active Agents on Proliferation of Cell Lines from Hematological Malignancies A combination study was performed to evaluate the effects on proliferation as a result of treatment with a combination of Compound 1 with compounds tested in hematological malignancies clinically or pre-clinically, based on their mechanism of action, including the following: HDAC inhibitor (panobinostat, romidepsin, and vorinostat), BCL2 inhibitor (venetoclax), BTK inhibitor (ibrutinib), mTOR inhibitor (everolimus), PI3K inhibitor (idelalisib), PKCβ inhibitor (enzastaurin), SYK inhibitor (fostamatinib), JAK2 inhibitor (fedratinib, pacritinib/SB1518, and ruxolitinib), Aurora kinase A inhibitor (alisertib), EZH2 inhibitor (tazemetostat, GSK126, and CPI-1205), BET inhibitor (birabresib and Compound B), hypomethylating agent (5-azacytidine and decitabine), and chemotherapy (bendamustine, doxorubicin, etoposide, methotrexate, cytarabine, vincristine, ifosfamide, melphalan, oxaliplatin, and dexamethasone). Other epigenetic compounds were also tested in this combination study with Compound 1, including DOT1L inhibitor (pinometostat), HAT inhibitor (C646), WDR5 inhibitor (OICR-9429), HDAC6 inhibitor (ACY-241), DNMT1 selective inhibitor (GSK3484862), LSD-1 inhibitor (Compound C), G9A inhibitor (UNC 0631), PRMT5 inhibitor (GSK3326595), BRD9/7 inhibitor (LP99), SUV420H1/H2 inhibitor (A-196), CARM1 inhibitor (EZM2302).

Cell Lines/Cells: Activated B-Cell (ABC) cell lines: TMD-8, SU-DHL-2, OCI-Ly10, RIVA, U2932; and Germinal Center B-cell (GCB) cell lines: SU-DHL10, Pfeiffer, WSU-DLCL2, SU-DHL4, DB; myeloma cell lines: H929, JJN3 and SK-MM1; acute myeloid leukemia cell line: HNT-34; acute lymphocytic leukemia cell line: Karpas-231; other lymphoma cell lines: Daudi, Karpas-299, HuT-102, L-428.

Experimental Procedures: The concentrations of Compound 1 used in the dose response curves (DRC) were selected on the basis of the sensitivity of the cell line in antiproliferative assays. U2932, SU-DHL4, Pfeiffer, RIVA, DB, Daudi, H-929, HNT-34, JJN3, Karpas-299, Karpas-231, HuT-102, L-428 and SK-MM1 were treated at high Compound 1 starting concentrations (starting at 10 M); TMD-8, SU-DHL2, SU-DHL10, WSU-DLCL2, and OCI-Ly10 were treated at low Compound 1 concentrations (starting at 1 M).

All Compound 1 solutions were serially diluted in 3-fold steps for a 10-point dilution curve. Alternatively, combination compound solutions were serially diluted from 5 M starting concentration and serially diluted 6-fold for a 6-point dilution curve. Compounds were plated in a 384-well plate where Compound 1 was dispensed in rows and the combination compound agent in columns. The same concentration of Compound 1 or combination compound was distributed amongst its row or column respectively to create a matrix of compound combinations. Cells were added to each well and cultured for 3 days. For some epigenetic compounds (tazemetostat, GSK126, CPI-1205, 5-azacytidine and decitabine), cells were pretreated for 4 days with the epigenetic compound before starting treatment with Compound 1. After those 4 days, cells were treated with the combination of Compound 1 and the epigenetic agents, as previously described for the other compounds. For some other epigenetic agents (EPZ5676, C646, OICR-9429, ACY-241, GSK3484862, Compound C, UNC 0631, GSK3326595, LP99, A-196, CARM1 EZM2302) cells were cultured for 5 days due to their mechanism of action.

Cell Preparation and Treatment: Compound 1 was dispensed in 384-well plates and frozen at −80° C. until the start of the experiment. Plates were either made at a concentration of 10 M or 1 M diluted 3-fold for a 10-point dilution curve, with a final DMSO concentration of 0.2%. All cell line solutions were diluted to a concentration of 100,000 cells/mL and added to each well in a volume of 50 L, with the exception of SU-DHL-6 solution, which was diluted to 25,000 cells/mL. At the end of the treatment period cells were lysed with Cell Titer Glo (CTG) reagents following manufacture recommendation. Luminescent signal was read using an Envision and data was normalized by DMSO for data analysis.

Data Analysis: The combination effect was analyzed by combining results from Highest Single Agent (HSA) and Bliss Independency methods. See, e.g., Foucquier J, Guedj M., Analysis of drug combinations: current methodological landscape. *Pharmacol Res* Perspect. 2015; 3(3):e00149. doi:10.1002/prp2.149.

Results: Effect of treatment with a combination of Compound 1 with 43 compounds was evaluated by CTG after 3 and 5 days of co-treatment of 19 cell lines from hematological malignancies, including DLBCL cell lines with different sensitivity to Compound 1 (FIG. 1). Combined results of HSA and Bliss scores were used to define synergistic and additive effect of the combinations.

Figure 2:
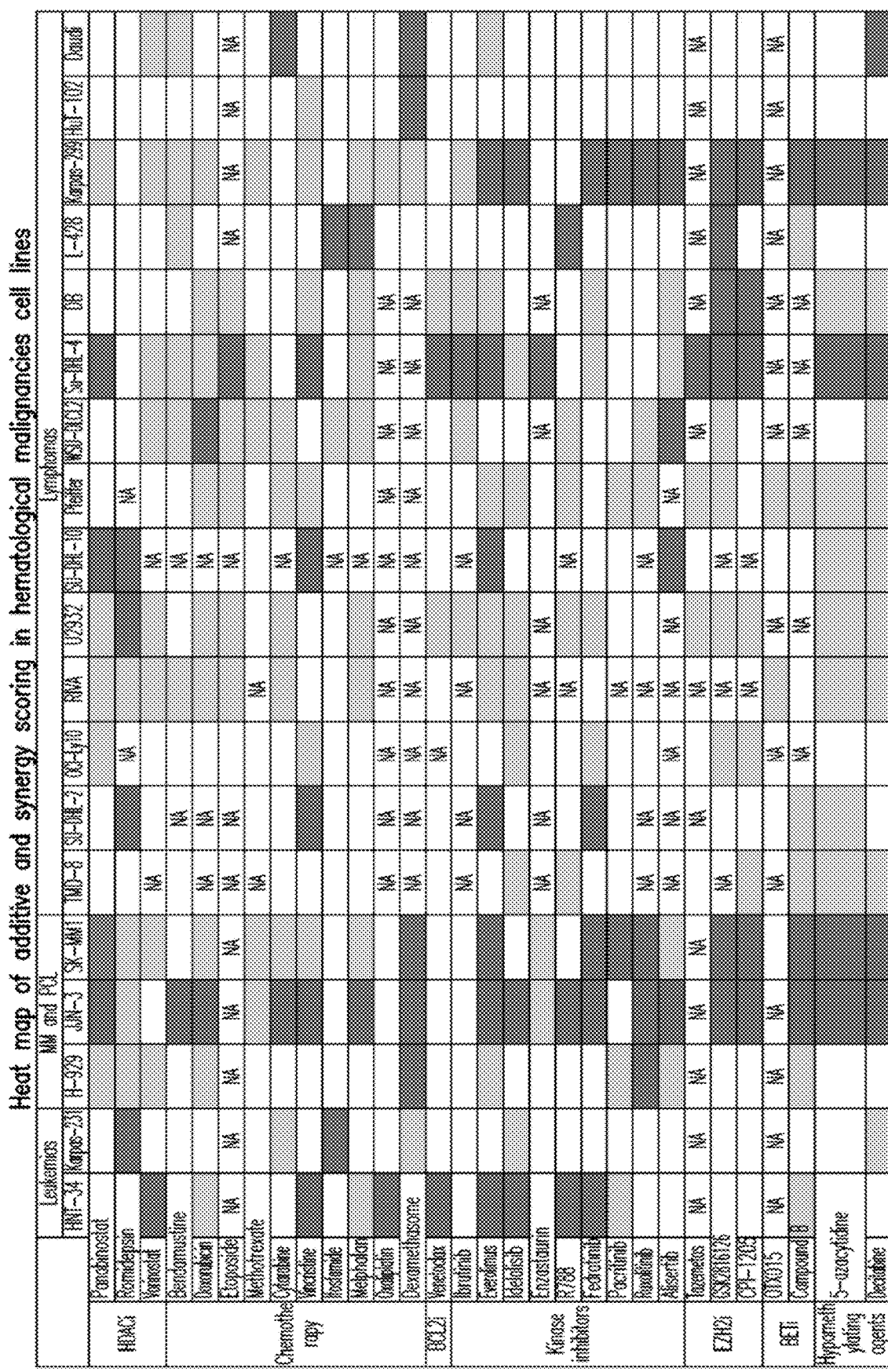
FIG. 2 shows heat map of additive (light grey) and synergy (dark grey) scoring of combination treatments of hematological malignancies cell lines with Compound 1 and second active agents.
Figure 2:
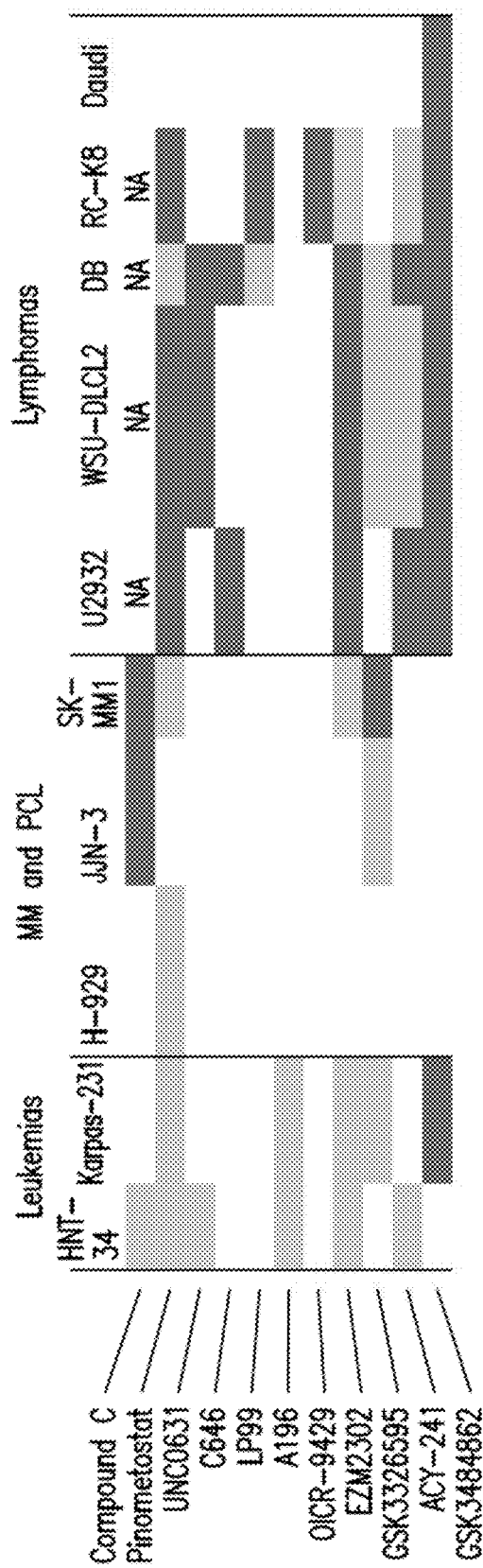

A wide range of additive or synergistic effects was observed across selected cell lines. All tested combinations showed additive (light grey) or synergistic (dark grey) effects in at least one of the 19 cell lines tested, independently of Compound 1 activity on proliferation of those cell lines (FIG. 2). Treatment of very sensitive cell lines such as JJN-3, SU-DHL2 or SU-DHL10 showed synergistic effects when treated with Compound 1 and a number of compounds including panobinostat, romidepsin, vincristine, everolimus, fedratinib, alisertib, and birabresib. Even more Compound 1 resistant cell lines such as DB, HNT-34 or SU-DHL4 also showed this benefit when Compound 1 was combined with a number of compounds including panobinostat, etoposide, vincristine, venetoclax, ibrutinib, everolimus, enzastaurin, tazemetostat, GSK126, CPI-1205, 5-azacytidine, and decitabine.

All disease subtypes tested (lymphomas, leukemias and multiple myeloma) benefited from the combination treatments of clinically relevant compounds or other epigenetic agents with Compound 1.

6.3 Anti-Tumor Activity of Compound 1 Alone and in Combination with 5-Azacytidine in WSU-DLCL2 (DLBCL) Xenograft Model Anti-tumor activity of Compound 1 alone and in combination with 5-azacytidine was studies in WSU-DLCL2 (DLBCL) xenograft model. Compound 1 (1 mg/kg) was administered once daily for 5 consecutive days followed by 2 days off (5D on/2D off) and 5-azacytidine (1 mg/kg) was administered once daily (QD). Compound 1 (1 mg/kg, 5D on/2D off) and 5-azacytidine (1 mg/kg, QD) inhibited WSU-DLCL2 DLBCL tumor growth. Combination treatment of Compound 1 and 5-azacytidine showed synergistic antitumor activity.

Methods: Xenograft study was conducted with female SCID mice bearing WSU-DLCL2 DLBCL xenograft tumors. Female SCID mice were inoculated subcutaneously with WSU-DLCL2 cells in the flank region above the right hind leg. Following inoculation of animals, the tumors were allowed to grow to approximately 200 mm$^3$ prior to randomization. On day 14 following tumor cell inoculation, the mice bearing WSU-DLCL2 tumors ranging between 150 and 250 mm$^3$ were pooled together and randomized into various treatment groups. Compound 1 was formulated in 0.5% Methyl Cellulose, 0.25% Tween 80 and 50 mM Citrate pH 3 in water. 5-Azacytidine was formulated in 0.9% saline. Compound 1 (1 mg/kg) was orally administered with three cycles of once daily for 5 consecutive days followed by 2 days off starting from day 14 after tumor cell inoculation. 5-Azacytidine (1 mg/kg) was intraperitoneally administered once a day (QD) for three weeks. In combination group the animals received Compound 1 (1 mg/kg/5D on/2D off) and 5-azacytidine (1 mg/kg, QD) simultaneously for three weeks starting from day 14 after tumor cell inoculation. Tumors were measured twice a week using calipers and tumor volumes were calculated using the formula of $W^2 \times L/2$. Statistical analysis was performed using a one-way or 2-way analysis of variance (ANOVA). Synergy calculations were performed using fractional product method.

Figure 3:
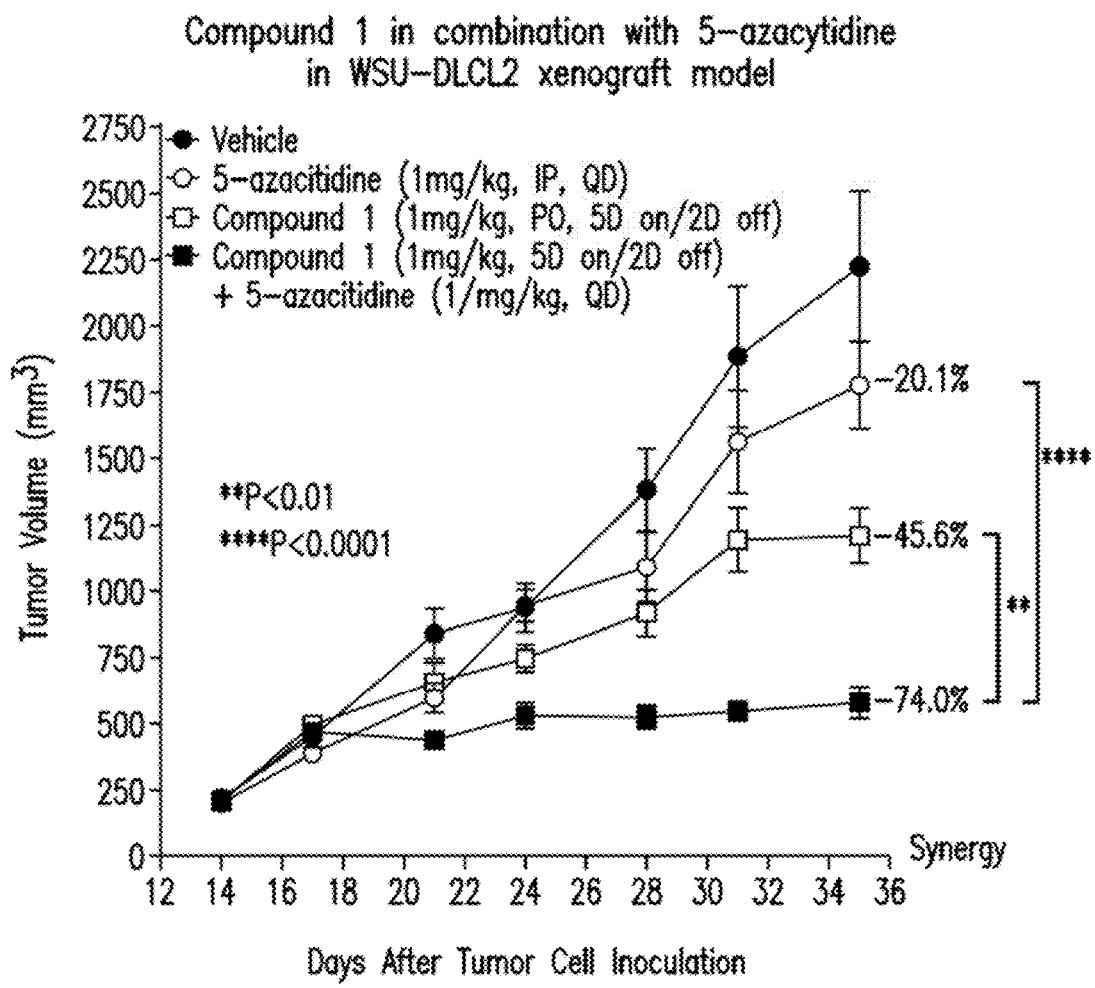
FIG. 3 shows anti-tumor activity of Compound 1 alone and in combination with 5-azacytidine in WSU-DLCL2 (DLBCL) xenograft model.

Results & Conclusions: Compound 1 (1 mg/kg) and 5-azacytidine (1 mg/kg) were tested as single agents and in combination in WSU-DLCL2 xenograft model. As a single agent Compound 1 significantly (p<0.0001) inhibited (45.6%) WSU-DLCL2 DLBCL tumor growth. 5-Azacytidine as single agent marginally (−20.1%) inhibited WSU-DLCL2 DLBCL xenograft tumor growth (FIG. 3). Compound 1 at 1 mg/kg when administered in combination with 5-azacytidine 1 mg/kg yielded a significant (p<0.0001) decrease in tumor volume when compared with vehicle control, displaying a tumor volume reduction of 74% compared to vehicle control (FIG. 3). In a 2-way ANOVA with Bonferroni's post-test, this combination antitumor activity was significantly better than Compound 1 alone (74% versus 45.6% TVR; p<0.0001) or 5-azacytidine alone (74% versus 20.1% TVR; p<0.01). Using the fractional product method, the combination antitumor activity of Compound 1 at 1 mg/kg and 5-azacytidine at 1 mg/kg was determined to be synergistic in decreasing tumor volume.

In conclusion, Compound 1 in combination with 5-azacytidine exhibited synergism in reducing tumor volume in the WSU-DLCL2 DLBCL xenograft tumor model.

6.4 Anti-Tumor Activity of Compound 1 Alone and in Combination with Tazemetostat in WSU-DLCL2 (DLBCL) Xenograft Model Anti-tumor activity of Compound 1 alone and in combination with tazemetostat was studied in WSU-DLCL2

(DLBCL) xenograft model. Compound 1 (1 mg/kg) was administered once daily for 5 consecutive days followed by 2 days off (5D on/2D off) and tazemetostat (200 mg/kg) was administered twice daily (BID). Combination treatment of Compound 1 and tazemetostat showed synergistic antitumor activity.

Methods: Xenograft study was conducted with female SCID mice bearing WSU-DLCL2 DLBCL xenograft tumors. Female SCID mice were inoculated subcutaneously with WSU-DLCL2 cells in the flank region above the right hind leg. Following inoculation of animals, the tumors were allowed to grow to approximately 200 mm$^3$ prior to randomization. On day 14 following tumor cell inoculation, the mice bearing WSU-DLCL2 tumors ranging between 150 and 250 mm$^3$ were pooled together and randomized into various treatment groups. Compound 1 was formulated in 0.5% Methyl Cellulose, 0.25% Tween 80 and 50 mM Citrate pH 3 in water. Tazemetostat was formulated in CMC-Tween. Compound 1 (1 mg/kg) was orally administered with three cycles of once daily for 5 consecutive days followed by 2 days off starting from day 14 after tumor cell inoculation. Tazemetostat 200 mg/kg) was orally administered twice day (BID) for three weeks. In combination group the animals received Compound 1 (1 mg/kg/5D on/2D off) and tazemetostat (200 mg/kg, BID) simultaneously for three weeks starting from day 14 after tumor cell inoculation. Tumors were measured twice a week using calipers and tumor volumes were calculated using the formula of W$^2$×L/2. Statistical analysis was performed using a one-way or 2-way analysis of variance (ANOVA). Synergy calculations were performed using fractional product method.

Figure 4:
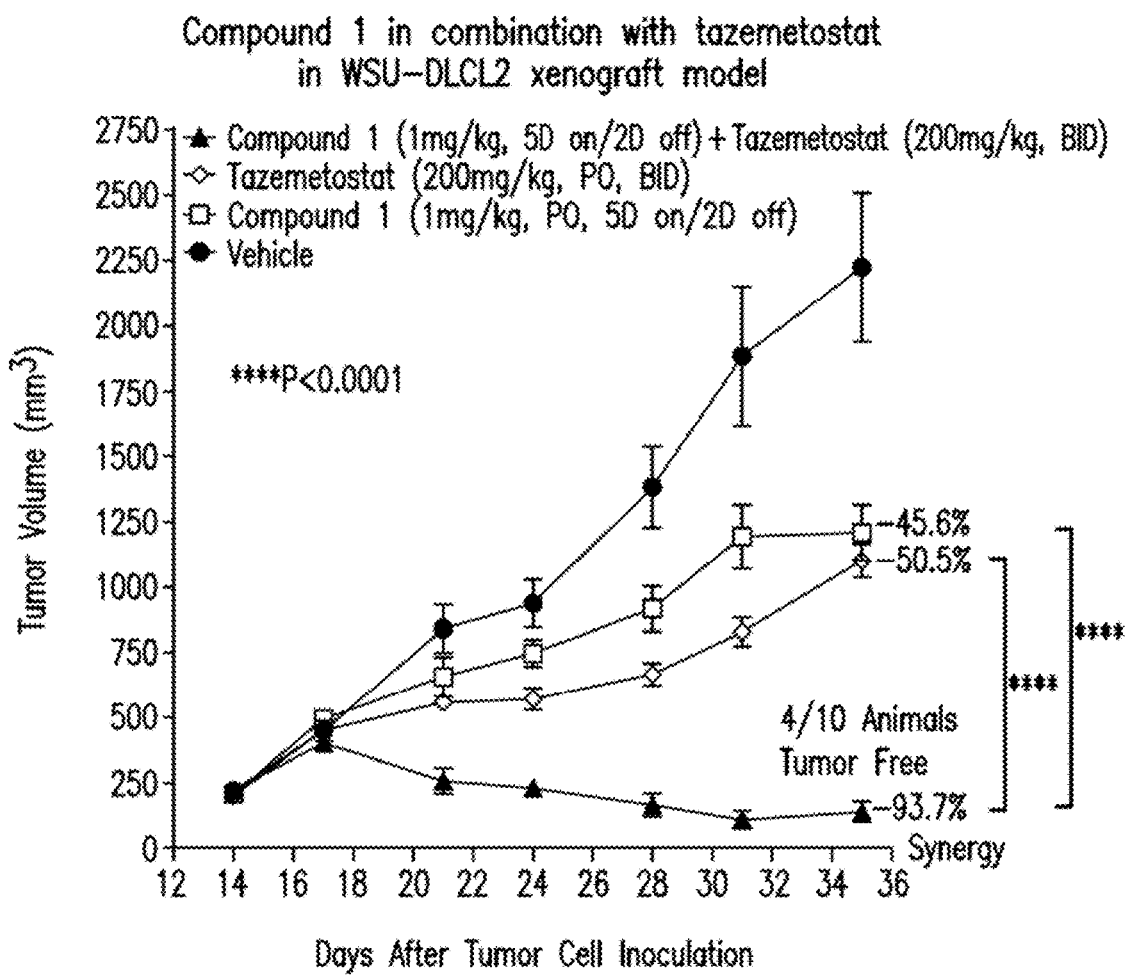
FIG. 4 shows anti-tumor activity of Compound 1 alone and in combination with tazemetostat in WSU-DLCL2 (DLBCL) xenograft model.

Results & Conclusions: Compound 1 (1 mg/kg) and tazemetostat (200 mg/kg) were tested as single agents and in combination in WSU-DLCL2 xenograft model. As a single agent Compound 1 significantly (p<0.0001) inhibited (45.6%) WSU-DLCL2 DLBCL tumor growth. Tazemetostat as single agent significantly (p<0.0001) inhibited (−50.5%) WSU-DLCL2 DLBCL xenograft tumor growth (FIG. 4). Compound 1 at 1 mg/kg when administered in combination with tazemetostat 200 mg/kg yielded a significant (p<0.0001) decrease in tumor volume when compared with vehicle control, displaying a tumor volume reduction of 93.7%% compared to vehicle control (FIG. 4). In a 2-way ANOVA with Bonferroni's post-test, this combination antitumor activity was significantly better than Compound 1 alone (93.7% versus 45.6TVR; p<0.0001) or tazemetostat alone (93.7% versus 50.5% TVR; p<0.0001). Using the fractional product method, the combination antitumor activity of Compound 1 at 1 mg/kg and tazemetostat at 200 mg/kg was determined to be synergistic in decreasing tumor volume.

In conclusion, Compound 1 in combination with tazemetostat exhibited synergism in reducing tumor volume in the WSU-DLCL2 DLBCL xenograft tumor model.

6.5 Anti-Tumor Activity of Compound 1 Alone and in Combination with Tazemetostat in DB (DLBCL) Xenograft Model Anti-tumor activity of Compound 1 alone and in combination with tazemetostat was studied in DB (DLBCL) xenograft model. Compound 1 (3, 10 or 30 mg/kg) was administered once daily for 5 consecutive days followed by 2 days off (5D on/2D off) and tazemetostat (200 mg/kg) was administered twice daily (BID). Combination treatment of Compound 1 and tazemetostat showed synergistic antitumor activity.

Methods: Xenograft study was conducted with female SCID mice bearing DB DLBCL xenograft tumors. Female SCID mice were inoculated subcutaneously with DB cells in the flank region above the right hind leg. Following inoculation of animals, the tumors were allowed to grow to approximately 200 mm$^3$ prior to randomization. On day 33 following tumor cell inoculation, the mice bearing DB tumors ranging between 150 and 250 mm$^3$ were pooled together and randomized into various treatment groups. Compound 1 was formulated in 0.5% Methyl Cellulose, 0.25% Tween 80 and 50 mM Citrate pH 3 in water. Tazemetostat was formulated in CMC-Tween. Compound 1 (3, 10 or 30 mg/kg) was orally administered with three cycles of once daily for 5 consecutive days followed by 2 days off starting from day 33 after tumor cell inoculation. Tazemetostat (200 mg/kg) was orally administered twice day (BID) for three weeks. In combination group the animals received Compound 1 (3, 10 or 30 mg/kg, 5D on/2D off) and tazemetostat (200 mg/kg, BID) simultaneously for three weeks starting from day 33 after tumor cell inoculation. Tumors were measured twice a week using calipers and tumor volumes were calculated using the formula of W$^2$×L/2. Statistical analysis was performed using a one-way or 2-way analysis of variance (ANOVA). Synergy calculations were performed using fractional product method.

Results & Conclusions: Compound 1 (3, 10 or 30 mg/kg) and tazemetostat (200 mg/kg) were tested as single agents and in combination in DB xenograft model. As a single agent Compound 1 at 3, 10 and 30 mg/kg inhibited DB DLBCL tumor growth with tumor volume reduction of 16.9%, 41.1% and 48.9%, respectively (FIG. 5A, FIG. 5B, and FIG. 5C). Tazemetostat as a single agent significantly inhibited (45.9%) DB xenograft tumor growth. Compound 1 at 3, 10 or 30 mg/kg when administered in combination with tazemetostat 200 mg/kg yielded a significant (p<0.0001) decrease in tumor volume when compared with vehicle control, displaying a tumor volume reduction of 99.1%, 100% and 100%, respectively (FIG. 5A, FIG. 5B, and FIG. 5C). A 90%, 100% and 100% of the animals treated with tazemetostat in combination with 3, 10 or 30 mg/kg Compound 1, respectively were tumor free. In a 2-way ANOVA with Bonferroni's post-test, this combination antitumor activity was significantly better than Compound 1 at 3, 10 or 30 mg/kg alone (99.1%, 100% or 100% versus 16.9, 41.1% or 48.9% TVR, respectively; p<0.0001 for all) or tazemetostat alone (99.1%, 100% or 100% versus 64.5% TVR; p<0.0001 for all). Using the fractional product method, the combination antitumor activity of Compound 1 at 3, 10 or 30 mg/kg and tazemetostat at 200 mg/kg was determined to be synergistic in decreasing tumor volume.

In conclusion, Compound 1 in combination with tazemetostat exhibited synergism in reducing tumor volume in the DB DLBCL tumor model.

6.6 Antiproliferative Effect of Compound 1 in Combination with Venetoclax in B-Cell CLL Patient Cells CLL is characterized by accumulation of clonal CD5$^+$ CD19$^+$ lymphocytes resistant to apoptosis. Venetoclax blocks the anti-apoptotic B-cell lymphoma-2 (Bcl-2) protein, leading to programmed cell death of CLL cells and is currently being tested in the clinic with different combinations for relapsed refractory patients. The effect of Compound 1 in combination with venetoclax on the proliferation and survival of CLL B cells was assessed utilizing an ex vivo model where primary CLL cells from patient-derived blood were stimulated to proliferate with 10% fetal bovine serum (FBS), 5 ng/mL recombinant human interleukine-4 (rh IL-4), 10 ng/mL recombinant human interleukine-10 (rh IL-10) and co-cultured with fibroblast expressing surface CD154 (CD40L) in a 96 well plate format.

Peripheral blood mononuclear cells (PBMCs) from CLL patients (Table 6) containing 52%-86% of CD5$^+$CD19$^+$ tumor cells were cultured at a density of 0.06-0.1×10$^6$ cells/well on a monolayer of CD154-expressing fibroblasts at a density of 0.09×10$^6$ cells/well in 96-well plates in RPMI 1640 medium supplemented with 10% FBS, 5 ng/mL rh IL-4 and 10 ng/mL rh IL-10 and were simultaneously treated with vehicle control (0.1% DMSO) or increasing concentrations of Compound 1 ranging from 0.0001 to 1 µM and venetoclax at concentrations ranging from 0.001 to 10 µM across all the different concentrations of Compound 1. After 144 hrs of treatment with both the agents, flow cytometric analysis was used to determine the number of tumor cells that were viable or apoptotic.

After 6 days of treatment, the tumor cell count was assessed by staining the patient PBMCs in each condition with tumor cell surface markers CD5 & CD19 along with Live/Dead fixable dye to exclude the dead cells and followed by intracellular staining for Caspase 3 antibody to identify the apoptotic cells and was measured by flow cytometry (Attune N×T, Thermo Fisher). The live tumor cell count for each condition was calculated by normalizing to the precision count beads added to each sample.

TABLE 6

Characteristics of the CLL Samples Used.

| CLL Pt | Tumor Burden | IGHV Mutation Status | Cytogenetics | Prior Therapy |
|---|---|---|---|---|
| 11 | 85% | Non-Mutated | del(13q) | N |
| 12 | 75% | Non-Mutated | del(13q) (35%) | N |
| 13 | 30% | Mutated | del(13q); tri12 | N |
| 14 | 86% | Mutated | del(13q); anamoly in cell interphase (86%) | Mitomycin |

The live tumor cell count was then normalized to the DMSO control (considered as 1000%) to calculate the percentage of viable cells remaining after treatment. The normalized percentage of tumor cells was then represented as heat map using Graph Pad Prism 8.0.0 to indicate the degree of tumor toxicity for each of the combinations (FIG. 6).

For apoptosis analysis, the percentage of apoptosis combining both "early" (Caspase 3 positive and Live-Dead fixable dye negative) and "late" apoptosis (Caspase 3 and Live-Dead fixable dye positive) cell gates subtracting the baseline DMSO value was graphed using GraphPad Prism 8.0.0.0. The $Y_{max}$ (maximal percentage of apoptos is achieved) values from apoptosis curves were calculated by performing a nonlinear regression curve fitting using log (agonist) vs. normalized response—Variable slope analysis and identifying the maximum value on GraphPad Prism 8.0.0 (Table 7).

TABLE 7

Maximum Apoptosis Effect of Compound 1 in combination with Venetoclax

| Concentrations of Venetoclax | Ymax of Pt 11 (%) | Ymax of Pt 12 (%) | Ymax of Pt 13 (%) | Ymax of Pt 14 (%) |
|---|---|---|---|---|
| DMSO + Cpd1 DRC | 12.42 | 14.64 | 27.00 | 13.32 |
| 0.001 uM + Cpd1 DRC | 17.79 | 24.85 | 33.09 | 17.39 |
| 0.01 uM + Cpd1 DRC | 38.49 | 34.24 | 49.03 | 27.33 |
| 0.1 uM + Cpd1 DRC | 58.37 | 45.34 | 52.16 | 31.44 |
| 1 uM + Cpd1 DRC | 66.55 | 48.71 | 55.23 | 40.57 |
| 10 uM + Cpd1 DRC | 72.34 | 54.25 | 60.52 | 45.98 |
| Venetoclax alone | 64.98 | 43.47 | 50.25 | 33.32 |

6.7 Antiproliferative Effect of Compound 1 in Combination with Ilbrutinib in B-cell CLL Patient Cells CLL is characterized by accumulation of clonal CD5+ CD19$^+$ lymphocytes resistant to apoptosis. Ibrutinib is a selective inhibitor of Bruton's tyrosine kinase (BTK), which is a signaling molecule of the B-cell antigen receptor (BCR). It is currently the first line treatment for newly diagnosed CLL patients and is being investigated in different combinations for relapsed patients. The effect of Compound 1 in combination with ibrutinib on the proliferation and survival of CLL B cells was assessed utilizing an ex vivo model where primary CLL cells from patient-derived blood were stimulated to proliferate with 10% fetal bovine serum (FBS), 5 ng/mL recombinant human interleukine-4 (rh IL-4), 10 ng/mL recombinant human interleukine-10 (rh IL-10) and co-cultured with fibroblast expressing surface CD154 (CD40L) in a 96 well plate format.

Peripheral blood mononuclear cells (PBMCs) from CLL patients (Table 8) containing 52%-86% of CD5$^+$CD19$^+$ tumor cells were cultured at a density of 0.06-0.1×10$^6$ cells/well on a monolayer of CD154-expressing fibroblasts at a density of 0.09×10$^6$ cells/well in 96-well plates in RPMI 1640 medium supplemented with 10% FBS, 5 ng/mL rh IL-4 and 10 ng/mL rh IL-10 and were simultaneously treated with vehicle control (0.1% DMSO) or increasing concentrations of Compound 1 ranging from 0.0001 to 1 µM and ibrutinib at concentrations ranging from 0.001 to 10 µM across all the different concentrations of Compound 1. After 144 hrs of treatment with both the agents, flow cytometric analysis was used to determine the number of tumor cells that were viable or apoptotic.

The tumor cell count was assessed by staining the patient PBMCs in each condition with tumor cell surface markers CD5 & CD19 along with Live/Dead fixable dye to exclude the dead cells and followed by intracellular staining for Caspase3 antibody to identify the apoptotic cells and was measured by flow cytometry (Attune N×T, Thermo Fisher). The live tumor cell count for each condition was calculated by normalizing to the precision count beads added to each sample.

TABLE 8

Characteristics of the CLL Samples Used.

| CLL Pt | Tumor Burden | IGHV Mutation Status | Cytogenetics | Prior Therapy |
|---|---|---|---|---|
| 11 | 85% | Non-Mutated | del(13q) | N |
| 12 | 75% | Non-Mutated | del(13q) (35%) | N |
| 13 | 30% | Mutated | del(13q); tri12 | N |
| 14 | 86% | Mutated | del(13q); anamoly in cell interphase (86%) | Mitomycin |

The live tumor cell count was then normalized to the DMSO control (considered as 100%) to calculate the percentage of viable cells remaining after treatment. The normalized percentage of tumor cells was then represented as a heat map using Graph Pad Prism 8.0.0 to indicate the degree of tumor toxicity for each of the combinations (FIG. 7).

For apoptosis analysis, the percentage of apoptosis combining both "early" (Caspase 3 positive and Live-Dead fixable dye negative) and "late" apoptosis (Caspase 3 and Live-Dead fixable dye positive) cell gates subtracting the baseline DMSO value was graphed using GraphPad Prism 8.0.0.0. The $Y_{max}$ (maximal percentage of apoptosis achieved) values from apoptosis curves were calculated by performing a nonlinear regression curve fitting using log (agonist) vs. normalized response—Variable slope analysis and identifying the maximum value on GraphPad Prism 8.0.0 (Table 9).

TABLE 9

Maximum Apoptosis Effect of Compound 1 in combination with Ibrutinib

| Concentrations of Ibrutinib | Ymax of Pt 11 (%) | Ymax of Pt 12 (%) | Ymax of Pt 13 (%) | Ymax of Pt 14 (%) |
|---|---|---|---|---|
| DMSO + Cpd1 DRC | 14.40 | 14.19 | 36.93 | 17.21 |
| 0.001 uM + Cpd1 DRC | 19.80 | 15.67 | 26.75 | 17.87 |
| 0.01 uM + Cpd1 DRC | 18.66 | 13.66 | 30.53 | 18.30 |
| 0.1 uM + Cpd1 DRC | 12.33 | 17.47 | 32.49 | 13.59 |
| 1 uM + Cpd1 DRC | 19.73 | 22.48 | 29.70 | 17.65 |
| 10 uM + Cpd1 DRC | 29.73 | 24.18 | 35.37 | 19.33 |
| Ibrutinib alone | 0 | 0 | 0 | 0 |

6.8 Effect of Treatment with Compound 1 in Combination with BET Inhibitor on DLBCL Cell Line Proliferation A panel of DLBCL cell lines in the following table were treated with single-agent Compound 1, single agent Compound B (a BET inhibitor), along with the combinations of Compound 1 and Compound B, at a concentration range to investigate the antiproliferative activities.

TABLE 10

Diffuse Large B cell Lymphoma
Cell Lines Tested in Cell Titer-Glo ® Assay

| Cell line | Seeding Density | Subtype |
|---|---|---|
| DB | $0.1 \times 10^6$/mL | GCB |
| HT | $0.1 \times 10^6$/mL | GCB |
| KARPAS-422 | $0.1 \times 10^6$/mL | GCB |
| NU-DHL-1 | $0.1 \times 10^6$/mL | GCB |
| OCI-LY1 | $0.1 \times 10^6$/mL | GCB |
| OCI-LY7 | $0.1 \times 10^6$/mL | GCB |
| OCI-LY18 | $0.1 \times 10^6$/mL | GCB |
| OCI-LY19 | $0.1 \times 10^6$/mL | GCB |
| Pfeiffer | $0.2 \times 10^6$/mL | GCB |
| RC-K8 | $0.1 \times 10^6$/mL | GCB |
| SU-DHL-4 | $0.1 \times 10^6$/mL | GCB |
| SU-DHL-5 | $0.025 \times 10^6$/mL | GCB |
| SU-DHL-6 | $0.25 \times 10^6$/mL | GCB |
| SU-DHL-8 | $0.1 \times 10^6$/mL | GCB |
| SU-DHL-10 | $0.025 \times 10^6$/mL | GCB |
| SU-DHL-16 | $0.1 \times 10^6$/mL | GCB |
| Toledo | $0.1 \times 10^6$/mL | GCB |
| ULA | $0.1 \times 10^6$/mL | GCB |
| VAL | $0.1 \times 10^6$/mL | GCB |
| WILL-2 | $0.1 \times 10^6$/mL | GCB |
| WSU-DLCL2 | $0.1 \times 10^6$/mL | GCB |
| NU-DUL-1 | $0.1 \times 10^6$/mL | ABC |
| OCI-LY3 | $0.1 \times 10^6$/mL | ABC |
| OCI-LY10 | $0.1 \times 10^6$/mL | ABC |
| RIVA | $0.1 \times 10^6$/mL | ABC |
| SU-DHL-2 | $0.025 \times 10^6$/mL | ABC |
| TMD8 | $0.1 \times 10^6$/mL | ABC |
| U-2904 | $0.1 \times 10^6$/mL | ABC |
| U-2932 | $0.1 \times 10^6$/mL | ABC |
| U-2946 | $0.1 \times 10^6$/mL | ABC |
| U-2973 | $0.1 \times 10^6$/mL | ABC |
| Farage | $0.1 \times 10^6$/mL | PMBL |
| KARPAS-1106P | $0.1 \times 10^6$/mL | PMBL |
| U-2940 | $0.1 \times 10^6$/mL | PMBL |
| CARNAVAL | $0.1 \times 10^6$/mL | NS |
| ROS-50 | $0.1 \times 10^6$/mL | NS |
| STR-428 | $0.1 \times 10^6$/mL | NS |
| SU-DHL-1 | $0.05 \times 10^6$/mL | NS |
| WILL-1 | $0.1 \times 10^6$/mL | NS |
| WSU-DLCL | $0.1 \times 10^6$/mL | NS |

ABC = activated B cell-like; GCB = germinal center B cell-like; PMBL = primary mediastinal B cell lymphoma; NS = non-specified.

Experimental procedures: CellTiter-Glo (CTG), a luminescent dye that measures adenosine-5'-triphosphate (ATP), was used to quantify the cell proliferation across a panel of 40 unique DLBCL cell lines. Single agents and combinations were pre-spotted into 384-well plates (diluted in final dimethyl sulfoxide [DMSO] concentration of 0.1% for a maximal volume of 50 L). A 10-point dose response that includes a DMSO point for single agent Compound B (10 μM top, 3-fold serial dilution) and Compound 1 (10 μM top, 3-fold serial dilution for 16 lines and 1 M top, 4-fold serial dilution for 24 lines) were tested for the cell line panel and the 10×10 combination matrices utilized the same respective dose-response series as single agent. Inter-plate duplicates were utilized for all treatment conditions.

For each DLBCL cell line, 50 L of cell suspension at their respective seeding densities of 0.025 to 0.2×10$^6$ cells per mL were added to 384-well plates containing the compounds. The effect of the single agents and combinations on the proliferation/viability of cells was assessed after 5 days of incubation. Twenty-five microliters of CTG per well was then dispensed to the cell suspension, and ATP released by viable cells was measured after a 30-minute incubation as relative luminescence units (RLU) using an EnVision plate reader (PerkinElmer, Covina, Calif.). Single-agent and combination-mediated cytotoxicity is indicated by a lower ATP level in the media after 5-day incubation with drug compared to the Day 0 ATP level.

Data analysis: Percent growth was calculated by the equation "% Growth=(Day 5 CTG−Day 0 CTG)/(Day 0 CTG)." All data was analyzed by GraphPad Prism 7 with the XY analyses nonlinear regression curve fit using the parameters for "log(inhibitor) vs. response—Variable slope (four parameters)." Cytotoxicity was called if any part of the DRC CTG signal went below the Day 0 CTG read and cytostatic effects were indicated by the DRC CTG signal staying above the Day 0 line. Combination data was analyzed with the Bliss independence model for synergy and Highest Single Agent (HSA) model for additivity with p-values <0.01 to be considered significant.

Conclusion: The results are shown in FIG. 8. Combinations of Compound B and Compound 1 showed synergy and additivity in the majority of DLBCL cell lines with no subtype specificity.

The embodiments provided herein are not to be limited in scope by the specific embodiments provided in the examples which are intended as illustrations of a few aspects of the provided embodiments and any embodiments that are functionally equivalent are encompassed by the present disclosure. Indeed, various modifications of the embodiments provided herein in addition to those shown and described herein will become apparent to those skilled in the art and are intended to fall within the scope of the appended claims.

A number of references have been cited, the disclosures of which are incorporated herein by reference in their entirety.

What is claimed is:

1. A method of treating a hematological malignancy, comprising administering to a patient having the hematological malignancy a therapeutically effective amount of a compound in combination with a second active agent, wherein the compound is Compound 1:

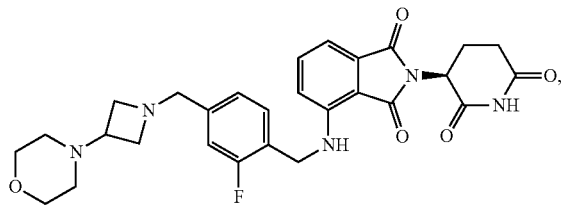

or an enantiomer, mixture of enantiomers, tautomer, isotopolog, or pharmaceutically acceptable salt thereof; and wherein the second active agent is an EZH2 inhibitor.

2. The method of claim 1, wherein
the EZH2 inhibitor is tazemetostat, GSK126, CPI-1205, 3-deazaneplanocin A (DZNep), EPZ005687, EI1, UNC1999, or sinefungin, or a stereoisomer, mixture of stereoisomers, tautomer, isotopolog, or pharmaceutically acceptable salt thereof.

3. The method of claim 1, wherein the compound is a hydrochloride salt of Compound 1.

4. The method of claim 1, wherein the hematological malignancy is acute myeloid leukemia (AML), acute lymphocytic leukemia (ALL), multiple myeloma (MM), non-Hodgkin's lymphoma (NHL), diffuse large B-cell lymphoma (DLBCL), Hodgkin's lymphoma (HL), T-cell lymphoma (TCL), Burkitt lymphoma (BL), chronic lymphocytic leukemia/small lymphocytic lymphoma (CLL/SLL), marginal zone lymphoma (MZL), or myelodysplastic syndromes (MDS).

5. The method of claim 4, wherein the hematological malignancy is relapsed or refractory.

6. The method of claim 4, wherein the hematological malignancy is newly diagnosed.

7. The method of claim 4, wherein the hematological malignancy is DLBCL.

8. The method of claim 7, wherein the DLBCL is relapsed or refractory DLBCL.

9. The method of claim 8, wherein the DLBCL is refractory to one or more of rituximab, cyclophosphamide, doxorubicin, vincristine, prednisone, etoposide, bendamustine, lenalidomide, or gemcitabine.

10. The method of claim 7, wherein the DLBCL is newly diagnosed DLBCL.

11. The method of claim 4, wherein the hematological malignancy is CLL/SLL.

12. The method of claim 11, wherein the CLL/SLL is relapsed or refractory CLL/SLL.

13. The method of claim 12, wherein the CLL/SLL is relapsed or refractory to at least two prior therapies.

14. The method of claim 13, wherein at least one of the prior therapies is a Bruton's tyrosine kinase (BTK) inhibitor.

15. The method of claim 14, wherein the BTK inhibitor is ibrutinib, acalabrutinib, zanubrutinib, or tirabrutinib.

16. The method of claim 11, wherein the CLL/SLL is newly diagnosed.

17. The method of claim 4, wherein the hematological malignancy is AML, and the AML is B-cell AML.

18. The method of claim 4, wherein the hematological malignancy is multiple myeloma, and the multiple myeloma is plasma cell leukemia (PCL).

19. The method of claim 4, wherein the hematological malignancy is TCL, and the TCL is anaplastic large cell lymphoma (ALCL) or Sezary Syndrome.

20. The method of claim 4, wherein the hematological malignancy is MZL, and the MZL is splenic marginal zone lymphoma (SMZL).

21. The method of claim 1, wherein the EZH2 inhibitor is tazemetostat, GSK126, or CPI-1205.

22. The method of claim 1, wherein the EZH2 inhibitor is tazemetostat, or a tautomer, isotopolog, or pharmaceutically acceptable salt thereof.

23. The method of claim 1, wherein the EZH2 inhibitor is tazemetostat.

24. The method of claim 23, wherein the compound is a hydrochloride salt of Compound 1.

25. The method of claim 23, wherein the hematological malignancy is acute myeloid leukemia (AML), acute lymphocytic leukemia (ALL), multiple myeloma (MM), non-Hodgkin's lymphoma (NHL), diffuse large B-cell lymphoma (DLBCL), Hodgkin's lymphoma (HL), T-cell lymphoma (TCL), Burkitt lymphoma (BL), chronic lymphocytic leukemia/small lymphocytic lymphoma (CLL/SLL), marginal zone lymphoma (MZL), or myelodysplastic syndromes (MDS).

26. The method of claim 25, wherein the hematological malignancy is relapsed or refractory.

27. The method of claim 25, wherein the hematological malignancy is newly diagnosed.

28. The method of claim 25, wherein the hematological malignancy is DLBCL.

29. The method of claim 28, wherein the DLBCL is relapsed or refractory DLBCL.

30. The method of claim 29, wherein the DLBCL is refractory to one or more of rituximab, cyclophosphamide, doxorubicin, vincristine, prednisone, etoposide, bendamustine, lenalidomide, or gemcitabine.

31. The method of claim 28, wherein the DLBCL is newly diagnosed DLBCL.

32. The method of claim 25, wherein the hematological malignancy is CLL/SLL.

33. The method of claim 32, wherein the CLL/SLL is relapsed or refractory CLL/SLL.

34. The method of claim 33, wherein the CLL/SLL is relapsed or refractory to at least two prior therapies.

35. The method of claim 34, wherein at least one of the prior therapies is a Bruton's tyrosine kinase (BTK) inhibitor.

36. The method of claim 35, wherein the BTK inhibitor is ibrutinib, acalabrutinib, zanubrutinib, or tirabrutinib.

37. The method of claim 32, wherein the CLL/SLL is newly diagnosed.

38. The method of claim 25, wherein the hematological malignancy is AML, and the AML is B-cell AML.

39. The method of claim 25, wherein the hematological malignancy is multiple myeloma, and the multiple myeloma is plasma cell leukemia (PCL).

40. The method of claim 25, wherein the hematological malignancy is TCL, and the TCL is anaplastic large cell lymphoma (ALCL) or Sezary Syndrome.

41. The method of claim 25, wherein the hematological malignancy is MZL, and the MZL is splenic marginal zone lymphoma (SMZL).

* * * * *